(12) United States Patent
Morgan et al.

(10) Patent No.: US 12,310,584 B2
(45) Date of Patent: May 27, 2025

(54) LOCKING ARRANGEMENTS FOR DETACHABLE SHAFT ASSEMBLIES WITH ARTICULATABLE SURGICAL END EFFECTORS

(71) Applicant: Cilag GmbH International, Zug (CH)

(72) Inventors: Jerome R. Morgan, Cincinnati, OH (US); Chester O. Baxter, III, Loveland, OH (US); Frederick E. Shelton, IV, Hillsboro, OH (US); Gary W. Knight, West Chester, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/485,751

(22) Filed: Oct. 12, 2023

(65) Prior Publication Data
US 2024/0032915 A1 Feb. 1, 2024

Related U.S. Application Data

(63) Continuation of application No. 17/197,337, filed on Mar. 10, 2021, now Pat. No. 11,812,958, which is a
(Continued)

(51) Int. Cl.
*A61B 17/29* (2006.01)
*A61B 17/072* (2006.01)
(Continued)

(52) U.S. Cl.
CPC ...... *A61B 17/072* (2013.01); *A61B 17/07207* (2013.01); *A61B 2017/00398* (2013.01);
(Continued)

(58) Field of Classification Search
None
See application file for complete search history.

(56) References Cited

U.S. PATENT DOCUMENTS

| | | |
|---|---|---|
| 5,403,312 A | 4/1995 | Yates et al. |
| 5,489,290 A | 2/1996 | Furnish |
| (Continued) | | |

FOREIGN PATENT DOCUMENTS

| | | |
|---|---|---|
| CN | 101116627 A | 2/2008 |
| EP | 1785097 A2 | 5/2007 |
| (Continued) | | |

OTHER PUBLICATIONS

Brazilian Examination Report dated Apr. 1, 2020, for Application No. 112017013037-8, 4 pages.
(Continued)

*Primary Examiner* — Joshua G Kotis
(74) *Attorney, Agent, or Firm* — Frost Brown Todd LLC

(57) ABSTRACT

A surgical instrument. In one form, the surgical instrument includes a housing that has an interchangeable shaft assembly removably attached thereto. The interchangeable shaft assembly includes an elongate shaft that has a surgical end effector operably coupled thereto for selective articulation relative to the elongate shaft. An articulation system is configured to selectively apply articulation motions to the surgical end effector when the articulation system is in an actuated orientation. A locking arrangement prevents detachment of the interchangeable shaft assembly from the housing when the articulation system is in the actuated orientation.

20 Claims, 30 Drawing Sheets

Related U.S. Application Data continuation of application No. 16/021,321, filed on Jun. 28, 2018, now Pat. No. 10,945,728, which is a continuation of application No. 14/575,148, filed on Dec. 18, 2014, now Pat. No. 10,085,748.

(51) Int. Cl.
 *A61B 17/00* (2006.01)
 *A61B 34/30* (2016.01)

(52) U.S. Cl.
 CPC ........... *A61B 2017/00407* (2013.01); *A61B 2017/0046* (2013.01); *A61B 2017/00473* (2013.01); *A61B 2017/00477* (2013.01); *A61B 2017/00734* (2013.01); *A61B 2017/07271* (2013.01); *A61B 2017/07285* (2013.01); *A61B 2017/2927* (2013.01); *A61B 2017/2946* (2013.01); *A61B 34/30* (2016.02)

(56) References Cited

U.S. PATENT DOCUMENTS

| | | | |
|---|---|---|---|
| 5,632,432 A | 5/1997 | Schulze et al. | |
| 5,702,408 A | 12/1997 | Wales et al. | |
| 5,704,534 A | 1/1998 | Huitema et al. | |
| 5,792,135 A | 8/1998 | Madhani et al. | |
| 5,865,361 A | 2/1999 | Milliman et al. | |
| 5,878,193 A | 3/1999 | Wang et al. | |
| 6,132,368 A | 10/2000 | Cooper | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,793,669 B2 | 9/2004 | Nakamura et al. | |
| 7,000,818 B2 | 2/2006 | Shelton, IV et al. | |
| 7,422,139 B2 | 9/2008 | Shelton, IV et al. | |
| 7,461,767 B2 * | 12/2008 | Viola .............. | A61B 17/07207 227/176.1 |
| 7,464,849 B2 | 12/2008 | Shelton, IV et al. | |
| 7,524,320 B2 | 4/2009 | Tierney et al. | |
| 7,670,334 B2 | 3/2010 | Hueil et al. | |
| 7,691,098 B2 | 4/2010 | Wallace et al. | |
| 7,753,245 B2 | 7/2010 | Boudreaux et al. | |
| 7,806,891 B2 | 10/2010 | Nowlin et al. | |
| 7,824,401 B2 | 11/2010 | Manzo et al. | |
| 7,845,514 B2 | 12/2010 | Rush et al. | |
| 7,950,562 B2 | 5/2011 | Beardsley et al. | |
| 7,980,443 B2 | 7/2011 | Scheib et al. | |
| 8,154,239 B2 * | 4/2012 | Katsuki ............ | G05B 23/0256 318/565 |
| 8,210,411 B2 | 7/2012 | Yates et al. | |
| 8,220,688 B2 | 7/2012 | Laurent et al. | |
| 8,277,473 B2 * | 10/2012 | Sunaoshi .............. | A61B 90/90 606/1 |
| 8,308,040 B2 | 11/2012 | Huang et al. | |
| 8,393,514 B2 | 3/2013 | Shelton, IV et al. | |
| 8,517,239 B2 * | 8/2013 | Scheib ................ | A61B 17/068 310/156.01 |
| 8,561,870 B2 | 10/2013 | Baxter, III et al. | |
| 8,585,583 B2 * | 11/2013 | Sakaguchi ............ | A61B 34/71 600/106 |
| 8,608,045 B2 | 12/2013 | Smith et al. | |
| 8,708,211 B2 | 4/2014 | Zemlok et al. | |
| 8,733,613 B2 | 5/2014 | Huitema et al. | |
| 8,777,898 B2 | 7/2014 | Suon et al. | |
| 8,807,414 B2 | 8/2014 | Ross et al. | |
| 8,857,693 B2 | 10/2014 | Schuckmann et al. | |
| 9,072,535 B2 | 7/2015 | Shelton, IV et al. | |
| 9,101,358 B2 | 8/2015 | Kerr et al. | |
| 9,307,986 B2 | 4/2016 | Hall et al. | |
| 9,326,767 B2 | 5/2016 | Koch, Jr. et al. | |
| 9,332,987 B2 | 5/2016 | Leimbach et al. | |
| 9,345,481 B2 | 5/2016 | Hall et al. | |
| 9,351,726 B2 | 5/2016 | Leimbach et al. | |
| 9,351,727 B2 | 5/2016 | Leimbach et al. | |
| 9,358,003 B2 | 6/2016 | Hall et al. | |
| 9,358,004 B2 | 6/2016 | Sniffin et al. | |
| 9,398,911 B2 | 7/2016 | Auld | |
| 9,468,438 B2 | 10/2016 | Baber et al. | |
| 9,554,794 B2 | 1/2017 | Baber et al. | |
| 9,629,623 B2 | 4/2017 | Lytle, IV et al. | |
| 9,629,629 B2 | 4/2017 | Leimbach et al. | |
| 9,649,110 B2 | 5/2017 | Parihar et al. | |
| 9,687,230 B2 | 6/2017 | Leimbach et al. | |
| 9,690,362 B2 | 6/2017 | Leimbach et al. | |
| 9,700,309 B2 | 7/2017 | Jaworek et al. | |
| 9,724,094 B2 | 8/2017 | Baber et al. | |
| 9,733,663 B2 | 8/2017 | Leimbach et al. | |
| 9,737,301 B2 | 8/2017 | Baber et al. | |
| 9,743,929 B2 | 8/2017 | Leimbach et al. | |
| 9,750,499 B2 | 9/2017 | Leimbach et al. | |
| 9,757,128 B2 | 9/2017 | Baber et al. | |
| 9,782,169 B2 | 10/2017 | Kimsey et al. | |
| 9,782,187 B2 | 10/2017 | Zergiebel et al. | |
| 9,788,836 B2 | 10/2017 | Overmyer et al. | |
| 9,801,626 B2 | 10/2017 | Parihar et al. | |
| 9,804,618 B2 | 10/2017 | Leimbach et al. | |
| 9,808,244 B2 | 11/2017 | Leimbach et al. | |
| 9,814,460 B2 | 11/2017 | Kimsey et al. | |
| 9,820,738 B2 | 11/2017 | Lytle, IV et al. | |
| 9,826,976 B2 | 11/2017 | Parihar et al. | |
| 9,826,977 B2 | 11/2017 | Leimbach et al. | |
| 9,844,368 B2 | 12/2017 | Boudreaux et al. | |
| 9,844,374 B2 | 12/2017 | Lytle, IV et al. | |
| 9,844,375 B2 | 12/2017 | Overmyer et al. | |
| 9,867,612 B2 | 1/2018 | Parihar et al. | |
| 9,883,860 B2 | 2/2018 | Leimbach et al. | |
| 9,888,919 B2 | 2/2018 | Leimbach et al. | |
| 9,943,309 B2 | 4/2018 | Shelton, IV et al. | |
| 9,968,355 B2 | 5/2018 | Shelton, IV et al. | |
| 9,987,000 B2 | 6/2018 | Shelton, IV et al. | |
| 10,004,497 B2 | 6/2018 | Overmyer et al. | |
| 10,004,501 B2 | 6/2018 | Shelton, IV et al. | |
| 10,013,049 B2 | 7/2018 | Leimbach et al. | |
| 10,016,199 B2 | 7/2018 | Baber et al. | |
| 10,028,761 B2 | 7/2018 | Leimbach et al. | |
| 10,085,748 B2 | 10/2018 | Morgan et al. | |
| 10,111,679 B2 | 10/2018 | Baber et al. | |
| 10,117,649 B2 | 11/2018 | Baxter, III et al. | |
| 10,135,242 B2 | 11/2018 | Baber et al. | |
| 10,136,887 B2 | 11/2018 | Shelton, IV et al. | |
| 10,149,680 B2 | 12/2018 | Parihar et al. | |
| 10,188,385 B2 | 1/2019 | Kerr et al. | |
| 10,201,364 B2 | 2/2019 | Leimbach et al. | |
| 10,245,027 B2 | 4/2019 | Shelton, IV et al. | |
| 10,405,857 B2 | 9/2019 | Shelton, IV et al. | |
| 10,470,762 B2 | 11/2019 | Leimbach et al. | |
| 10,945,728 B2 | 3/2021 | Morgan et al. | |
| 11,812,958 B2 | 11/2023 | Morgan et al. | |
| 2004/0092912 A1 * | 5/2004 | Jinno ................... | A61B 34/72 606/1 |
| 2004/0232201 A1 | 11/2004 | Wenchell et al. | |
| 2005/0006432 A1 | 1/2005 | Racenet et al. | |
| 2006/0229665 A1 | 10/2006 | Wales et al. | |
| 2007/0152014 A1 | 7/2007 | Gillum et al. | |
| 2007/0175955 A1 | 8/2007 | Shelton, IV et al. | |
| 2008/0046003 A1 | 2/2008 | Renger et al. | |
| 2008/0245842 A1 * | 10/2008 | Marczyk .............. | A61B 17/068 227/175.1 |
| 2009/0090763 A1 * | 4/2009 | Zemlok ............ | A61B 17/07207 227/175.2 |
| 2009/0108048 A1 * | 4/2009 | Zemlok .................. | G16Z 99/00 227/176.1 |
| 2010/0193566 A1 * | 8/2010 | Scheib ............ | A61B 17/07207 227/180.1 |
| 2010/0228283 A1 * | 9/2010 | Jinno ..................... | A61B 34/70 606/205 |
| 2011/0017801 A1 * | 1/2011 | Zemlok ............ | A61B 17/07207 227/175.1 |
| 2011/0112517 A1 | 5/2011 | Peine et al. | |
| 2011/0155781 A1 * | 6/2011 | Swensgard ...... | A61B 17/07207 227/176.1 |
| 2011/0238044 A1 | 9/2011 | Main et al. | |

(56) References Cited

U.S. PATENT DOCUMENTS

| | | |
|---|---|---|
| 2011/0290854 A1 | 12/2011 | Timm et al. |
| 2012/0074197 A1* | 3/2012 | Marczyk ............ A61B 17/0682 227/175.1 |
| 2012/0078244 A1 | 3/2012 | Worrell et al. |
| 2012/0080493 A1 | 4/2012 | Shelton, IV et al. |
| 2012/0116389 A1* | 5/2012 | Houser .......... A61B 17/320092 606/1 |
| 2012/0197190 A1* | 8/2012 | Suon ................ A61M 25/0133 604/95.04 |
| 2013/0090576 A1* | 4/2013 | Stulen ............ A61B 17/320092 601/2 |
| 2013/0214025 A1* | 8/2013 | Zemlok ............ A61B 17/07207 227/175.1 |
| 2013/0253480 A1 | 9/2013 | Kimball et al. |
| 2013/0274722 A1 | 10/2013 | Kostrzewski et al. |
| 2014/0012289 A1 | 1/2014 | Snow et al. |
| 2014/0236174 A1* | 8/2014 | Williams .......... A61B 17/07207 606/130 |
| 2014/0246475 A1 | 9/2014 | Hall et al. |
| 2014/0249557 A1 | 9/2014 | Koch, Jr. et al. |
| 2014/0263541 A1 | 9/2014 | Leimbach et al. |
| 2014/0263552 A1 | 9/2014 | Hall et al. |
| 2014/0373652 A1 | 12/2014 | Zergiebel et al. |
| 2015/0060517 A1 | 3/2015 | Williams |
| 2015/0076205 A1 | 3/2015 | Zergiebel |
| 2015/0083774 A1* | 3/2015 | Measamer ........... A61B 17/068 227/175.1 |
| 2015/0157321 A1* | 6/2015 | Zergiebel ............... H01R 39/08 227/175.1 |
| 2015/0173746 A1* | 6/2015 | Baxter, III ....... A61B 17/07207 227/176.1 |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2016/0066913 A1 | 3/2016 | Swayze et al. |
| 2019/0183500 A1* | 6/2019 | Shelton, IV ..... A61B 17/07207 |

FOREIGN PATENT DOCUMENTS

| | | |
|---|---|---|
| EP | 1884201 A1 | 2/2008 |
| EP | 2042107 A1 | 4/2009 |
| EP | 2743042 A2 | 6/2014 |
| EP | 2767243 A2 | 8/2014 |
| JP | H10-113352 A | 5/1998 |
| JP | 2005-028150 A | 2/2005 |
| KR | 20100110134 A | 10/2010 |
| WO | WO 2001/062163 A1 | 8/2001 |
| WO | WO 2012/125618 A1 | 9/2012 |
| WO | WO 2014/027846 A1 | 2/2014 |
| WO | WO 2014/158882 A2 | 10/2014 |
| WO | WO 2015/148141 A1 | 10/2015 |
| WO | WO 2016/100070 A2 | 6/2016 |

OTHER PUBLICATIONS

Chinese Office Action, Notification of First Office Action dated Aug. 2, 2019, for Application No. 201580076418.3, 8 pages.
Chinese Search Report dated Jul. 25, 2019, for Application No. 201580076418.3, 2 pages.
European Partial Search Report dated Jun. 8, 2016, for Application No. 15200727.4, 10 pages.
European Search Report, Extended, and Written Opinion dated Oct. 5, 2016, for Application No. 15200727.4, 15 pages.
European Search Report, Extended, and Written Opinion dated Nov. 20, 2019, for Application No. 19191101.5, 9 pages.
Indian Examination Report dated Jan. 6, 2020, for Application No. 201717019698, 6 pages.
International Search Report and Written Opinion dated Aug. 11, 2016, for International Application No. PCT/US2015/063960, 23 pages.
Japanese Notification of Reasons for Refusal dated Oct. 1, 2019, for Application No. 2017-532980, 6 pages.
Japanese Search Report dated Sep. 27, 2019, for Application No. 2017-532980, 17 pages.
Japanese Decision to Grant a Patent dated Apr. 7, 2020, for Application No. 2017-532980, 2 pages.
US Provisional U.S. Appl. No. 61/812,365 entitled, "Surgical Instrument with Multiple Functions Performed by a Single Motor."
US Provisional U.S. Appl. No. 61/812,372 entitled "Surgical Instrument with Multiple Functions Performed by a Single Motor."
US Provisional U.S. Appl. No. 61/812,376 entitled, "Linear Cutter with Power."
US Provisional U.S. Appl. No. 61/812,382 entitled, "Linear Cutter with Motor and Pistol Grip."
US Provisional U.S. Appl. No. 61/812,385 entitled, "Surgical Instrument Handle with Multiple Actuation Motors and Motor Control."
US Non-Provisional U.S. Appl. No. 12/031,573 entitled, "Surgical Cutting and Fastening Instrument Having RF Electrodes," filed Feb. 14, 2008.

* cited by examiner

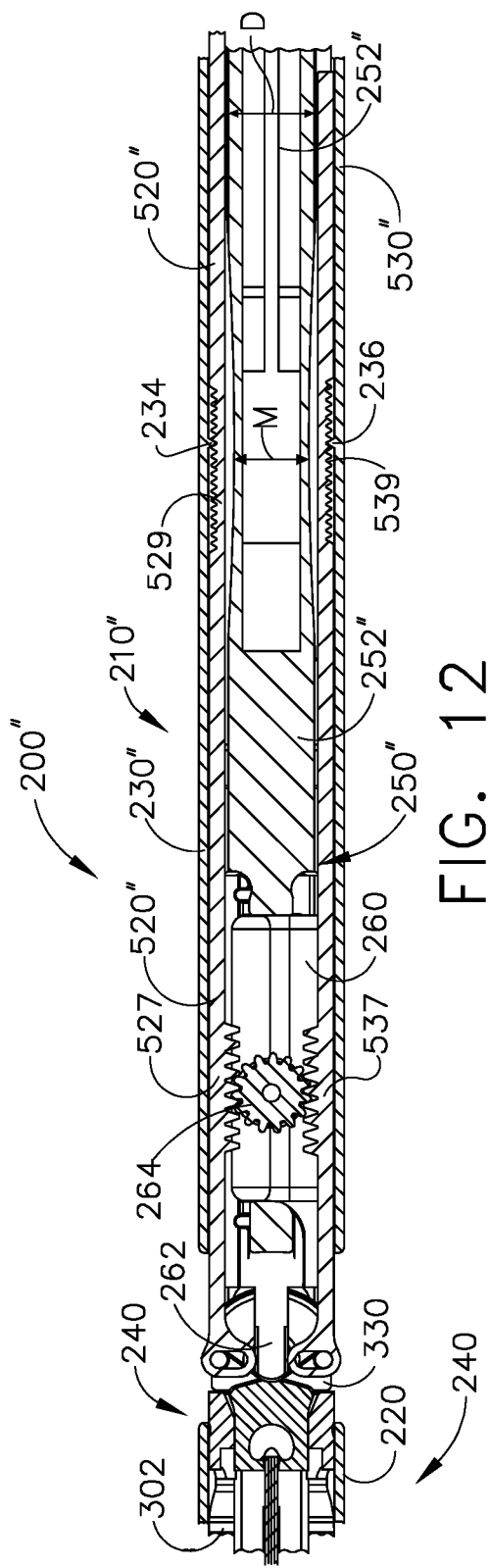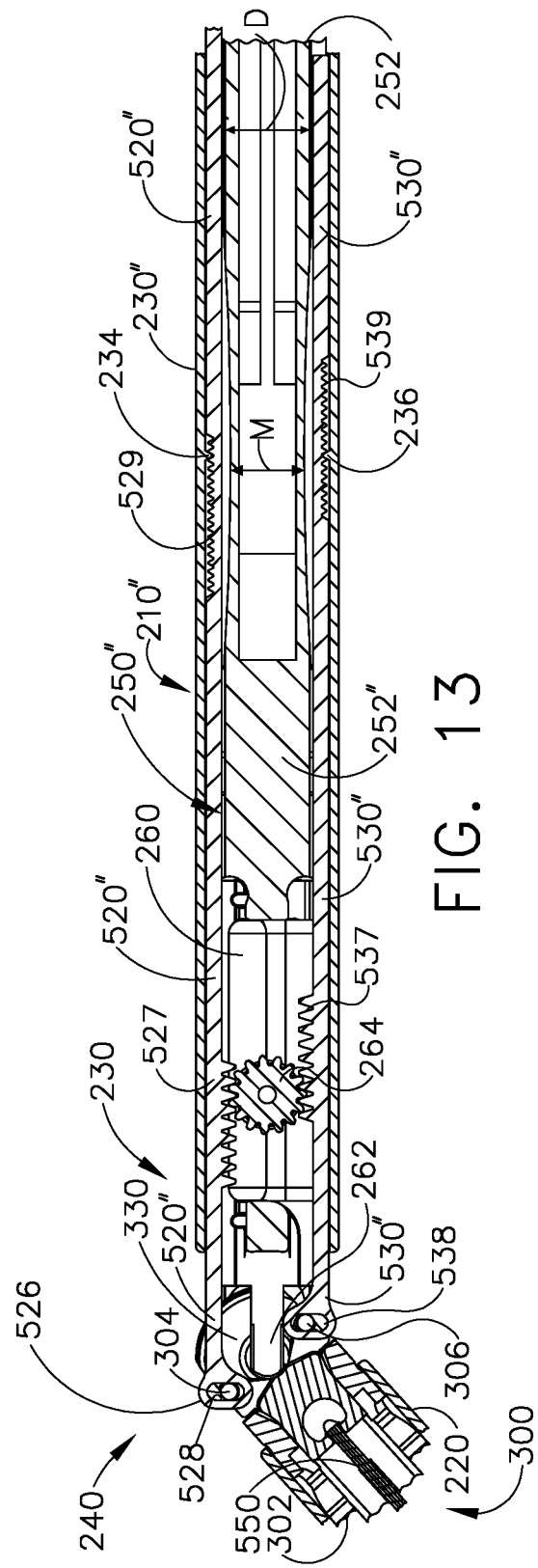

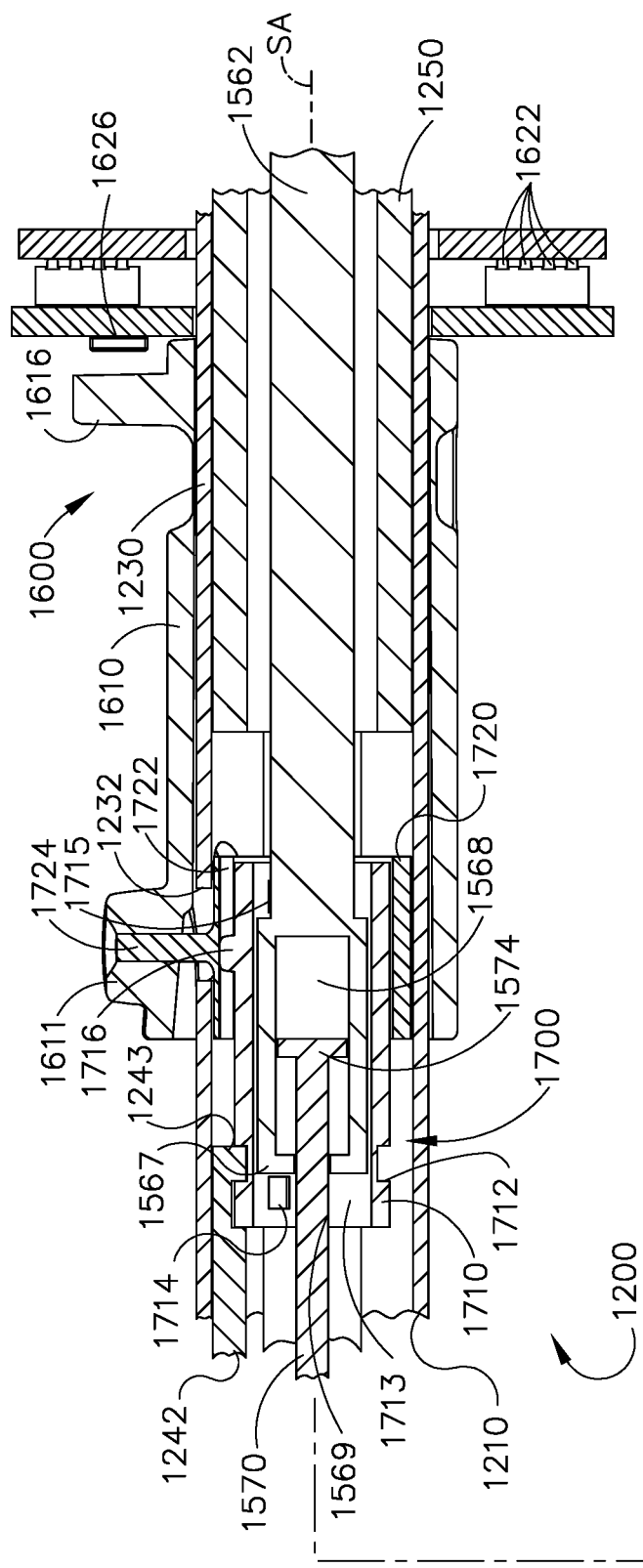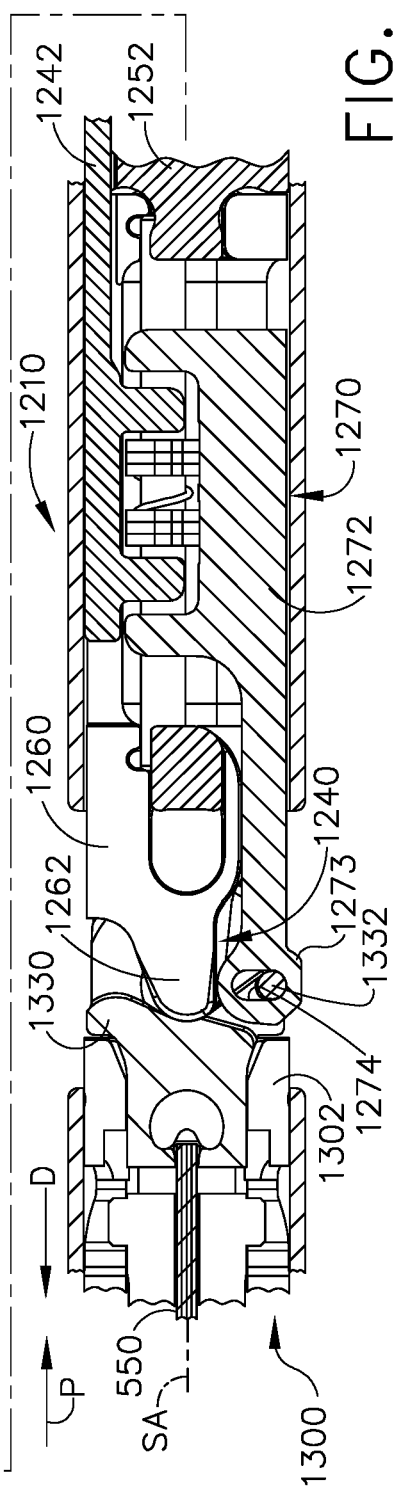
FIG. 20

LOCKING ARRANGEMENTS FOR DETACHABLE SHAFT ASSEMBLIES WITH ARTICULATABLE SURGICAL END EFFECTORS

CROSS-REFERENCE TO RELATED APPLICATIONS

The present application is a continuation patent application claiming priority under 35 U.S.C. § 120 to U.S. patent application Ser. No. 17/197,337, entitled LOCKING ARRANGEMENTS FOR DETACHABLE SHAFT ASSEMBLIES WITH ARTICULATABLE SURGICAL END EFFECTORS, filed Mar. 10, 2021, published as U.S. Patent Application Publication No. 2021/0267594 on Sep. 2, 2021, issued as U.S. Pat. No. 11,812,958 on Nov. 14, 2023, which is a continuation patent application claiming priority under 35 U.S.C. § 120 to U.S. patent application Ser. No. 16/021,321, entitled LOCKING ARRANGEMENTS FOR DETACHABLE SHAFT ASSEMBLIES WITH ARTICULATABLE SURGICAL END EFFECTORS, filed Jun. 28, 2018, which issued on Mar. 16, 2021 as U.S. Pat. No. 10,945,728, which is a continuation patent application claiming priority under 35 U.S.C. § 120 to U.S. patent application Ser. No. 14/575,148, entitled LOCKING ARRANGEMENTS FOR DETACHABLE SHAFT ASSEMBLIES WITH ARTICULATABLE SURGICAL END EFFECTORS, filed Dec. 18, 2014, which issued on Oct. 2, 2018 as U.S. Pat. No. 10,085,748, the entire disclosures of which are hereby incorporated by reference herein.

BACKGROUND

The present invention relates to surgical instruments and, in various embodiments, to surgical stapling and cutting instruments and staple cartridges for use therewith.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 12 is a partial cross-sectional view of a portion of another interchangeable shaft assembly in an unarticulated configuration;

FIG. 13 is a another partial cross-sectional view of the interchangeable shaft assembly of FIG. 12 in an articulated configuration;

FIG. 20 is another cross-sectional view of a portion of the interchangeable shaft assembly of FIGS. 14-19 with the end effector in an unarticulated orientation;

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

Figure 1:
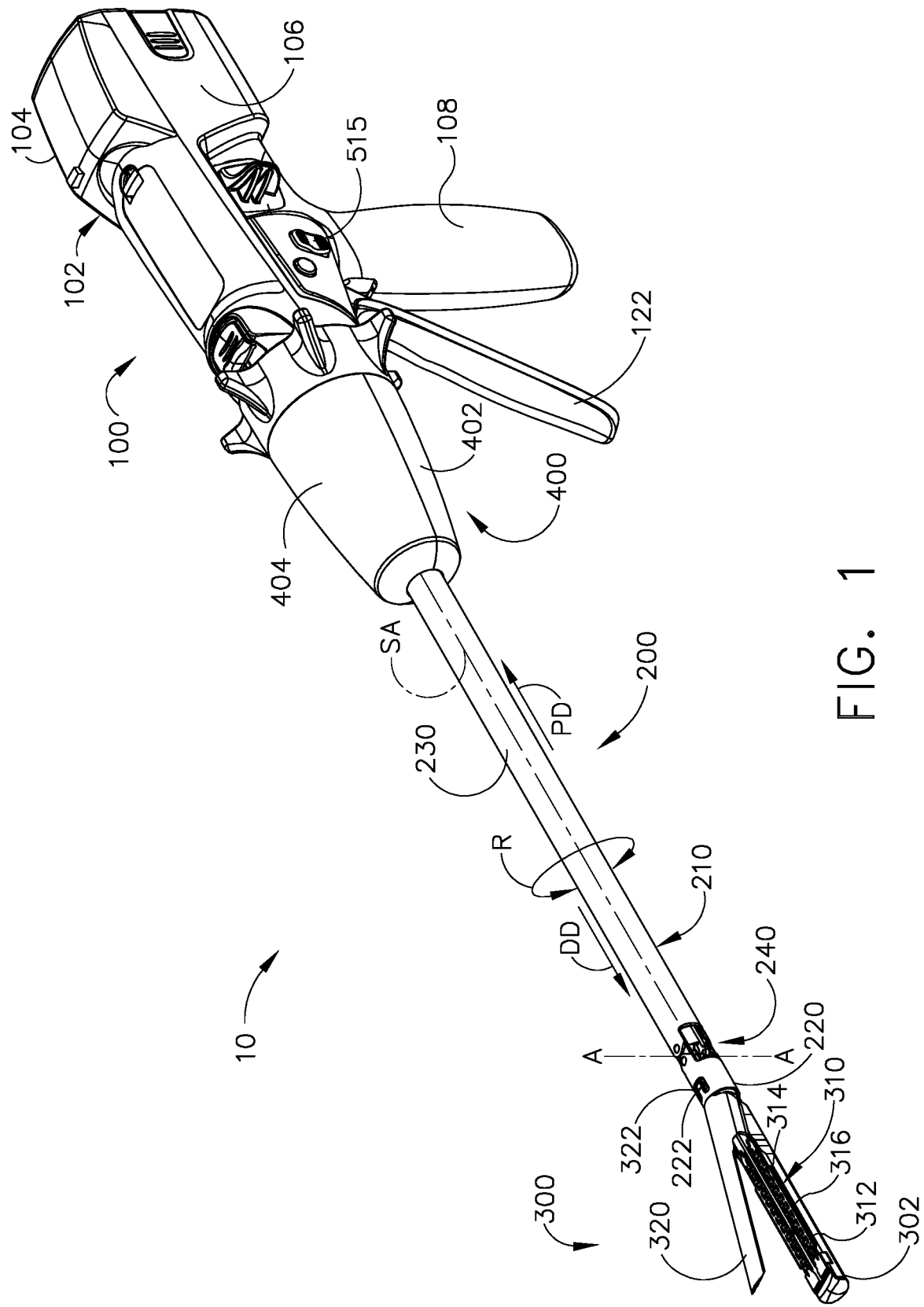
FIG. 1 is a perspective view of a powered surgical instrument comprising a handle, a shaft, and an articulatable end effector.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Pat. No. 10,470,762;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014 and which are each herein incorporated by reference in their respective entireties:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled USE OF POLARITY OF HALL MAGNET DETECTION TO DETECT MISLOADED CARTRIDGE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entireties:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Pat. No. 9,844,368;

U.S. patent application Ser. No. 14/248,588, entitled POWERED LINEAR SURGICAL STAPLER, now U.S. Pat. No. 10,405,857;

U.S. patent application Ser. No. 14/248,591, entitled TRANSMISSION ARRANGEMENT FOR A SURGICAL INSTRUMENT, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entireties:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Applicant of the present application owns the following patent applications that were filed on Dec. 18, 2014, which are each herein incorporated by reference in their respective entireties:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Pat. No. 10,188,385;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or "end effector" portions of the instruments can be inserted directly into a patient's body or can be inserted through an access device that has a working channel through which the end effector and elongated shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIG. 1 illustrates an exemplary motor driven (or "powered") surgical instrument which includes a housing 100, an elongate interchangeable shaft assembly 200 and a surgical end effector 300 that is operably connected to the interchangeable elongate shaft assembly 200. While the depicted shaft assembly is detachable from the housing 100, various unique and novel features may be equally enjoyed with arrangements that employ a dedicated (non-interchangeable) shaft assembly. The surgical end effector 300 as shown is configured to act as an endocutter for clamping, severing and stapling tissue. However, it will be appreciated that various embodiments may include end effectors configured to act as other surgical devices including, for example, graspers, cutters, staplers, clip appliers, access devices, drug/gene therapy delivery devices, ultrasound, RF, and/or laser energy devices, etc. As indicated above and will be describe further below, various portions of the surgical instrument 10 are motor driven. Further details regarding many aspects of the motor driven components of surgical instrument 10 may be found, for example, in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, now abandoned, which has been incorporated by reference in its entirety herein. However, it will be understood that the various arrangements and features disclosed herein may be effectively employed in connection with robotically-controlled surgical systems. For example, various arrangements disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, as well as in U.S. Pat. No. 6,132,368, entitled MULTI-COMPONENT TELEPRESENCE SYSTEM AND METHOD, U.S. Pat. No. 5,878,193, entitled AUTOMATED ENDOSCOPE SYSTEM FOR OPTIMAL POSITIONING, U.S. Pat. No. 5,792,135, entitled ARTICULATED SURGICAL INSTRUMENT FOR PERFORMING MINIMALLY INVASIVE SURGERY WITH ENHANCED DEXTERITY AND SENSITIVITY, U.S. Pat. No. 6,231,565, entitled ROBOTIC ARM DLUS FOR PERFORMING SURGICAL TASKS, U.S. Pat. No. 6,783,524, entitled ROBOTIC SURGICAL TOOL WITH ULTRASOUND CAUTERIZING AND CUTTING INSTRUMENT, U.S. Pat. No. 6,364,888, entitled ALIGNMENT OF MASTER AND SLAVE IN A MINIMALLY INVASIVE SURGICAL APPARATUS, U.S. Pat. No. 7,524,320, entitled MECHANICAL ACTUATOR INTERFACE SYSTEM FOR ROBOTIC SURGICAL TOOLS, U.S. Pat. No. 7,691,098, entitled PLATFORM LINK WRIST MECHANISM, U.S. Pat. No. 7,806,891, entitled REPOSITIONING AND REORIENTATION OF MASTER/SLAVE RELATIONSHIP IN MINIMALLY INVASIVE TELESURGERY, and U.S. Pat. No. 7,824,401, entitled ROBOTIC TOOL WITH WRISTED MONOPOLAR ELECTROSURGICAL END EFFECTORS the entire disclosures of each being hereby incorporated by reference herein.

Thus, as used herein, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. The term "frame" may refer to a portion of a handheld surgical instrument, e.g., a "handle". The term "frame" may also represent a portion of a robotically-controlled surgical instrument and/or a portion of the robotic system that may be used to operably control a surgical instrument.

It should be appreciated that spatial terms such as vertical, horizontal, right, left, etc. are given herein with reference to the Figures assuming that the longitudinal or "shaft axis" of the surgical instrument 10 is co-axial to the central axis of the shaft 200. In actual practice, however, the surgical instrument 10 may be oriented at various angles and as such these spatial terms are used relative to the surgical instrument itself. Further, for a hand-held housing, "proximal" is used to denote a perspective of a clinician who is behind the handle who places the end effector 300 distal, or away from him or herself. As used herein, the phrase, "substantially transverse to the longitudinal axis" where the "longitudinal axis" is the axis of the shaft, refers to a direction that is nearly perpendicular to the longitudinal axis. It will be appreciated, however, that directions that deviate some from perpendicular to the longitudinal axis are also substantially transverse to the longitudinal axis.

As can be seen in FIG. 1, the end effector 300 is pivotally connected to the shaft assembly 200 at articulation joint 240. A variety of articulation joints and control systems are disclosed in various patents and patent applications that have been incorporated by reference herein and may be employed in connection with various features disclosed and claimed herein. Other articulation joints and articulation systems are disclosed in U.S. Pat. No. 7,753,245, entitled SURGICAL STAPLING INSTRUMENTS and U.S. Pat. No. 7,670,334, entitled SURGICAL INSTRUMENT HAVING AN ARTICULATING END EFFECTOR, the entire disclosures of each being hereby incorporated by reference herein. Various other means for articulating the end effector 300 are discussed in greater detail below.

The illustrated end effector 300 includes an elongate channel 302 that is configured to operably support a surgical staple cartridge 310 therein. The staple cartridge 310 includes a cartridge body 312 that operably supports a plurality of surgical staples or fasteners (not shown) therein. In one implementation, the staples are operably supported on drivers that are movably supported within corresponding staple pockets 314 formed in the cartridge body 312. The cartridge body 312 further includes an elongate slot 316 that is centrally disposed between lines of staple pockets 314. The elongate slot 316 is configured to accommodate a tissue cutting member (not shown) that is supported for longitudinal travel through the cartridge body 312 upon application of a firing motion thereto from a firing system as will be discussed in further detail below. In certain implementations, the tissue cutting member may interface with an actuator member, sometimes referred to as a "wedge sled" or simply "sled" that is configured to apply an upward motion to the staple drivers as the wedge sled is driven distally with the tissue cutting member. As can also be seen in FIG. 1, the end effector 300 includes an anvil 320 that is movably supported on the elongate channel 302 for selective travel toward and away from the elongate channel 302 and the staple cartridge 310 supported therein. The elongate channel and the anvil may also be referred to as "jaws" that are movable between open and closed positions. The anvil 320 has a staple-forming undersurface (not shown) that serves to form the ends of the staples as they are driven into forming contact therewith. The anvil 320 is movable between an open and closed positions by a closure member assembly 210 that interfaces with a closure system that is operably supported by the housing 100 as will be discussed in further detail below. In the illustrated embodiment, the anvil 320 is moved toward the staple cartridge 310 to a closed position when the closure member assembly 210 is driven in the distal direction "DD" and returned to an open position when the closure member assembly 210 is moved in a proximal direction "PD". A variety of different end effector arrangements and constructions are known and may be employed with various unique and novel features disclosed herein. Thus, many of the claims presented herein may not be limited to the particular end effector arrangement depicted in FIG. 1, for example. More details concerning the specific construction and operation of alternative end effectors may be found in various U.S. patent applications and patents that have been incorporated by reference herein.

In the illustrated form, the surgical instrument 10 includes a housing 100 that comprises a handle 102. In at least one form, the handle 102 comprises a pair of interconnectable housing segments 104, 106 that are interconnected by screws, snap features, adhesive, etc. In the illustrated arrangement, the handle housing segments 104, 106 cooperate to form a pistol grip portion 108 that can be gripped and manipulated by the clinician. As will be discussed in further detail below, the handle 102 operably supports a plurality of drive systems therein that are configured to generate and apply various control motions to corresponding portions of the interchangeable shaft assembly that is operably attached thereto.

Figure 2:
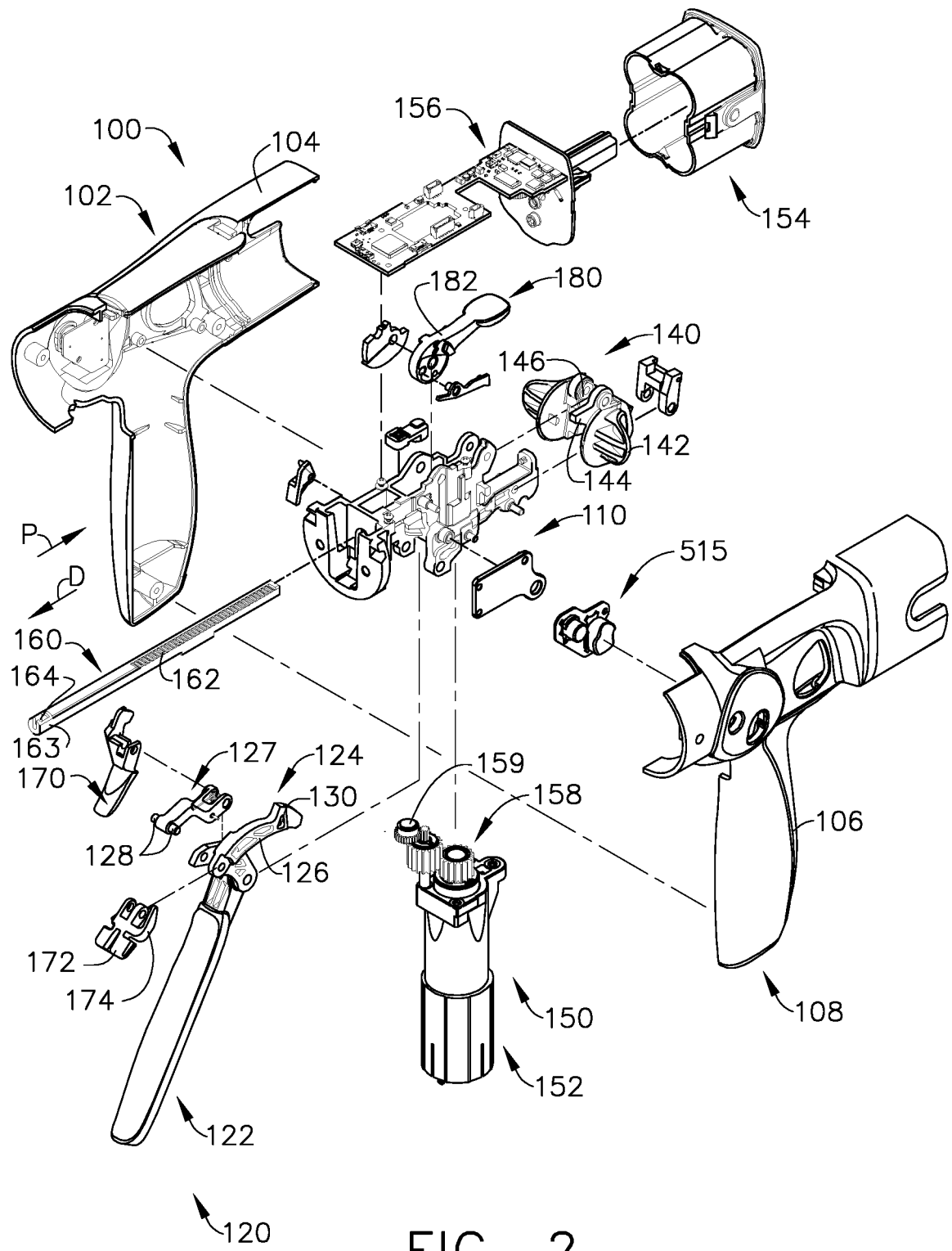
FIG. 2 is an exploded assembly view of a surgical instrument housing.

Referring now to FIG. 2, the handle 102 may further include a frame 110 that operably supports a plurality of drive systems. For example, the frame 110 can operably support a first or closure drive system, generally designated as 120, which may be employed to apply closing and opening motions to the interchangeable shaft assembly 200 that is operably attached or coupled thereto. In at least one form, the closure drive system 120 may include an actuator in the form of a closure trigger 122 that is pivotally supported by the frame 110. More specifically, as illustrated in FIG. 2, the closure trigger 122 may be pivotally supported by frame 110 such that when the clinician grips the pistol grip portion 108 of the handle 102, the closure trigger 122 may be easily pivoted from a starting or unactuated position to an actuated position and more particularly to a fully compressed or fully actuated position. The closure trigger 122 may be biased into the unactuated position by spring or other biasing arrangement (not shown). In various forms, the closure drive system 120 further includes a closure linkage assembly 124 that is pivotally coupled to the closure trigger 122. As can be seen in FIG. 2, the closure linkage assembly 124 may include a closure link 126 that that is pivotally coupled to the closure trigger 122. In addition, the closure linkage assembly 124 includes another closure link 127 that has a pair of laterally extending attachment lugs or portions 128 protruding therefrom.

Still referring to FIG. 2, it can be observed that the closure link 126 may have a locking wall 130 thereon that is configured to cooperate with a closure release assembly 140 that is pivotally coupled to the frame 110. In at least one form, the closure release assembly 140 may comprise a release button assembly 142 that has a distally protruding cam follower arm 144 formed thereon. The release button assembly 142 may be pivoted in a counterclockwise direction by a release spring 146. As the clinician depresses the closure trigger 122 from its unactuated position towards the pistol grip portion 108 of the handle 102, the closure link 126 pivots upward to a point wherein the cam follower arm 144 drops into retaining engagement with the locking wall 130 on the closure link 126 thereby preventing the closure trigger 122 from returning to the unactuated position. Thus, the closure release assembly 140 serves to lock the closure trigger 122 in the fully actuated position. When the clinician desires to unlock the closure trigger 122 to permit it to be biased to the unactuated position, the clinician simply pivots the closure release button assembly 142 such that the cam follower arm 144 is moved out of engagement with the locking wall 130 on the closure link 126. When the cam follower arm 144 has been moved out of engagement with the closure link 126, the closure trigger 122 may pivot back to the unactuated position. Other closure trigger locking and release arrangements may also be employed.

In at least one form, the handle 102 and the frame 110 may operably support another drive system referred to herein as firing drive system 150 that is configured to apply firing motions to corresponding portions of the interchangeable shaft assembly 200 attached thereto. The firing drive system may also be referred to herein as a "second drive system". The firing drive system 150 may employ an electric motor ("firing motor") 152, located in the pistol grip portion 108 of the handle 102. In various forms, the firing motor 152 may be a DC brushed driving motor having a maximum rotation of, approximately, 25,000 RPM, for example. In other arrangements, the firing motor may include a brushless motor, a cordless motor, a synchronous motor, a stepper motor, or any other suitable electric motor. A battery 154 (or "power source" or "power pack"), such as a Li ion battery, for example, may be coupled to the handle 102 to supply power to a control circuit board assembly 156 and ultimately to the firing motor 152.

The firing motor 152 can include a rotatable shaft (not shown) that operably interfaces with a gear reducer assembly 158 that is mounted in meshing engagement with a with a set, or rack, of drive teeth 162 on a longitudinally-movable drive member 160. In use, a voltage polarity provided by the battery can operate the firing motor 152 in a clockwise direction wherein the voltage polarity applied to the electric motor by the battery can be reversed in order to operate the electric motor 152 in a counter-clockwise direction. When the electric motor 152 is rotated in one direction, the drive member 160 will be axially driven in the distal direction "DD". When the motor 152 is driven in the opposite rotary direction, the drive member 160 will be axially driven in a proximal direction "PD". The handle 102 can include a switch which can be configured to reverse the polarity applied to the firing motor 152 by the battery. As with the other forms described herein, the handle 102 can also include a sensor or sensors that are configured to detect the position(s) of the drive member 160 and/or the direction(s) in which the drive member 160 is being moved.

In the illustrated instrument, actuation of the firing motor 152 is controlled by a firing trigger 170 that is pivotally supported on the handle 102. The firing trigger 170 may be pivoted between an unactuated position and an actuated position. The firing trigger 170 may be biased into the unactuated position by a spring (not shown) or other biasing arrangement such that when the clinician releases the firing trigger 170, it may be pivoted or otherwise returned to the unactuated position by the spring or biasing arrangement. In the illustrated form, the firing trigger 170 is positioned "outboard" of the closure trigger 122 as was discussed above. In at least one form, a firing trigger safety button 172 is pivotally mounted to the closure trigger 122. The safety button 172 is positioned between the firing trigger 170 and the closure trigger 122 and has a pivot arm 174 protruding therefrom. When the closure trigger 122 is in the unactuated position, the safety button 172 is contained in the handle housing 100 where the clinician cannot readily access it and move it between a safety position preventing actuation of the firing trigger 170 and a firing position wherein the firing trigger 170 may be fired. As the clinician depresses the closure trigger 122, the safety button 172 and the firing trigger 170 pivot down wherein they can then be manipulated by the clinician.

As indicated above, in at least one form, the longitudinally movable drive member 160 has a rack of teeth 162 formed thereon for meshing engagement with a corresponding drive gear 159 of the gear reducer assembly 158. At least one form may also include a manually-actuatable "bailout" assembly 180 that is configured to enable the clinician to manually retract the longitudinally movable drive member 160 should the firing motor 152 become disabled. The bailout assembly 180 may include a lever or bailout handle assembly 182 that is configured to be manually pivoted into ratcheting engagement with the teeth 162 in the drive member 160. Thus, the clinician can manually retract the drive member 160 by using the bailout handle assembly 182 to ratchet the drive member in the proximal direction "PD". U.S. Patent Application Publication No. 2010/0089970, now U.S. Pat. No. 8,608,045, discloses bailout arrangements and other components, arrangements and systems that may also be employed with the various instruments disclosed herein. U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045, is hereby incorporated by reference in its entirety herein.

FIG. 1 illustrates the surgical instrument 10 with an interchangeable shaft assembly 200 operably coupled thereto. As indicated above, the shaft assembly 200 may be configured for quick attachment and detachment to the housing 100. The closure member assembly 210 includes a distal closure member segment 220 that is pivotally attached to a proximal closure member segment 230 at the articulation joint 240. The distal closure member segment 220 includes a U-shaped opening 222 that is configured to operably engage an upstanding anvil tab 322 on the anvil 320 when the closure member assembly is drawn in the proximal direction "PD". When the U-shaped opening 222 engages the anvil tab 322, the anvil 320 is pivoted to an open position. Specific details regarding examples of the articulation joint 240 and or other suitable articulation joint arrangements may be found in the various documents that have been herein incorporated by reference.

Figure 3:
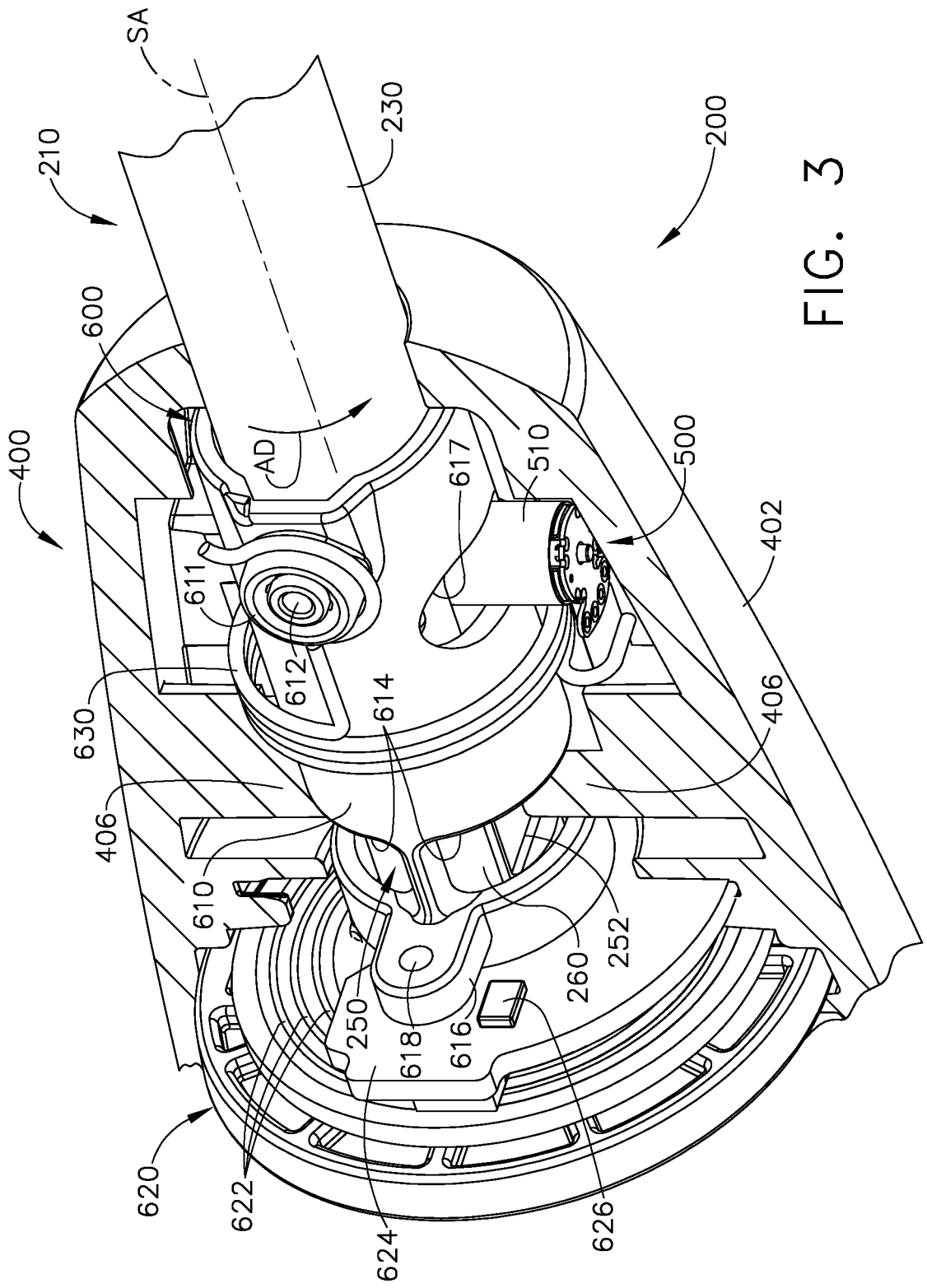
FIG. 3 is a cross-sectional view of a portion of an interchangeable shaft assembly.
Figure 7:
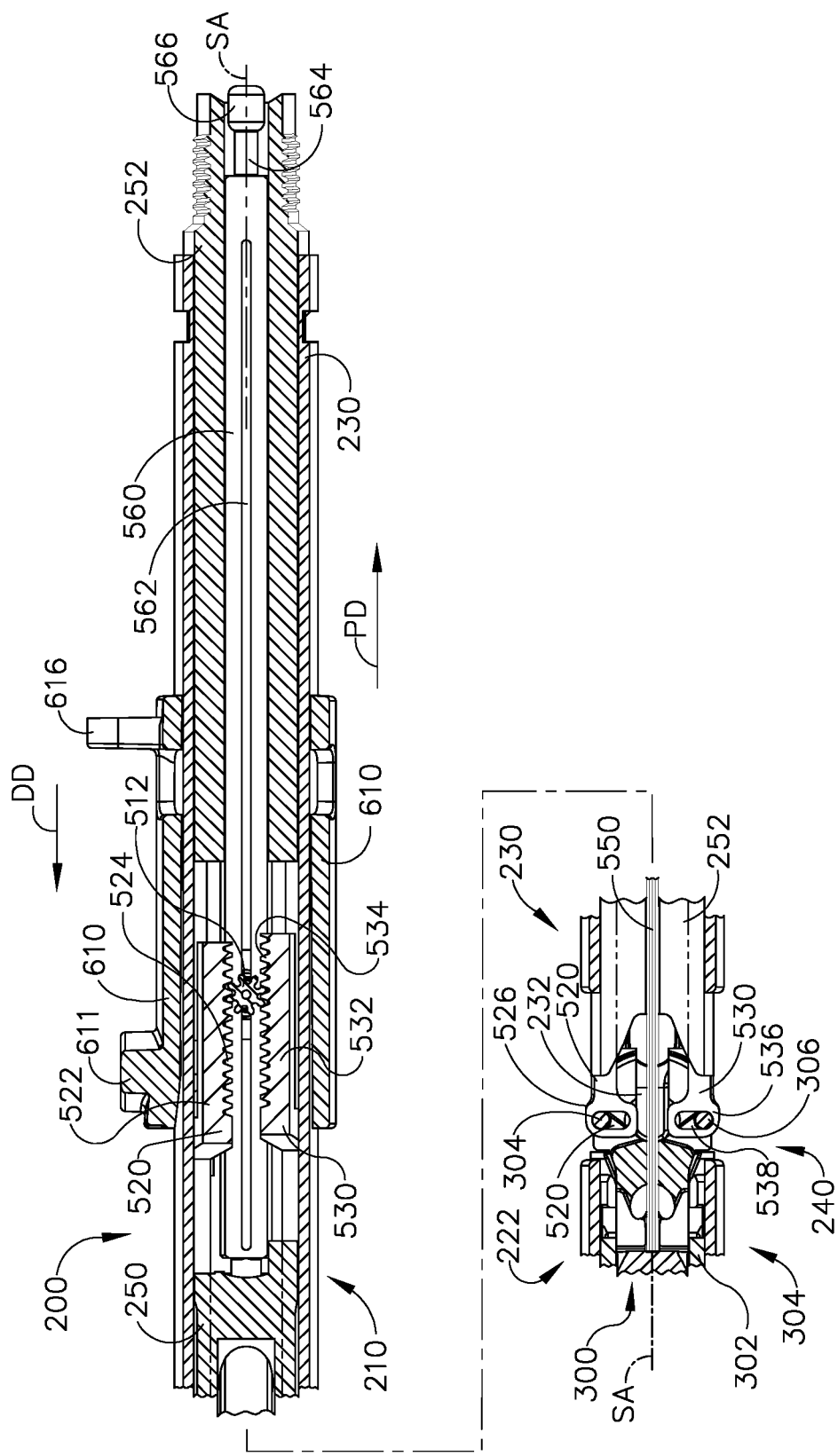
FIG. 7 is another cross-sectional view of the interchangeable shaft assembly and portion of the surgical end effector with the end effector in an unarticulated orientation.
Figure 8:
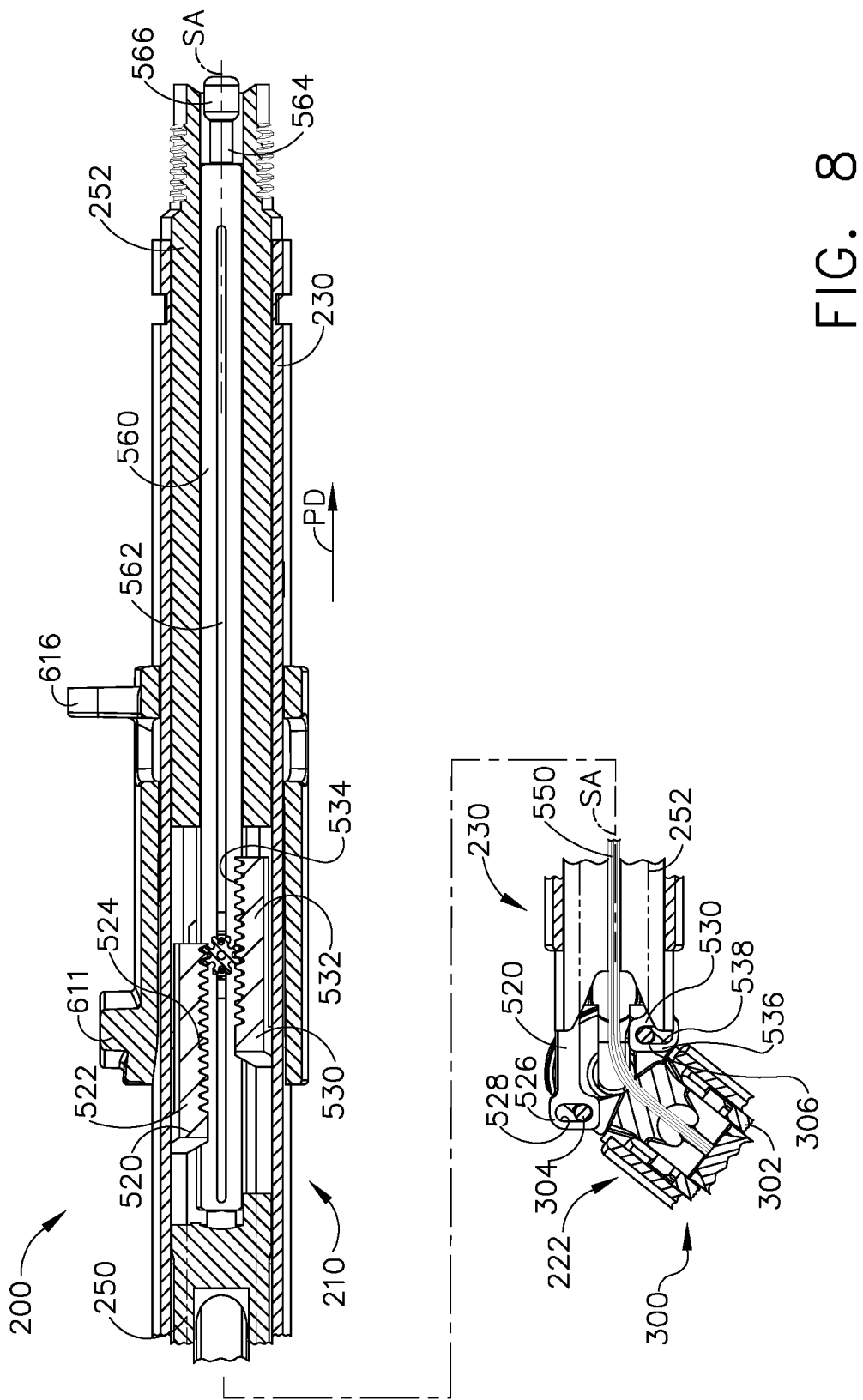
FIG. 8 is another cross-sectional view of the interchangeable shaft assembly of FIG. 7 with the end effector in an articulated orientation.

Referring now to FIGS. 3 and 7, the shaft assembly 200 includes a spine assembly 250 upon which the closure member assembly 210 is movably supported. The spine assembly 250 includes a distal end 252 that is pivotally attached to a proximal end 304 of the elongate channel 302. See FIG. 7. Such arrangement facilitates pivotal articulation of the end effector 300 relative to the distal end 252 of the spine assembly 250 about an articulation axis A-A which is transverse to the shaft axis SA-SA. See FIG. 1. In various implementations, the end effector 300 may also be selectively rotatable relative to the housing 100 about the shaft axis SA-SA (represented by arrow "R" in FIG. 1). Because the end effector 300 is directly attached to the distal end 252 of the spine assembly 250, rotation of the spine assembly 250 relative to the housing 100 results in rotation of the end effector 300 as well. In the illustrated implementation, the interchangeable shaft assembly 200 includes a rotation nozzle 400 that is rotatably journaled or otherwise rotationally supported by the handle 102. In the illustrated implementation, for example, the rotation nozzle 400 comprises two nozzle portions 402, 404 that are coupled together by snap features, screws, adhesive, etc. and include two opposed, inwardly extending lugs 406 that are seated in corresponding notches 254 in the proximal end 252 of the spine assembly 250. See FIG. 3. Such arrangement facilitates rotation of the spine assembly 250 when the nozzle 400 is rotated.

Figure 5:
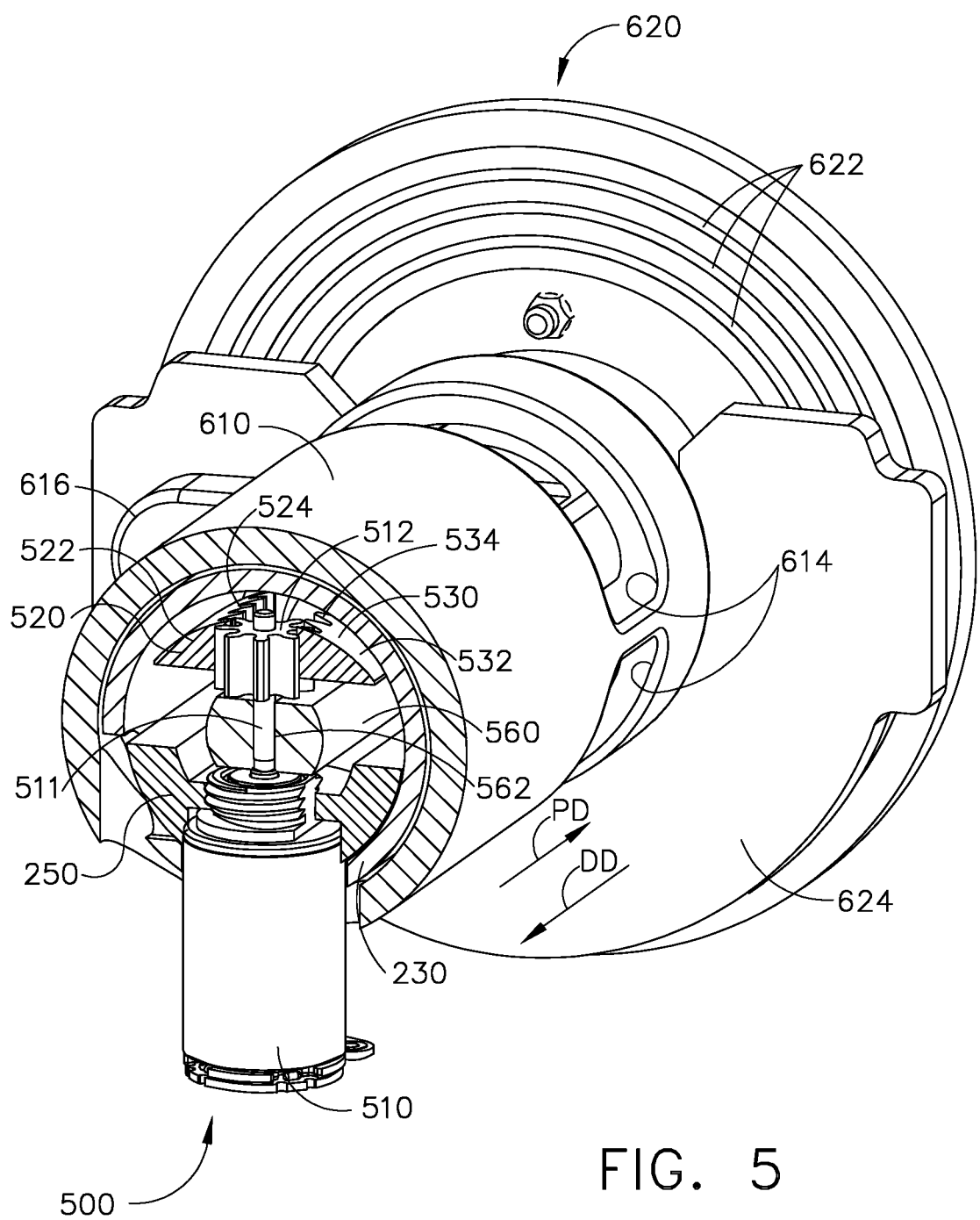
FIG. 5 is a cross-sectional perspective view of the interchangeable shaft assembly of FIG. 4.
Figure 6:
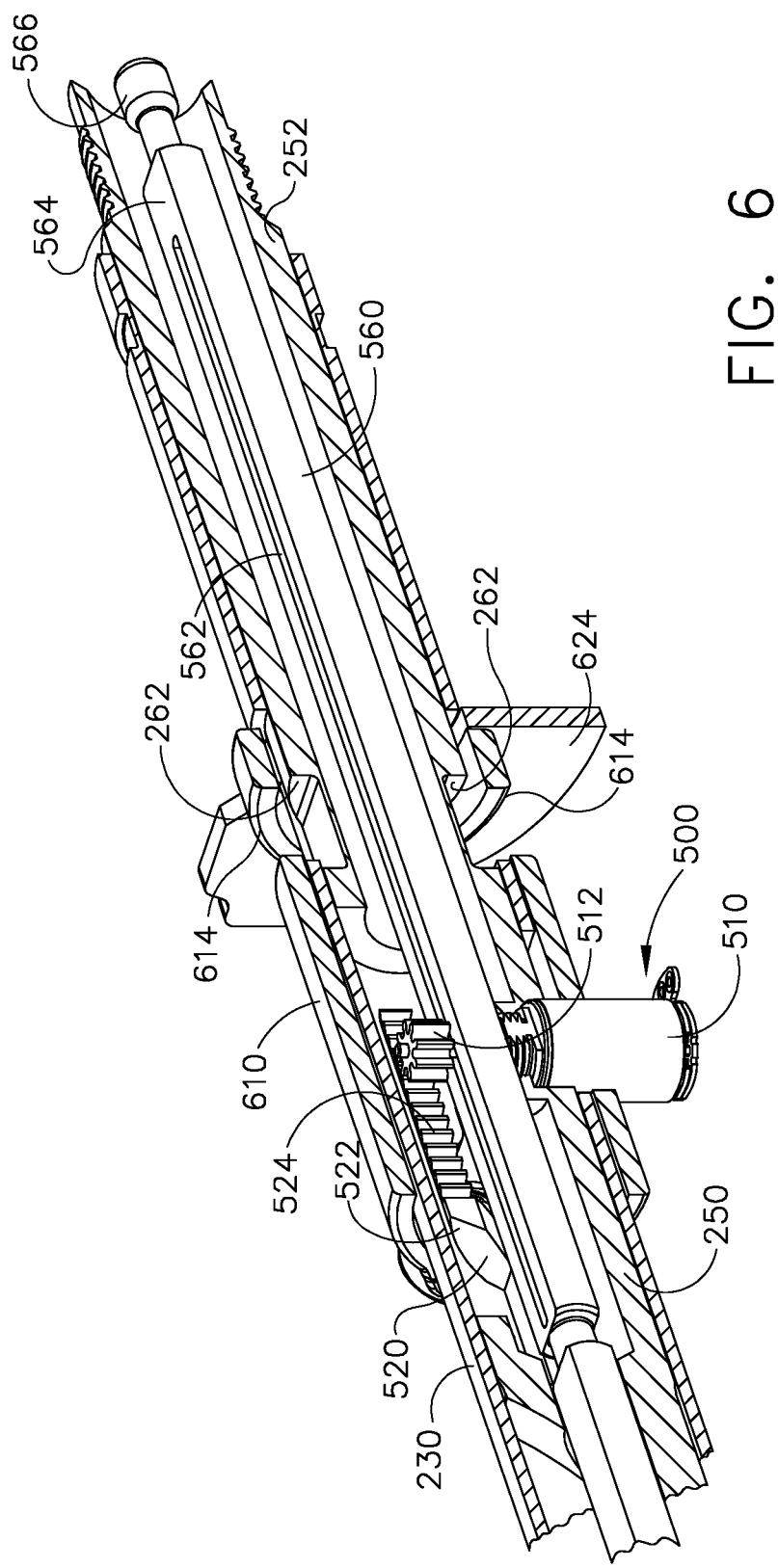
FIG. 6 is a cross-sectional perspective view of a portion of the interchangeable shaft assembly of FIG. 5.

Articulation of the end effector 300 about the articulation axis A-A is accomplished by actuation of an articulation system 500. In the illustrated implementation, for example, the articulation system 500 includes an articulation motor 510 that is used to actuate first and second articulation drivers 520, 530. See FIGS. 5 and 6. The articulation motor 510 may comprise a motor similar to the firing motor or any one of the various motor configurations discussed herein and includes an articulation drive gear 512 that is in meshing engagement with a first gear rack 524 on the proximal end 522 of the first articulation driver 520. The articulation gear 512 is also in meshing engagement with a second gear rack 534 on the proximal end 532 of the second articulation driver 530. As can be most particularly seen in FIG. 5, the articulation gear 512 is centrally disposed between the first and second gear racks 524, 534 such that rotation of the articulation gear in a first direction will result in the axial movement of the first articulation driver 520 in a distal direction "DD" and the simultaneous axial movement of the second articulation driver 530 in the proximal "PD" or opposite axial direction. Likewise, rotation of the articulation gear 512 in a second rotary direction will result in the axial movement of the second articulation driver 530 in the distal direction "DD" and the simultaneous axial movement of the first articulation driver 520 in the proximal or opposite direction "PD". Referring to FIG. 7, the distal end 526 of the first articulation driver 520 includes a slot 528 that is configured to receive a corresponding pin 304 formed on the elongate channel 302. Likewise, the distal end 536 of the second articulation driver 530 includes a slot 538 that is configured to receive a corresponding pin 306 formed on the elongate channel 302. Thus, axial movement of the articulation drivers 520, 530 in the above described manner will applying simultaneous "pushing and pulling" motions to the elongate channel 302 and thereby result in pivotal articulation of the end effector 300 about the articulation axis A-A.

As indicated above, the surgical instrument 10 also includes a tissue cutting member that is configured for axial travel through the elongate slot 316 in the surgical staple cartridge 310. In the illustrated implementation, for example, the tissue cutting member or tissue cutting surface (not shown) is formed on or otherwise attached to a distal firing member 550. The distal firing member 550 may be of laminated construction to facilitate bending about the articulation axis A-A while remaining sufficiently rigid to enable the tissue cutting edge to be driven through tissue that is clamped between the surgical staple cartridge and the anvil as well as driving the wedge sled therethrough. Various distal firing member and tissue cutting member configurations are known and are disclosed in the patents and/or patent applications that have been herein incorporated by reference. The distal firing member 550 is attached to a proximal firing member 560 that is supported for axial travel relative to the spine assembly 250. The proximal firing member 560 has a centrally disposed axial slot 562 therein to accommodate the drive shaft 511 of the articulation motor 510. See FIG. Such arrangement facilitates axial travel of the proximal firing member 560 in response to firing motions applied thereto by the firing system. The proximal end 564 of the proximal firing member 560 includes a lug 566 that is configured to be receive in a firing rod attachment cradle 164 provided in the distal end 162 of the movable drive member 160. See FIG. 2. Thus, actuation of the firing motor 152 will result in the axial movement of the movable drive member 160 and the proximal firing member 560 and the distal firing member 550.

The firing motor 152 and the articulation motor 510 communicate with the control circuit 156 (FIG. 2) and are interlocked by a switching arrangement generally designated as 600. In the illustrated configuration, the switching arrangement 600 includes a switch drum 610 that is rotatably supported on the proximal closure member segment 230. See FIG. 3. The switch drum 610 includes a laterally extending boss 611 that has an inwardly extending cam pin 612 mounted (press-fit) therein. The cam pin 612 extends inwardly into a cam slot 232 provided in the proximal closure member segment 230. See FIG. 4. The switch drum 610 further includes opposed slots 614 that are configured to accommodate rotation of the nozzle lugs 406 therethrough. An articulation slot 617 is also provided to facilitate rotation of the switch drum 610 relative to the articulation motor 510. See FIG. 3. The switching arrangement 600 also includes a slip ring assembly 620 which is configured to conduct electrical power and/or signals to and/or from the end effector 300 to the handle 102 and more particularly to the control circuit 156 within the handle 102. The slip ring assembly 620 includes a plurality of concentric, or at least substantially concentric, conductors 622 on opposing sides thereof which can be configured to permit relative rotation between the halves of the slip ring assembly 620 while still maintaining electrically conductive pathways therebetween. Examples of such slip ring assemblies are disclosed U.S. patent application Ser. No. 13/800,067, entitled STAPLE CARTRIDGE TISSUE THICKNESS SENSOR SYSTEM, now U.S. Patent Application Publication No. 2014/0263552, now abandoned, and U.S. patent application Ser. No. 13/800,025, entitled STAPLE CARTRIDGE TISSUE THICKNESS SENSOR SYSTEM, now U.S. Pat. No. 9,345,481, and which are each hereby incorporated by reference herein in their respective entireties. In the illustrated implementation, the slip ring assembly 620 includes a bulkhead 624 that has a switch component 626 that communicates through the slip ring assembly 620 to the control circuit 156. The switch arrangement 600 also includes a movable switch component 618 that is mounted to a switch arm portion 616 of the switch drum 610.

Figure 4:
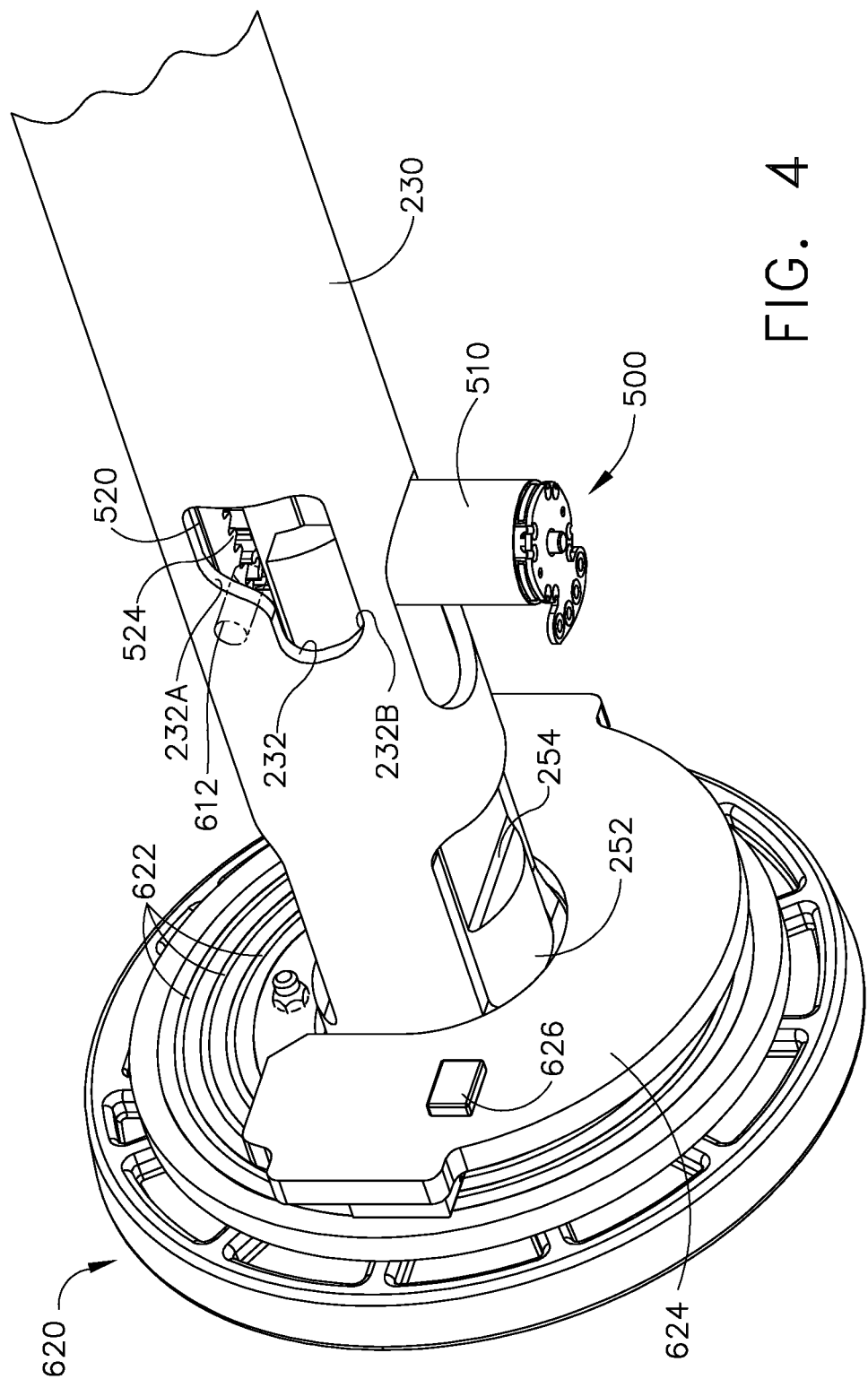
FIG. 4 is a partial perspective view of a portion of the interchangeable shaft assembly of FIG. 3 with the lock drum and nozzle removed for clarity.

Referring to FIG. 4, it can be seen that the cam slot 232 has a first portion 232A and a second portion 232B. When the closure member 230 is in the proximal (unactuated) position, the cam pin 612 is in the first portion 232A of the cam slot 232. A lock out spring 630 is mounted on the switch drum boss 611 to bias the switch drum 610 into that first position wherein the cam pin 612 is in the first portion 232A of the cam slot 232. See FIG. 3. When in that first position, the movable switch component 618 is not in contact or in "actuation proximity" with switch component 626. When in this "firing lock" position, the control circuit prevents actuation of the firing motor 152. Stated another way, unless the movable switch component 618 actuates switch component 626, no power is supplied to the firing motor 152. Thus, even if the clinician were to actuate the firing trigger 170 in an attempt to actuate the firing motor 152, the firing motor 152 would not actuate.

During a typical surgical procedure, the clinician may introduce the end effector 300 into the surgical site through a trocar or other opening in the patient to access the target tissue. In an effort to position the end effector in a desired position relative to the target tissue, the clinician may actuate the articulation motor 510 by actuating a rocker switch 515 mounted on the handle 102. The rocker switch 515 communicates with the control circuit 156 and by rocking the rocker switch 515 in a first direction will cause the articulation motor 510 to rotate in a first direction and result in articulation of the end effector 300 in a first articulation direction. Rocking the switch 515 in a second direction will result in rotation of the articulation motor 510 in an opposite rotary direction and cause the end effector 300 to articulate in a second opposite articulation direction. Once the clinician has positioned the end effector 300 in a desired position, the clinician can release the switch 515 to stop the articulation. At this point, the target tissue may be positioned between the surgical staple cartridge 310 and the anvil 320. The clinician may then move the anvil 320 to a closed position wherein the target tissue is clamped between the staple cartridge 310 and the anvil 320.

The closure member assembly 210 is actuated by actuating the closure trigger 122. The proximal end of the proximal closure member segment 230 is supported in a closure member attachment yoke (not shown) that is movably supported in a frame portion (not shown) of the shaft assembly 200. Examples of the closure member attachment yoke and the frame portion of the shaft assembly are described in further detail in U.S. patent application Ser. No. 13/803,097, entitled ARTICULATABLE SURGICAL INSTRUMENT COMPRISING A FIRING DRIVE, now U.S. Pat. No. 9,687,230, which has been herein incorporated by reference in its entirety. As the clinician depresses the closure trigger 122, the closure member assembly 210 is moved in the distal direction "DD" which ultimately causes the anvil 320 to pivot to the clamped position onto the target tissue. As the closure member assembly 210 moves distally, the cam pin 612 interacts with the cam slot 232 and is cammed into portion 232B of the cam slot 232. Movement of the cam pin 612 into the portion 232B of the cam slot 232 results in the rotational movement of the switch drum assembly 610 in actuation direction (represented by arrow "AD" in FIG. 3). As the switch drum 610 is biased into the actuation direction "AD" against the force of the spring 630, the switch component 618 is brought into activation/registration with switch component 626 which causes the control circuit board 156 to permit power to flow to the firing motor 152 upon actuation of the firing trigger 170. When in that closed position, the closure member assembly 210 and the anvil 320 are locked in the closed position in the manner described above. The control circuit 156 may also be configured such that when the switch components 618 and 626 are in actuation registration, the control circuit 156 prevents any flow of power to the articulation motor 510 should the rocker switch 515 be inadvertently actuated. Once the closure member assembly 210 and anvil 320 are locked in clamped position, the clinician may actuate the firing trigger 170 to drive the cutting member through the end effector 300 and cut the target tissue clamped therein and fire the surgical fasteners on each side of the tissue cut line. The end effector 300 may also be equipped with sensors that communicate with the control circuit 156 to detect when the tissue cutting member has reached its distal-most position to thereby signal the firing motor 152 to stop and reverse its direction to retract the tissue cutting member to its starting position. Other sensors may be employed to detect when the tissue cutting member has returned to the starting position and communicate with the control circuit 156 to thereby provide the clinician with an indication of the status of the tissue cutting member and/or enable the closure member assembly to be unlocked. Once the closure member assembly 210 has been unlocked, the lock out spring 630, acting on the switch drum 610, will urge the cam pin 612 to rotatably return to the portion 232A of the cam slot 232. Rotation of the switch drum 610 back to that starting position will deactivate the switch 626 which will once again prevent actuation of the firing motor 152.

Figure 9:
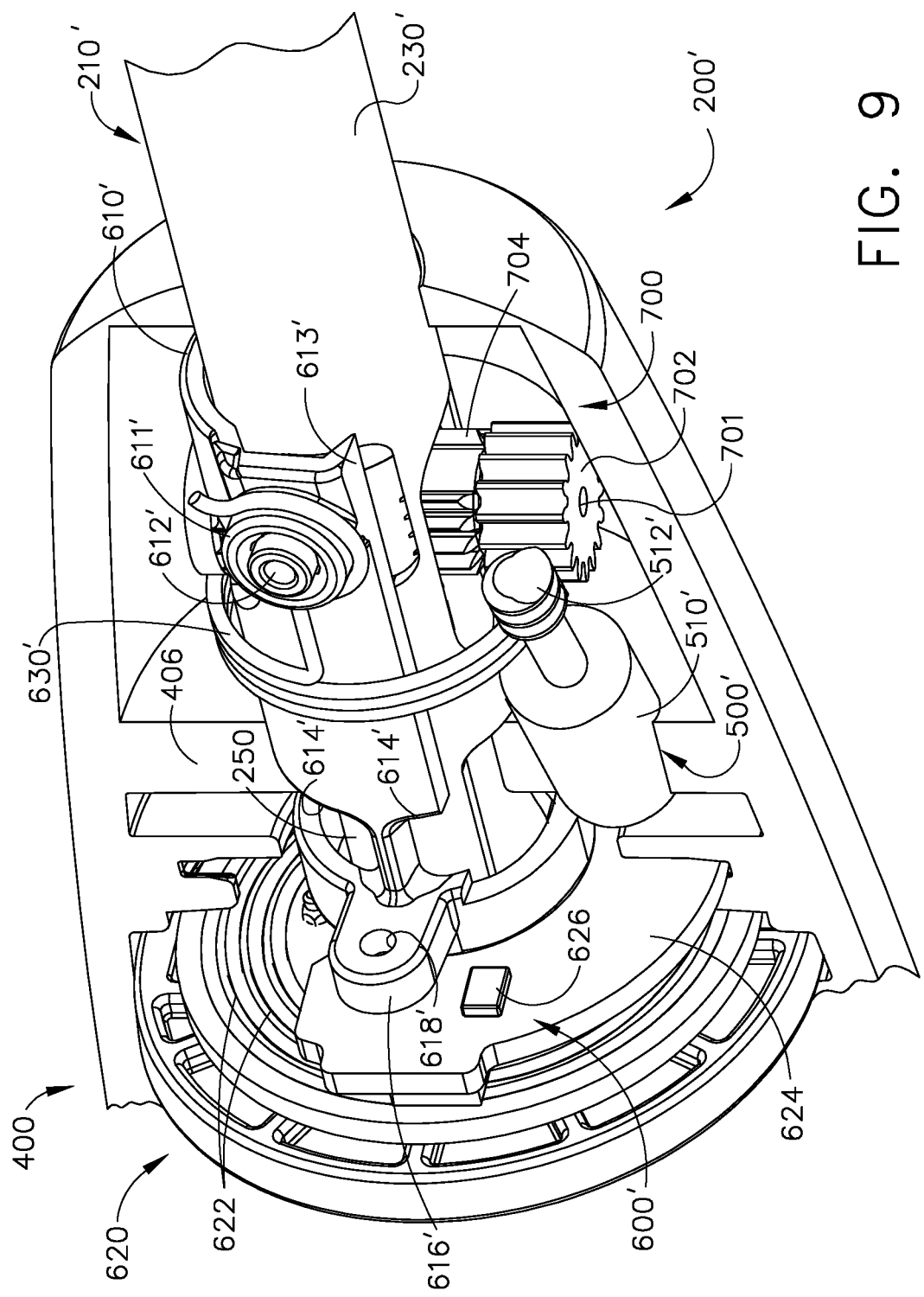
FIG. 9 is a partial perspective view of a portion of another interchangeable shaft assembly.
Figure 10:
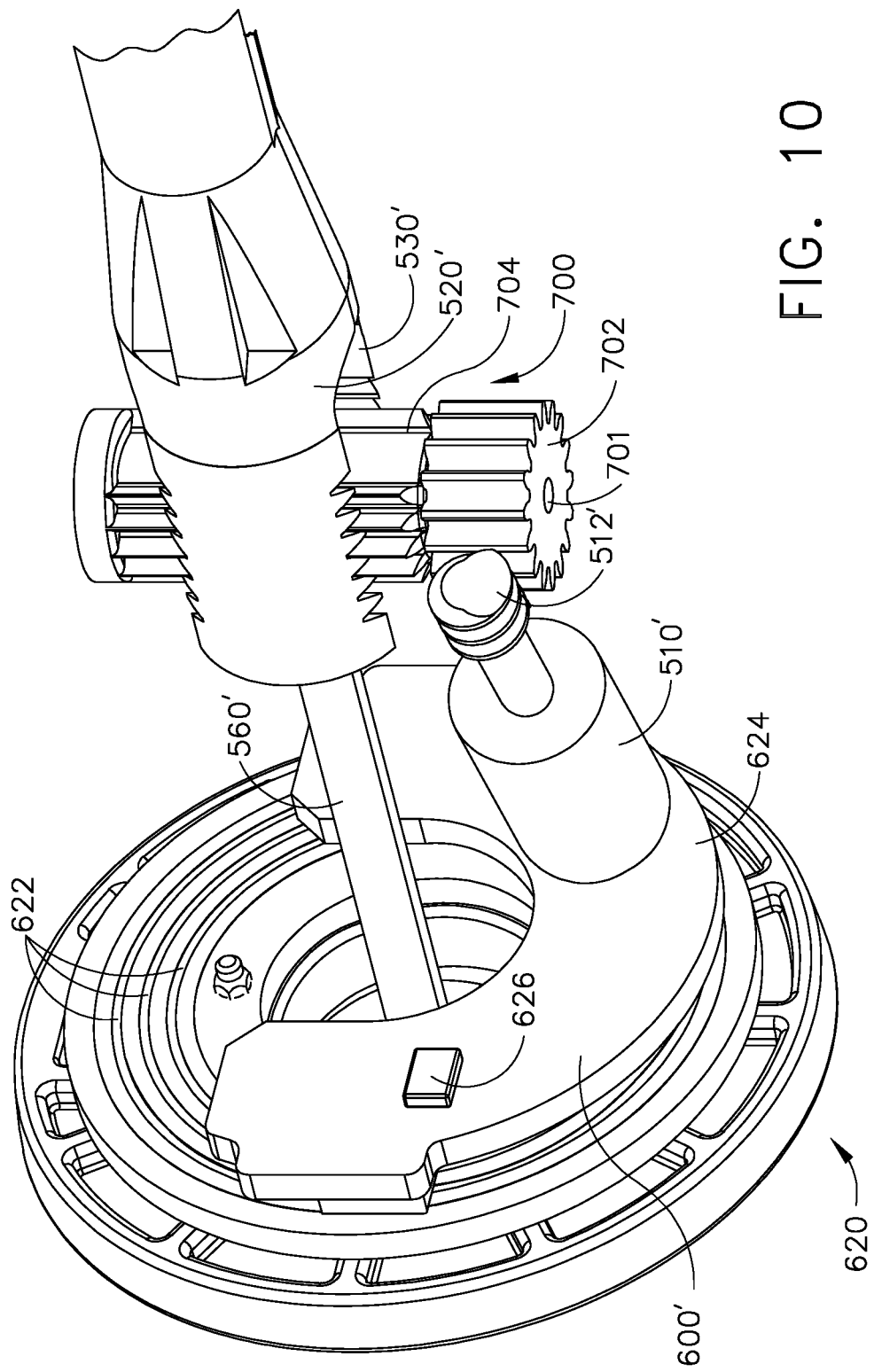
FIG. 10 is another perspective view of a portion of the interchangeable shaft assembly of FIG. 9 with various components omitted for clarity.
Figure 11:
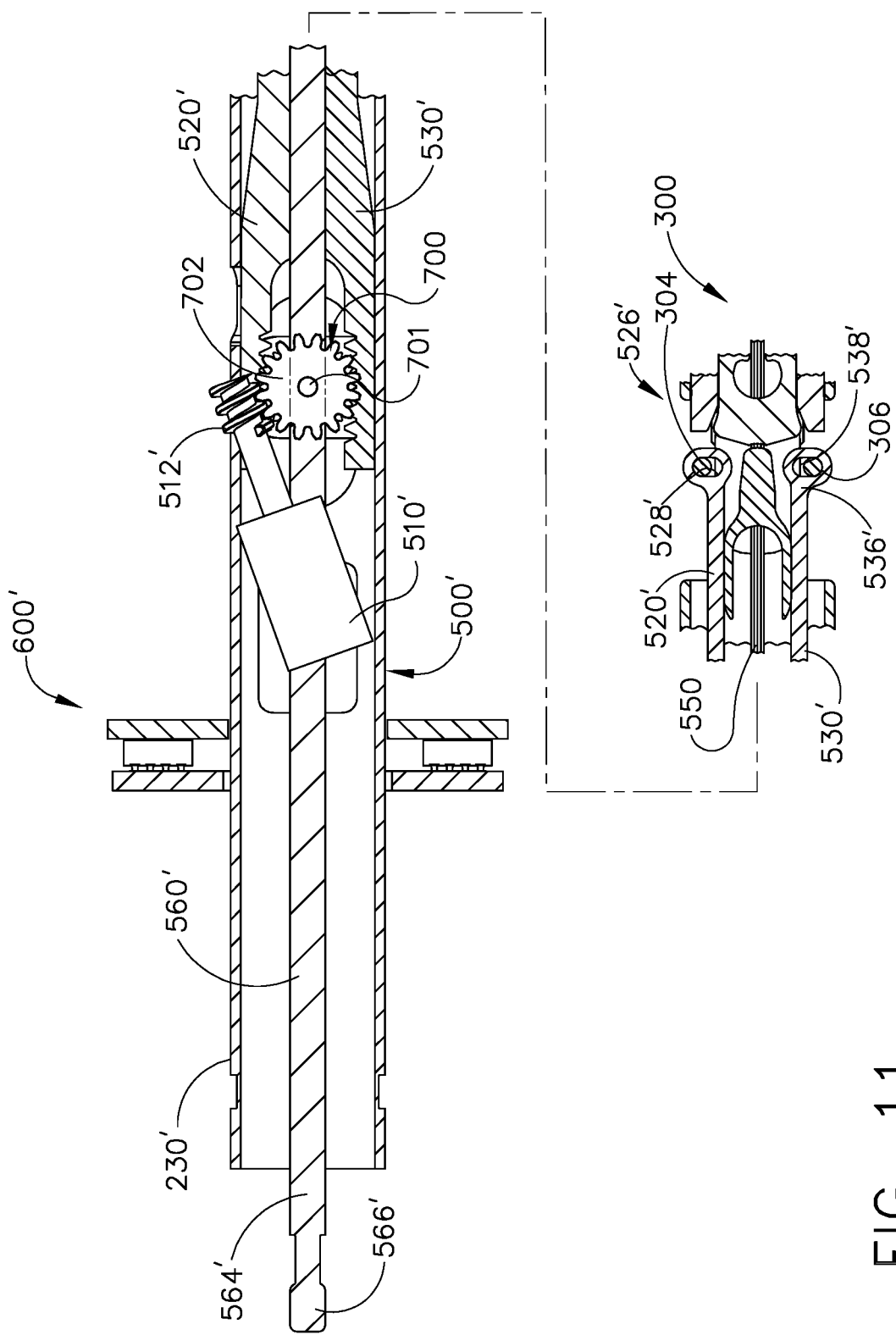
FIG. 11 is a partial cross-sectional view of a portion of the interchangeable shaft assembly of FIG. 10 with some components omitted for clarity.

FIGS. 9-11 illustrate another shaft assembly 200' that is substantially similar to shaft assembly 200 except for the differences discussed below. Those portions/components of shaft assembly 200' that are also found in shaft assembly 200 will be designated with like element numbers. As can be seen FIGS. 9-11, the shaft assembly 200' includes an articulation system 500' that comprises an articulation motor 510' that is used to actuate first and second articulation drivers 520', 530'. See FIGS. 10 and 11. The articulation motor 510' includes an articulation worm gear 512' that is in meshing engagement with an articulation gear assembly 700. In one form, the articulation gear assembly comprises an articulation spur gear 702 that is in meshing engagement with the articulation worm gear 512' and an articulation drive gear 704 that is in meshing engagement with portions of the first and second articulation drivers 520', 530'. The articulation gear assembly 700 and, more particularly, drive gear 704 is centrally disposed between a first gear rack 524' on the first articulation driver 520' and a second articulation gear rack 534' on the second articulation driver 530'. Rotation of the articulation drive gear 704 in a first direction will result in the axial movement of the first articulation driver 520' in a distal direction "DD" and the simultaneous axial movement of the second articulation driver 530' in the proximal "PD" or opposite axial direction. Likewise, rotation of the articulation drive gear 704 in a second rotary direction will result in the axial movement of the second articulation driver 530' in the distal direction "DD" and the simultaneous axial movement of the first articulation driver 520' in the proximal or opposite direction "PD".

Referring to FIG. 11, the distal end 526' of the first articulation driver 520' includes a slot 528' that is configured to receive a corresponding pin 304 formed on the elongate channel of the end effector 300. Likewise, the distal end 536' of the second articulation driver 530' includes a slot 538' that is configured to receive a corresponding pin 306 formed on the elongate channel. Thus, axial movement of the articulation drivers 520', 530' in the above described manner will applying simultaneous "pushing and pulling" motions to the elongate channel of the end effector 300 and thereby result in pivotal articulation of the end effector 300 about the articulation axis. As indicated above, the surgical instrument 10 also includes a tissue cutting member that is configured for axial travel through the elongate slot in the surgical staple cartridge that is supported in the end effector 300. The tissue cutting member or tissue cutting surface (not shown) is formed on or otherwise attached to the distal firing member 550. The distal firing member 550 is attached to a firing rod 560' that is supported for axial travel within the spine assembly 250. The proximal firing member 560' has a centrally disposed axial slot therein (not shown) to accommodate the gear drive shaft 701 upon which articulation spur gear 702 and articulation drive gear 704 are mounted. See FIGS. 9 and 10. Such arrangement facilitates axial travel of the proximal firing member 560' in response to firing motions applied thereto by the firing system. The proximal end 564' of the proximal firing member 560' includes a lug 566' that is configured to be receive in a firing rod attachment cradle 164 provided in the distal end 163 of the drive member 160. See FIG. 2. Thus, actuation of the firing motor 152 will result in the axial movement of the drive member 160 and the proximal firing member 560' and the distal firing member 550.

The firing motor 152 and the articulation motor 510 communicate with the control circuit 156 (FIG. 2) and are interlocked by a switching arrangement generally designated as 600. In the illustrated configuration, the switching arrangement 600 includes a switch drum 610' that is rotatably supported on the closure member 230'. The switch drum 610' includes a laterally extending boss 611' that has an inwardly extending cam pin 612' mounted therein. Similar to the arrangement described above, the cam pin 612' extends inwardly into a cam slot provided in the closure member 230'. The switch drum 610' further includes opposed slots 614' that are configured to accommodate rotation of the nozzle lugs 406 therethrough. The switch drum 610' has an open bottom portion 613' to facilitate rotation of the switch drum 610' relative to the articulation motor 510' and the articulation gear assembly 700. See FIG. 9. The switch arrangement 600' also includes a movable switch component 618' that is mounted to a switch arm portion 616' of the switch drum 610'.

As discussed above, when the closure member 230' is in the proximal (unactuated) position, the cam pin 612' is in a first portion of the cam slot. A lock out spring 630' is mounted on the switch drum boss 611' to bias the switch drum 610' into that first position wherein the cam pin 612' is in the first portion of the cam slot. When in that first position, the movable switch component 618' is not in contact or in "actuation proximity" with switch component 626. When in this "firing lock" position, the control circuit prevents actuation of the firing motor 152. Stated another way, unless the movable switch component actuates switch component 626, no power is supplied to the firing motor 152. Thus, even if the clinician were to actuate the firing trigger 170 in an attempt to actuate the firing motor 152, the firing motor 152 would not actuate.

In the illustrated example, closure member assembly 230' is actuated by actuating the closure trigger 122. As the clinician depresses the closure trigger 122, the closure member assembly 230' is moved in the distal direction "DD" which ultimately causes the anvil to pivot to the clamped position onto the target tissue. As the closure member assembly 230' moves distally, the cam pin 612' interacts with the cam slot which results in the rotational movement of the switch drum assembly 610'. As the switch drum 610' is biased into an actuation direction against the force of the spring 612', the switch component 618' is brought into activation/registration with switch component 626 which causes the control circuit board 156 to permit power to flow to the firing motor 152 upon actuation of the firing trigger 170. When in that closed position, the closure member assembly 210' and the anvil are locked in the closed position in the manner described above. The control circuit 156 may also be configured such that when the switch components 618' and 626 are in actuation registration, the control circuit 156 prevents any flow of power to the articulation motor 510' should the rocker switch 515 be inadvertently actuated. Once the closure member assembly 210' and anvil are locked in clamped position, the clinician may actuate the firing trigger 170 to drive the cutting member through the end effector 300 and cut the target tissue clamped therein and fire the surgical fasteners on each side of the tissue cut line. The end effector 300 may also be equipped with sensor(s) (not shown) that communicate with the control circuit 156 to detect when the tissue cutting member has reached its distal-most position to thereby provide the control circuit with inputs to cause the firing motor 152 to stop and reverse its direction to retract the tissue cutting member to its starting position. Other sensor(s) may be employed to detect when the tissue cutting member has returned to the starting position and communicate with the control circuit 156 to thereby communicate that information to the clinician and/or enable the closure member assembly to be unlocked. Once the closure member assembly 210' has been unlocked, the lock out spring 630', acting on the switch drum 610', will urge the cam pin 612' to rotatably return the switch drum 610' back to that starting position which will deactivate the switch 626 and once again actuation of the firing motor 152 will be prevented by the control circuit.

FIGS. 12 and 13 illustrate an alternative shaft assembly 200" that is substantially similar to shaft assembly 200 except for the differences discussed below. Those portions/components of shaft assembly 200" that are also found in shaft assembly 200 will be designated with like element numbers. As can be seen in those Figures, the shaft assembly 200" comprises a spine assembly 250" that comprises a proximal frame end or proximal frame member 252" that is attached to a shaft frame 260 that is pivotally coupled to an end effector frame insert 330 that is attached to the elongate channel 302. The shaft frame 260 includes a pivot pin 262 that is configured to be rotatably received within a pivot aperture (not shown) in the end effector frame insert 330. Such arrangement serves to define the articulation joint 240 about which the end effector 300 may articulate.

The illustrated shaft assembly 200" includes first and second articulation drivers 520", 530" that are similar to articulation drivers 520, 530 as discussed above, except for the differences described below. As can be seen in FIGS. 12 and 13, for example, the first and second articulation drivers 520", 530" are slidably supported between the spine assembly 250" and a closure member assembly 210". Thus, the articulation drivers 520", 530" slide axially between those components when actuated to articulate the end effector 300 about the articulation joint 240. To provide support to the first and second articulation drivers 520", 530" during actuation thereof, an idler gear 264 is centrally disposed between the articulation drivers 520" and 530". The first articulation driver 520" includes a first distal gear rack 527 and the second articulation driver 530" include a second distal gear rack 537. The first and second distal gear racks 527, 537 are in meshing engagement with the idler gear 264 as shown. In addition, the proximal closure member segment 230" includes a first friction generating detent or locking tooth 234 that is configured to slidably engage a first toothed or serrated portion 529 on the first articulation driver 520". The proximal closure member segment 230" also includes a second friction generating detent or locking tooth 236 that is configured to slidably engage a second toothed or serrated portion 539 on the second articulation driver 530". To facilitate some flexing of the serrated portions 529, 539 of the first and second articulation drivers 520", 530", respectively during articulation of the end effector 300, an amount of clearance is provided between the corresponding portion of the proximal frame member 252" and the serrated portions 529, 539 of the articulation drivers 520", 530". For example, the portions of the proximal frame member 252" that do not correspond to the serrated portions 529, 539 may have a diameter "D" and the portion of the proximal frame member 252" that corresponds to the serrated portions 529, 539 may have a smallest diameter of "M" wherein M<D. Such arrangement provides clearance for flexing of the articulation drivers 520", 530" as the drivers 520", 530" are axially advanced. During such axial advancement, the detent teeth 234, 236 engage the corresponding serrated portions 529, 539 to prevent the articulation drivers 520", 530" from moving and essentially "lock" the end effector in position. This is not only advantageous for holding the end effector in an articulated orientation during performance of a surgical procedure, but also during shipping of the device which may prevent portions thereof from inadvertently becoming damaged. In addition, such locking arrangements serve to retain the articulation drivers in their respective attachment positions prior to the attachment of the shaft assembly to the handle or housing. In alternative arrangements, the friction generating detent or locking teeth may each be spring biased into contact with the corresponding serrated portions of the articulation drivers. For example, each tooth may be separately movable in directions transverse to the serrated portions. A biasing member or spring may be situated in connection with each locking tooth to bias the tooth into retaining engagement with the corresponding serrated portion.

FIGS. 14-24 illustrate portions of another interchangeable shaft assembly 1200 that may be employed with surgical instrument 10. Those components of the interchangeable shaft assembly 1200 that are identical to components of the interchangeable shaft assembly 200 described above will be described below with like element numbers. In the illustrated arrangement, the shaft assembly 1200 includes a spine assembly 1250 upon which a closure member assembly 1210 is movably supported. The spine assembly 1250 includes a proximal spine segment 1252 that rotatably supported in a frame portion of the shaft assembly 1200. The proximal spine segment 1252 has two diametrically opposed notches 1253 that are configured to receive corresponding lug portions 1406 extending inwardly from the nozzle portions 1402. Further details concerning the shaft frame assembly and the rotary attachment of the proximal spine segment 1252 therein as well as the rotary attachment of the nozzle portions 1402 thereto may be found in U.S. patent application Ser. No. 13/803,097, entitled ARTICULATABLE SURGICAL INSTRUMENT COMPRISING A FIRING DRIVE, U.S. Pat. No. 9,687,230, which has been herein incorporated by reference in its entirety.

Figure 21:
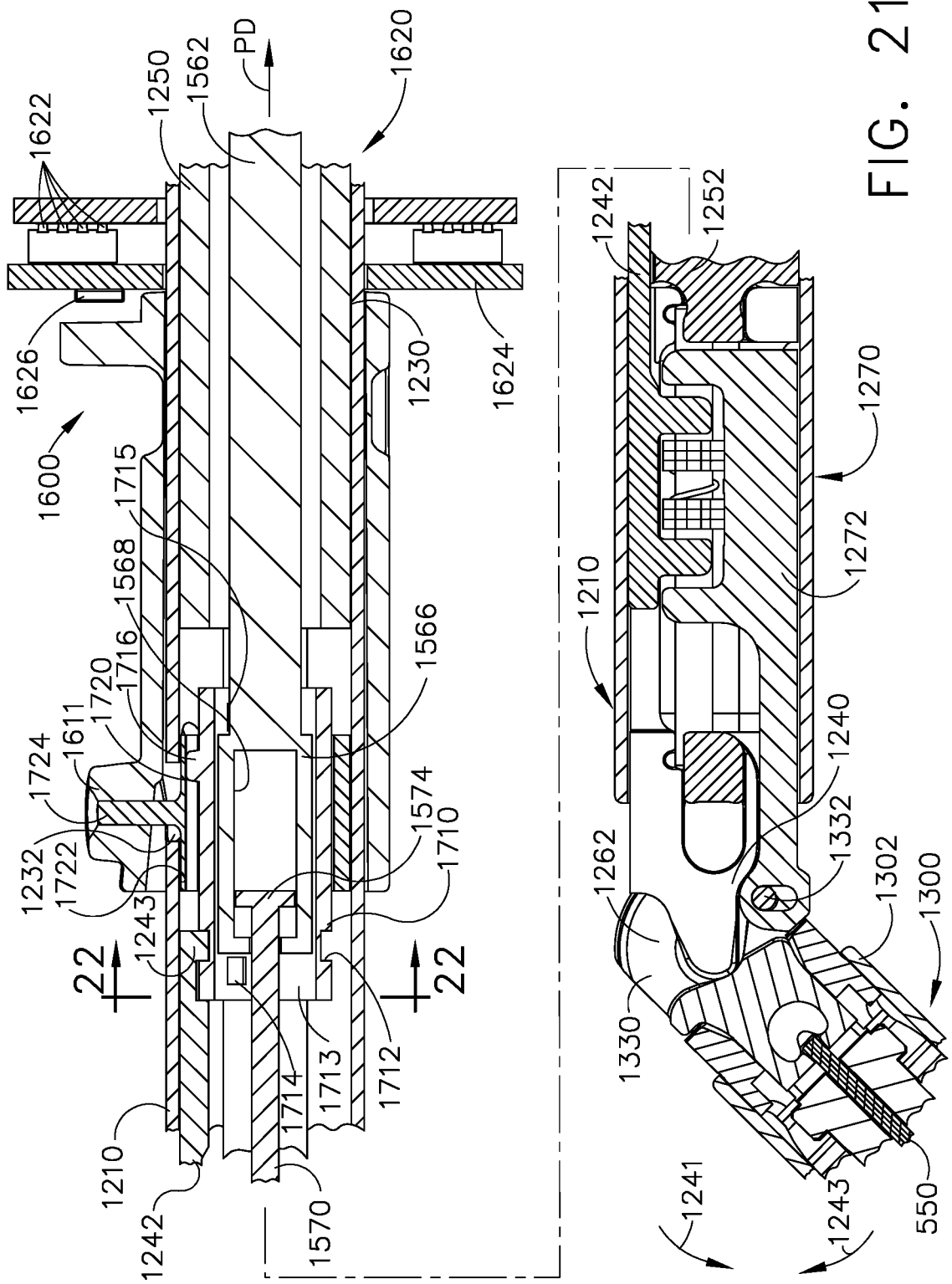
FIG. 21 is another cross-sectional view of a portion of the interchangeable shaft assembly of FIGS. 14-20 with the end effector in an articulated orientation.

Referring to FIGS. 16, 17, 18, 19, 22 and 24, the proximal spine segment 1252 is coupled to a distal frame member 1256 by a frame rib 1254 that extends therebetween within the closure member assembly 1210. As can be seen in FIGS. 20 and 21, the distal frame member 1256 is coupled to a frame 1260. The end effector 1300 is similar to end effector 300 and is configured to cut and staple/tissue in the above-described manners. The end effector 1300 includes an elongate channel 1302 that has an end effector frame insert 1330 attached thereto. Further details concerning the frame and end effector frame insert may also be found in U.S. patent application Ser. No. 13/803,097, entitled ARTICULATABLE SURGICAL INSTRUMENT COMPRISING A FIRING DRIVE, now U.S. Pat. No. 9,687,230. The shaft frame 1260 includes a pivot pin 1262 that is configured to be rotatably received within a pivot aperture (not shown) in the end effector frame insert 1330. Such arrangement serves to define the articulation joint 1240 about which the end effector 1300 may articulate. In the illustrated implementation, the interchangeable shaft assembly 1200 includes a proximal articulation driver 1242 that interfaces with an articulation lock 1270. Further details regarding the articulation lock 1270 may also be found in U.S. patent application Ser. No. 13/803,097, entitled ARTICULATABLE SURGICAL INSTRUMENT COMPRISING A FIRING DRIVE, now U.S. Pat. No. 9,687,230. As discussed in greater detail in that patent application, movement of the proximal articulation driver 1240, whether it be proximal or distal, can unlock the articulation lock 1270.

Figure 19:
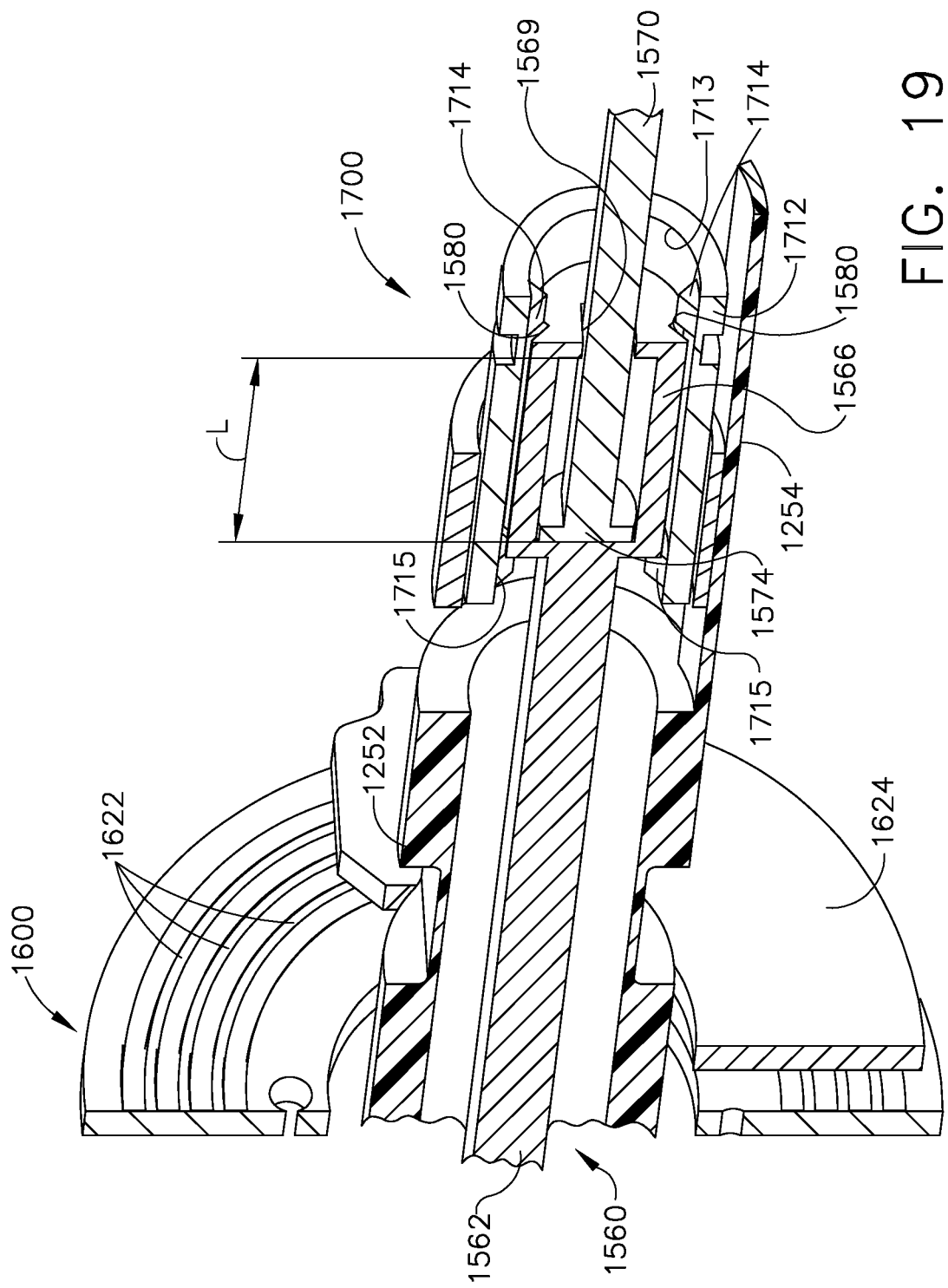
FIG. 19 is another cross-sectional perspective view of a portion of the interchangeable shaft assembly of FIGS. 14-18 with various components omitted for clarity and wherein the clutch assembly is in a firing orientation.

Still referring to FIGS. 19 and 20, the articulation lock 1270 includes a distal articulation driver 1272 that is movably coupled to a drive pin 1332 on the end effector frame insert 1330. For example, the drive pin 1332 is closely received within a pin slot 1274 defined in the distal end 1273 of the distal articulation driver 1272 such that the drive pin 1332 can bear against a proximal sidewall of the pin slot 1274 and transmit a proximal pushing force P to the distal articulation driver 1272. Such proximal pushing force P will only serve to bolster the locking engagement achieved by the articulation lock 1270. In order to release the locking engagement, and permit the end effector 1300 to be rotated in the direction indicated by arrow 1241, referring now to FIG. 21, the proximal articulation driver 1242 is pulled proximally to sufficiently unlock the lock components and permit the distal articulation driver 1272 to be moved proximally. In various circumstances, the proximal articulation driver 1242 can continue to be pulled proximally until a portion thereof pulls the distal articulation driver 1272 proximally to articulate the end effector 1300. After the end effector 1300 has been suitably articulated in the direction of arrow 1241, the proximal articulation driver 10040 can be released, in various circumstances, to permit the articulation lock 1270 to re-lock the distal articulation member 1272 in position. Further details regarding the construction and operation of the articulation lock 1270 may be found in U.S. patent application Ser. No. 13/803,097, entitled ARTICULATABLE SURGICAL INSTRUMENT COMPRISING A FIRING DRIVE, now U.S. Pat. No. 9,687,230, which has been herein incorporated by reference in its entirety.

As discussed above, one form of the interchangeable shaft assembly 1200 comprises an articulation driver system including a proximal articulation driver 1242 and a distal articulation driver 1272. When a drive force is transmitted to the proximal articulation driver 1242, whether it be in the proximal direction or the distal direction, the drive force can be transmitted to the distal articulation driver 1272 through the articulation lock 1270. In various circumstances, further to the above, the drive member 160 of the surgical instrument 10 can be utilized to impart such a drive force to the proximal articulation driver 1242. For instance, the interchangeable shaft assembly 1200 includes a clutch system 1700 which can be configured to selectively connect the proximal articulation driver 1242 to the drive member 160 of the surgical instrument 10 such that the movement of the drive member 160 is imparted to the proximal articulation driver 1242. In use, the clutch system 1700 is movable between an engaged state (FIG. 22) in which the proximal articulation driver 1242 is operably engaged with a proximal firing member 1560 (and drive member 160) and a disengaged state (FIG. 24) in which the proximal articulation driver 1242 is not operably engaged with the proximal firing member 1560 (and the drive member 160).

Figure 16:
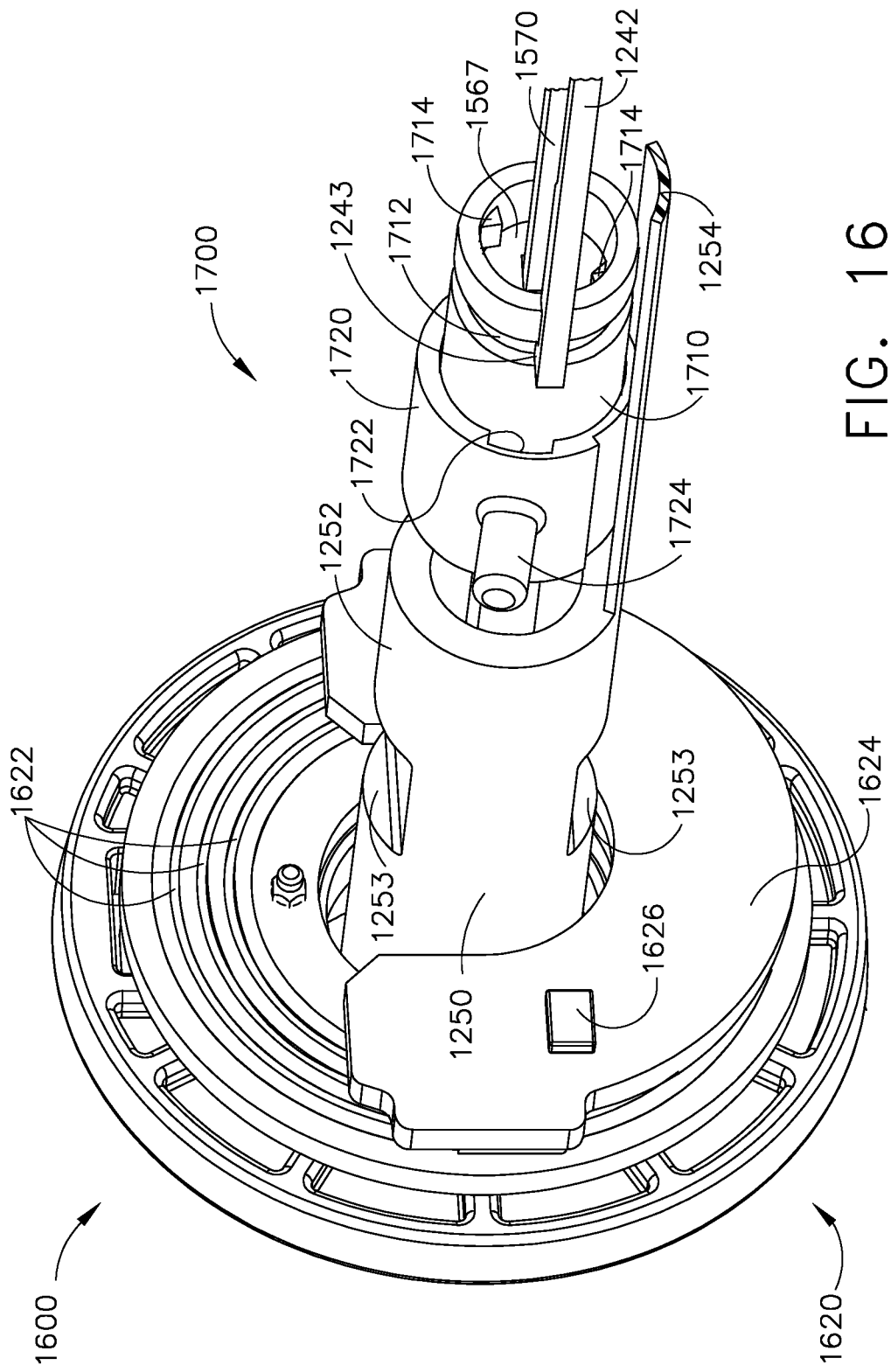
FIG. 16 is another perspective view of a portion of the interchangeable shaft assembly of FIGS. 14 and 15 with various components omitted for clarity.
Figure 17:
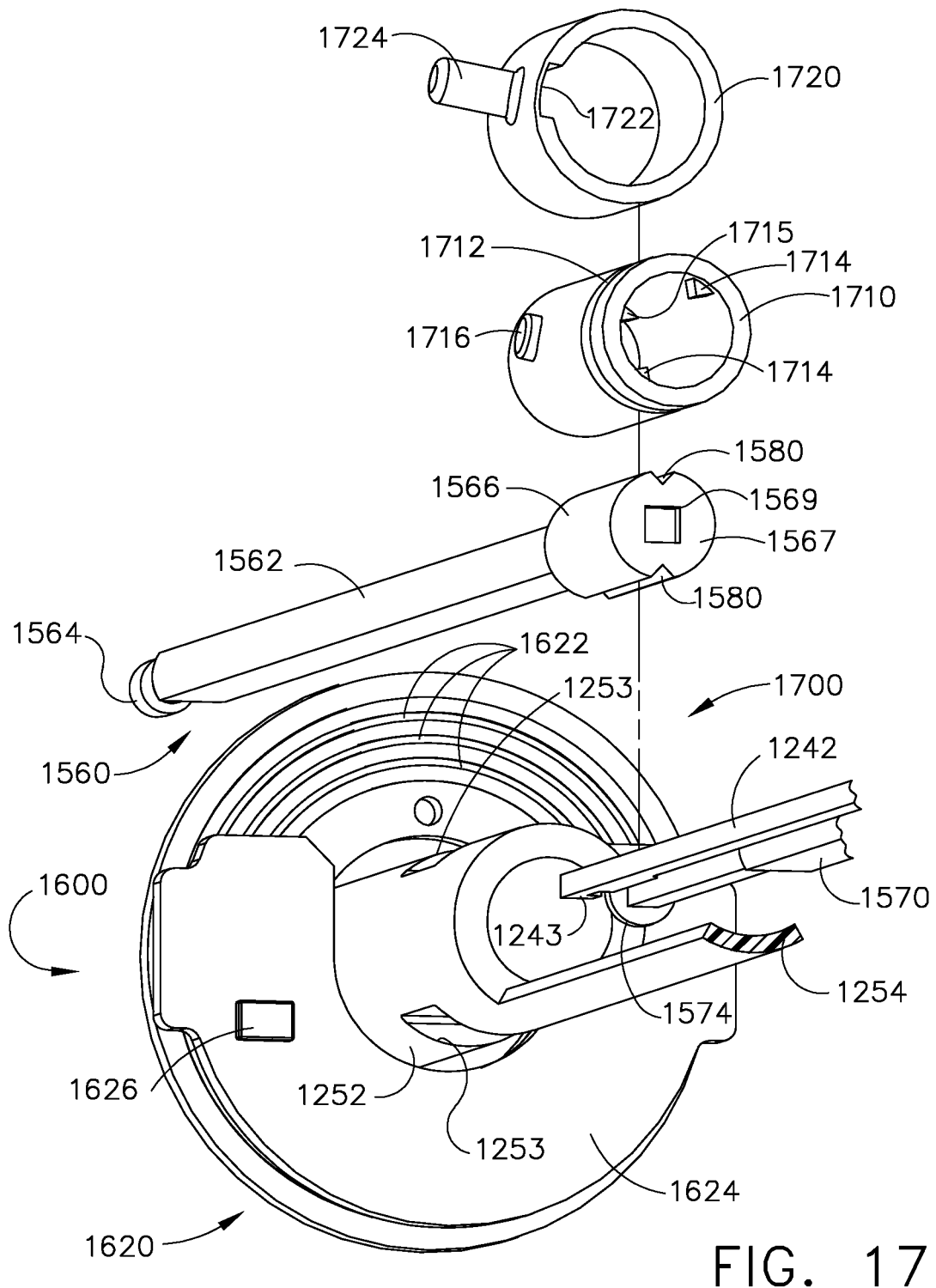
FIG. 17 is a partial exploded assembly view of a portion of the interchangeable shaft assembly of FIGS. 14-16.

In one form, the clutch system 1700 comprises an engagement member 1710 which can be configured to directly connect the proximal articulation driver 1242 to the proximal firing member 1560. As can be seen in FIG. 16, for example, the proximal articulation driver 1242 includes a proximal tab 1243 that is received within an annular groove 1712 provided in the perimeter of the engagement member 1710 to link the proximal articulation driver 1242 to the engagement member 1710 while permitting relative rotation therebetween. As can be seen in FIG. 17, the proximal firing member 1560 includes an elongate rod portion 1562 that has an attachment lug 1564 formed on the proximal end thereof. The attachment lug 1564 is configured to be rotatably supported in the cradle 162 on the drive member 160. See FIG. 2. As can be further seen in FIG. 17, the proximal firing member 1560 further comprises a firing rod coupler 1566 that is formed on the distal end of the rod 1562. The firing rod coupler 1566 includes a closed distal end 1567 that defines a cylindrical passage 1568. An aperture 1569 is formed through the closed distal end 1567 that is adapted to slidably receive a proximal end 1572 of an intermediate firing member 1570 therethrough. In the illustrated example, the intermediate firing member 1570 includes a stop member in the form of a disc 1574 that is formed on the proximal end 1572 thereof and is sized for sliding travel within the cylindrical passage 1568 in the firing rod coupler 1566. The distal end of the intermediate firing member 1570 is coupled to the proximal end of the distal firing member 550 in the various manners disclosed in, for example, U.S. patent application Ser. No. 13/803,097, entitled ARTICULATABLE SURGICAL INSTRUMENT COMPRISING A FIRING DRIVE, now U.S. Pat. No. 9,687,230, which has been herein incorporated by reference. In the illustrated arrangement, two diametrically-opposed, V-shaped engagement grooves 1580 are formed in the perimeter of the firing rod coupler 1566. See FIGS. 17-19. The V-shaped grooves 1580 are configured to slidably receive corresponding V-shaped articulation detents 1714, 1715 formed on the inner surface 1713 of the engagement member 1710.

Further to the above, referring again to FIGS. 16-24, the clutch system 1700 also comprises an actuator member 1720 that is configured to axially move on the engagement member 1710. As can be most particularly seen in FIG. 17, for example, a first engagement pin 1716 extends outward from the engagement member 1710 and is configured to be slidably received within a slot 1722 extending through the actuator member 1720. Such arrangement facilitates relative axial movement of the actuator member 1720 and the engagement member 1710 while also enabling the actuator member 1720 and engagement member 1710 to rotate as a unit. Also in the illustrated arrangement, the clutch system 1700 includes a cam pin 1724 that protrudes from the actuator member 1720. As with the arrangement described above, the cam pin 1724 extends out through a cam slot 1232 in a proximal closure member segment 1230. See FIG. 15.

The firing motor 152 communicates with the control circuit 156 and a switching arrangement generally designated as 1600. In the illustrated configuration, the switching arrangement 1600 includes a switch drum 1610 that is rotatably supported on the proximal closure member segment 1230. The switch drum 1610 includes a laterally extending boss 1611 that is adapted to receive an end of the cam pin 1724 therein. The switch drum 1610 further includes opposed slots 1614 that are configured to accommodate rotation of the nozzle lugs 1406 therethrough. See FIG. 14. The switching arrangement 1600 also includes a slip ring assembly 1620 which is configured to conduct electrical power and/or signals to and/or from the end effector 1300 to the handle 102 and more particularly to the control circuit 156 within the handle 102. The slip ring assembly 1620 includes a plurality of concentric, or at least substantially concentric, conductors 1622 on opposing sides thereof which can be configured to permit relative rotation between the halves of the slip ring assembly 1620 while still maintaining electrically conductive pathways therebetween. In the illustrated implementation, the slip ring assembly 1620 includes a bulkhead 1624 that has a switch component 1626 that communicates through the slip ring 1620 to the control circuit 156. The switch arrangement 1600 also includes a movable switch component 1618 that is mounted to a switch arm portion 1616 of the switch drum 1610. See FIG. 14.

Figure 14:
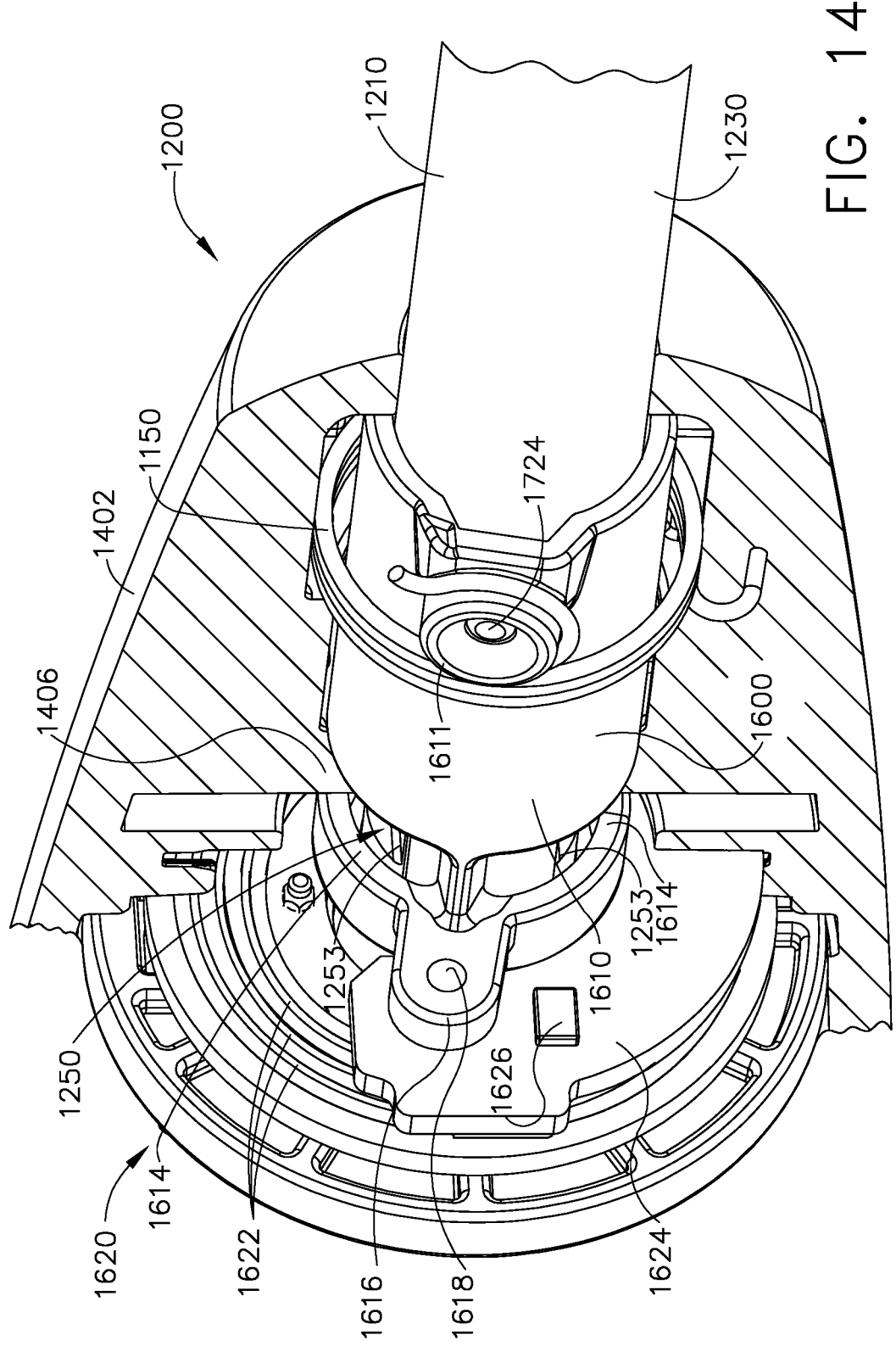
FIG. 14 is another perspective view of a portion of another interchangeable shaft assembly.
Figure 15:
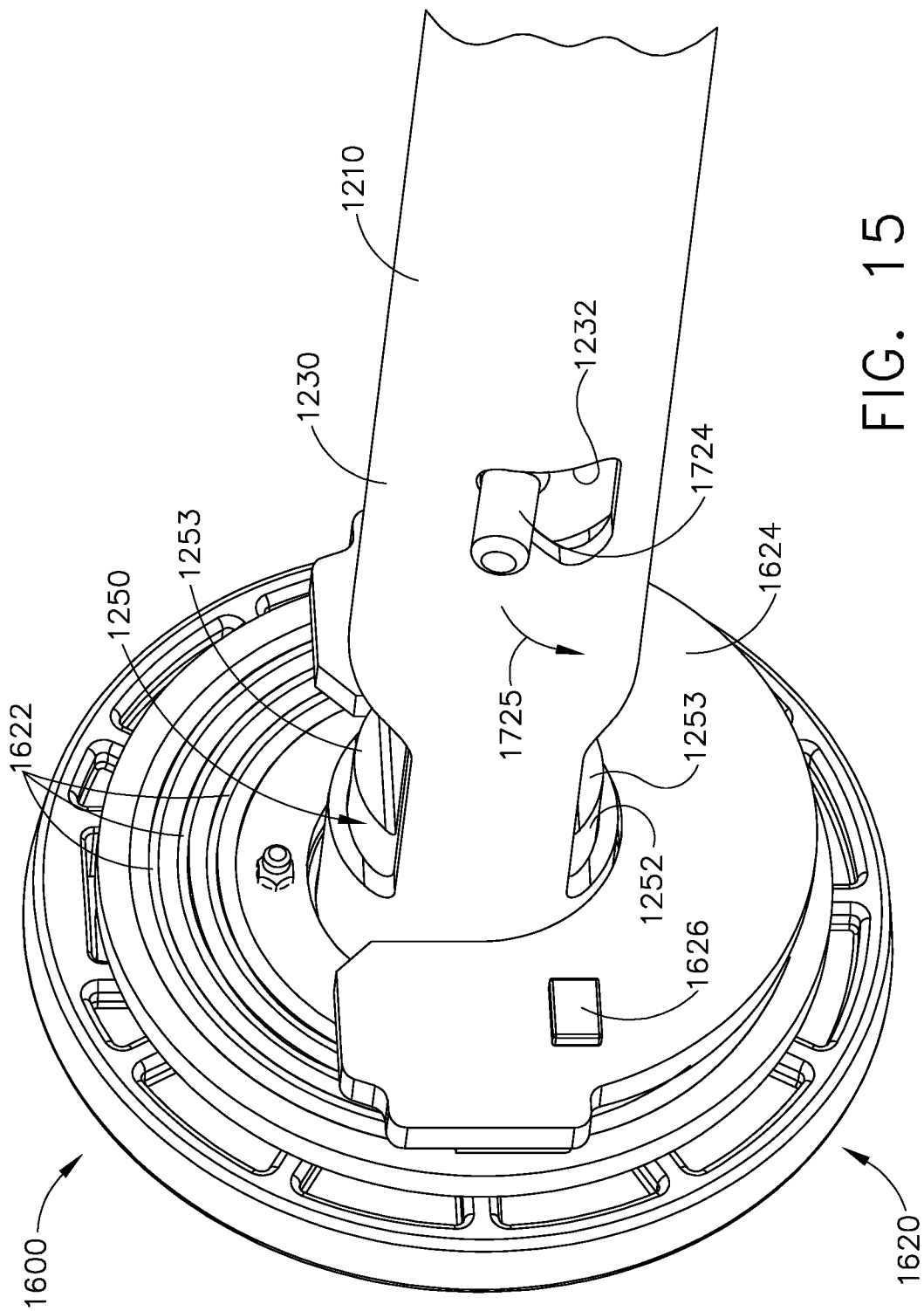
FIG. 15 is another perspective view of a portion of the interchangeable shaft assembly of FIG. 14 with various components omitted for clarity.

As discussed above, during a typical surgical procedure, the clinician may introduce the end effector 1300 into the surgical site through a trocar or other opening in the patient to access the target tissue. FIG. 20 illustrates the position of the end effector 1300 for insertion through a trocar port or otherwise into the patient to access the target tissue. As can be seen in that Figure, the end effector 1300 is unarticulated or stated another way is axially aligned with the shaft axis SA-SA. Once the end effector 1300 has passed through the trocar port, for example, the clinician may need to articulate the end effector 1300 to advantageously position it adjacent the target tissue. FIGS. 15, 18, 21 and 22 illustrate the positions of the clutch system components when the clutch system 1700 is in the articulation orientation. During the articulation process, the end effector 1300 is in an open position. Stated another way, the closure member assembly 1210 is positioned in its proximal "unactuated" position such that the distal end of the anvil of the end effector 1300 is spaced away from the surgical staple cartridge. FIG. 15 illustrates the position of the proximal closure member segment 1230 when in the unactuated or open position. As can be seen in that Figure, the cam pin 1724 is located in the upper portion of the cam slot 1232. When in that position, the cam pin 1724 locates the switch drum 1610 such that the switch component 1618 on the switch arm 1616 is not in actuation proximity or alignment with the switch component 1626 on the switch bulkhead 1624. Thus, when the switch 1626 is not actuated by switch 1618, the control circuit 156 may be configured to permit the firing motor 152 to fire for a limited closing stroke but unable to fire for a period that is sufficient to actuate or advance the intermediate firing member 1570 and the distal firing member 550 as will be discussed in further detail below. As can be seen in FIG. 14, a firing system lockout spring 1150 is provided on the boss 1611 of the switch drum 1610 to bias the switch drum 1610 and ultimately the cam pin 1724 into the upper portion of the cam slot 1232 in the unactuated or open position. See FIG. 14. Thus, when the closure member assembly 1210 and ultimately the anvil of the end effector 1300 is in the open position, actuation of the firing motor 152 will not result in the advancement of the intermediate firing member 1570 and the distal firing member 550 through the end effector 1300.

Figure 18:
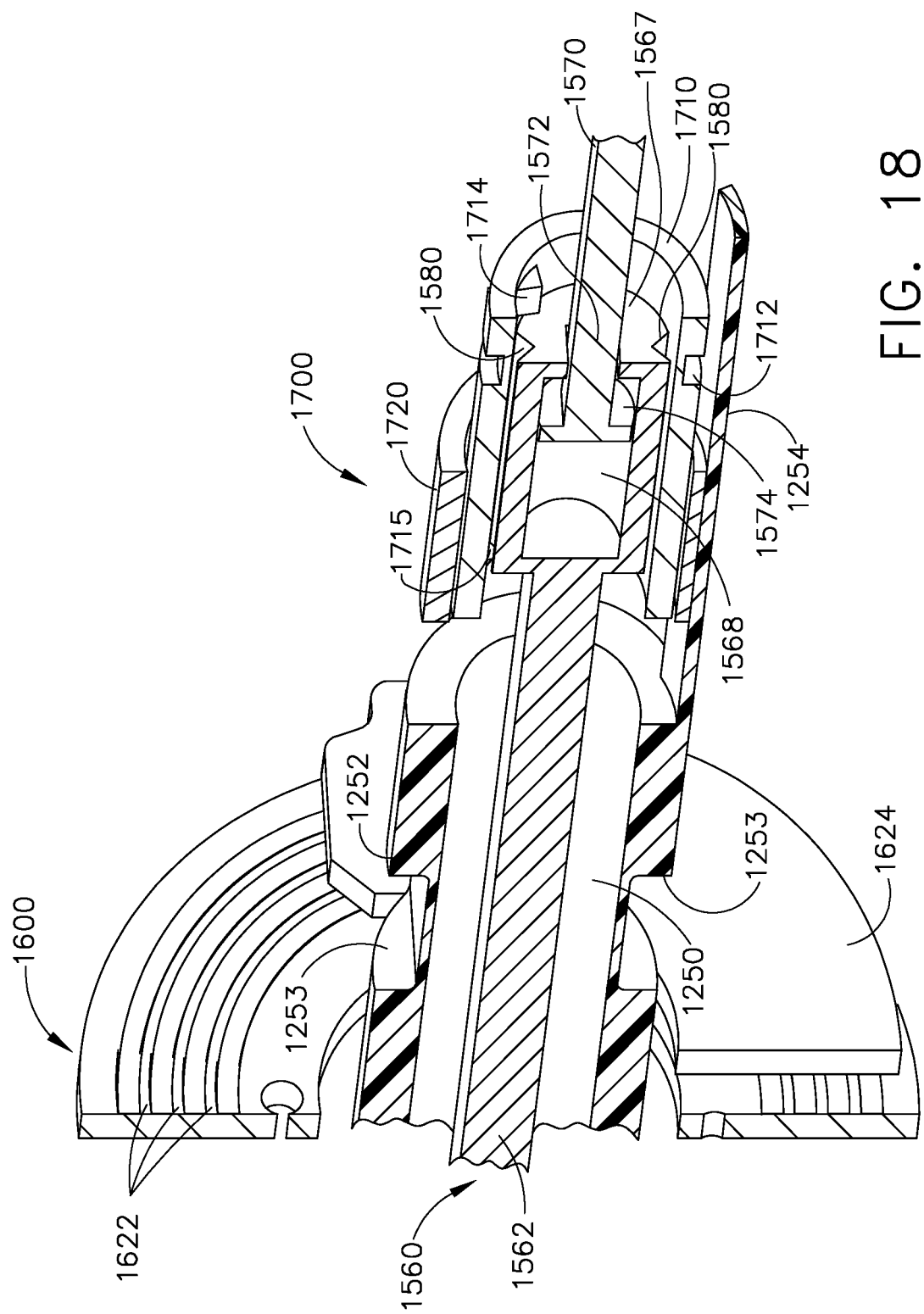
FIG. 18 is a cross-sectional perspective view of a portion of the interchangeable shaft assembly of FIGS. 14-17 with various components omitted for clarity and wherein the clutch assembly is in an articulation orientation.
Figure 22:
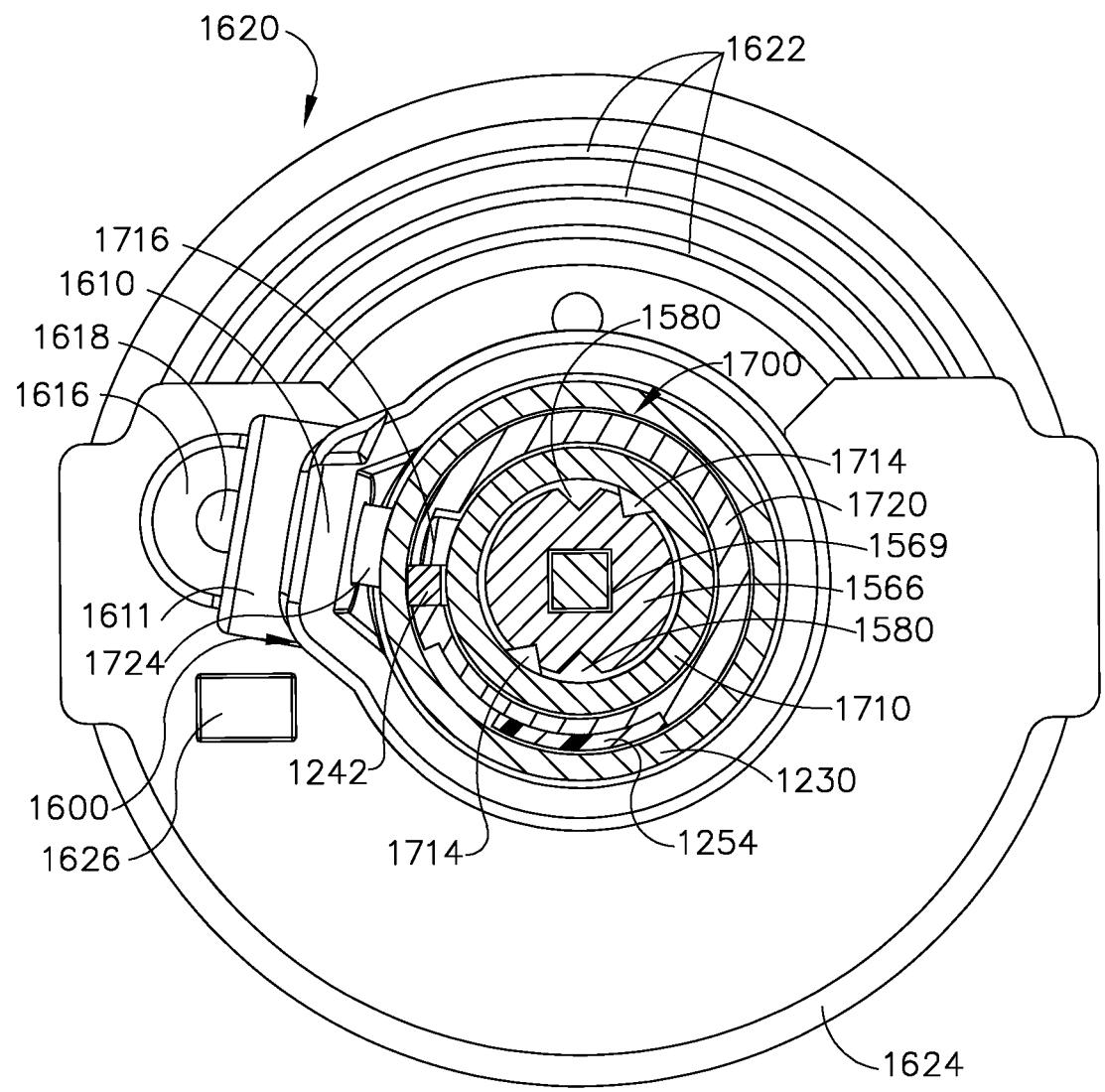
FIG. 22 is a cross-sectional view of the interchangeable shaft assembly of FIGS. 14-21 taken along lines 22-22 in FIG. 21.

Referring to FIGS. 18 and 22, when the clutch system 1700 is in the articulation orientation, the V-shaped detents 1714, 1715 are not aligned with the corresponding V-shaped slots 1580 in the firing rod coupler 1566. Thus, advancement of the drive member 160 and the proximal firing member 1560 in the distal direction "DD" will result in the distal advancement of the proximal articulation driver 1242 as shown in FIG. 21, for example. Such arrangement serves to pivot the end effector 1300 in the direction represented by arrow 1241 in FIG. 21. The drive member 160 and the proximal firing member 1560 are advanced distally by actuating the firing motor 152 in a first direction. In one implementation, the firing motor 152 may be actuated by actuating a rocker switch 515 mounted on the handle 102 in a first direction. To pivot the end effector 1300 in a second opposite direction (represented by arrow 1243 in FIG. 21) the rocker switch 515 is actuated in a second or opposite direction. In either case, however, because the closure member assembly 1210 is in the open position and the switch 1618 on the switch drum 1610 is out of actuation orientation with the switch 1626 on the switch bulkhead 1624, the control circuit 156 only permits actuation of the firing motor 152 for the time necessary to attain the desired articulation stroke but not of sufficient duration so as to advance the intermediate firing member 1570 distally. FIG. 20 illustrates the position of the stop member 1574 located on the distal end of the intermediate firing member 1570 within the cylindrical passage 1568 in the firing rod coupler 1566 when the clutch system 1700 is in the articulation mode, but prior to actuation of the firing motor 152. FIG. 21 illustrates the position of the stop member 1574 within the cylindrical passage 1568 after the firing motor 152 has been actuated to drive the proximal firing member 1560 in the proximal direction "PD". Because the V-shaped detents 1714 and 1715 are not aligned with the corresponding V-shaped slots 1580, movement of the proximal firing member 1560 and the firing rod coupler 1566 in the proximal direction "PD" causes the bottom of the firing rod coupler 1566 to contact the proximal detents 1715 and drive the engagement member 1710 in the proximal direction "PD" as well. Movement of the firing rod coupler 1566 also drives the articulation driver 1242 in the proximal direction thereby causing the end effector 1300 to articulate in the direction represented by arrow 1241 in FIG. 21. Actuation of the firing motor 152 in an opposite rotary direction will cause the proximal firing member 1560 to move in the distal direction "DD" such that the end 1567 thereof contacts the distal detents 1714 to drive the engagement member 1710 distally. Such distal movement of the engagement member 1710 also causes the articulation driver 1242 in the distal direction "DD" which results in the articulation of the end effector 1300 in an opposite articulation direction (represented by arrow 1243 in FIG. 21). Thus, it may be appreciated from the foregoing discussion that the proximal firing member 1560 may move axially for a predetermined amount of axial travel without axially advancing the intermediate firing member 1570 and the distal firing member 550 attached thereto. This predetermined amount of axial travel may be defined by the axial length "L" of the cylindrical passage 1568 in the firing rod coupler 1566. See FIG. 19.

Figure 23:
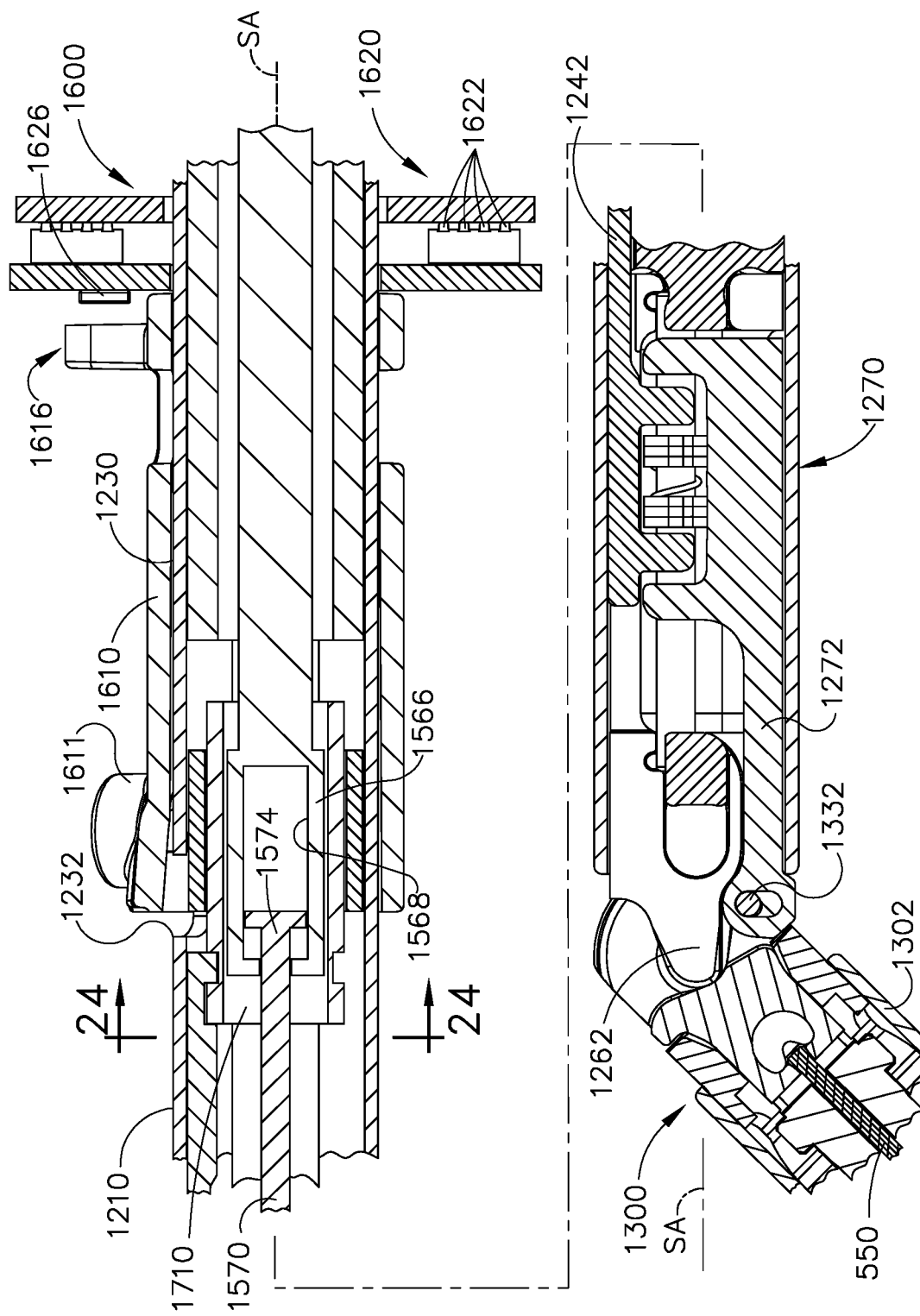
FIG. 23 is another cross-sectional view of a portion of the interchangeable shaft assembly of FIGS. 14-22 with the end effector in an articulated orientation and the clutch assembly in a firing orientation.
Figure 24:
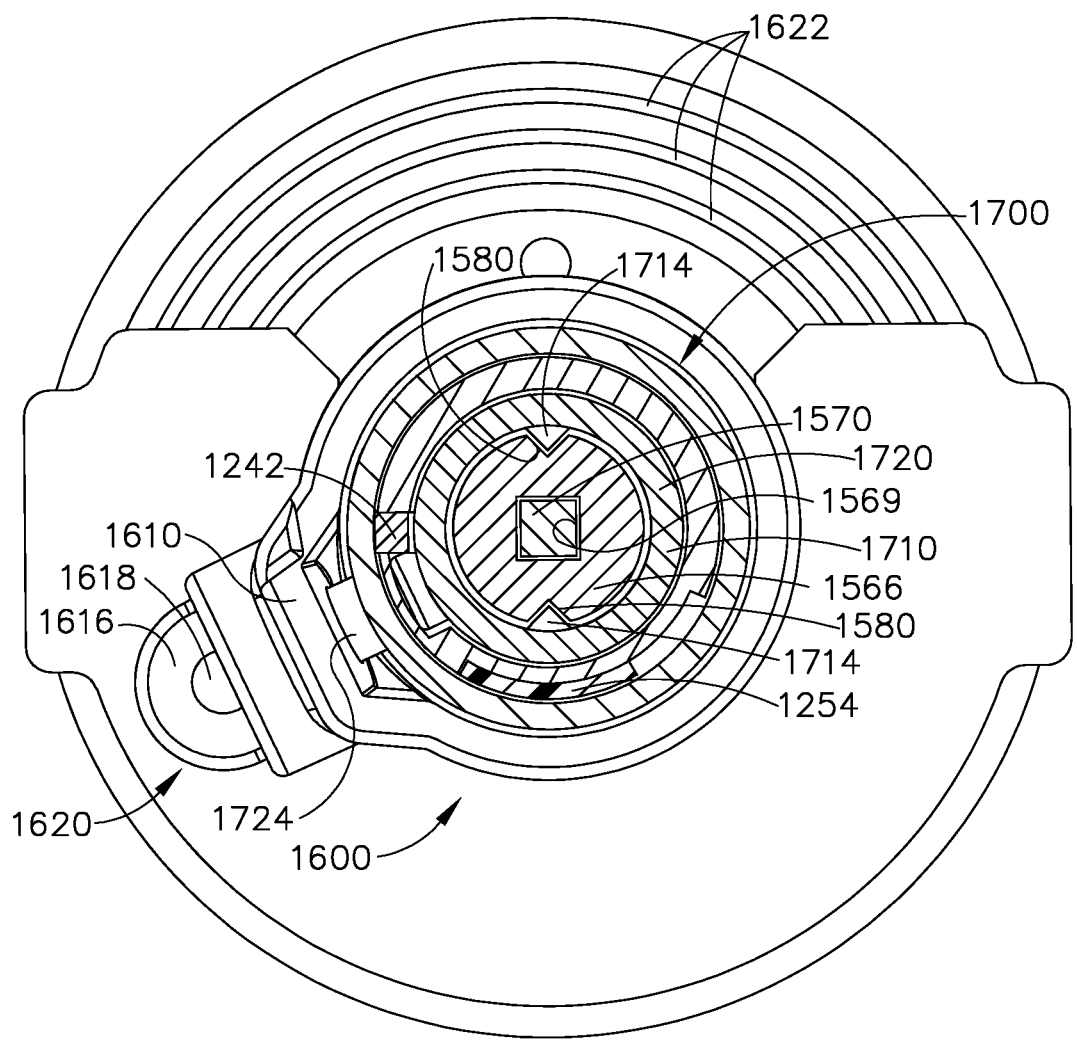
FIG. 24 is a cross-sectional view of the interchangeable shaft assembly of FIGS. 14-23 taken along lines 24-24 in FIG. 23.

Once the clinician has positioned the end effector 1300 in the desired orientation wherein the target tissue is located between the anvil and the staple cartridge, the clinician may then close the anvil to clamp the target tissue between the anvil and the staple cartridge. As discussed above, the anvil may be closed by actuating the closure trigger 122 to axially advance the closure member assembly 1210 in the distal direction "DD". As the closure member assembly 1210 moves distally, the cam slot 1232 in the proximal closure member segment 1230 causes the cam pin 1724 to move to the bottom of the cam slot 1232 (this movement is represented by arrow 1725 in FIG. 15). As the cam pin 1724 moves in the direction 1725, the switch drum 1610 is rotated on the closure member assembly 1210 such that the switch arm 1616 moves switch component 1618 into actuation registration with switch component 1626 to thereby provide the control circuit 156 with a signal indicating that the closure member assembly 1210 and, more precisely, that the anvil is in a closed position and ready for firing. The control circuit 156 will then enable the firing motor 152 to, upon actuation of the firing trigger 170, rotate for a sufficient firing time as to drive the distal firing member 550 (and cutting instrument attached thereto or otherwise mounted thereon) to its ending or completely fired position within the end effector 1300. FIGS. 19, 23 and 24 illustrate the positions of the various components of the clutch system 1700 in the firing orientation.

Many motorized surgical cutting and fastening instruments utilize a separate drive rod for articulation and for firing the device. Although that method employs a somewhat simple architecture, it can prove costly and have increased reliability concerns due to the fact that full drive systems are replicated in the design. Various arrangements disclosed herein employ a single drive mechanism to do both articulation and firing that also provide a means to lock the articulation before firing.

Figure 25:
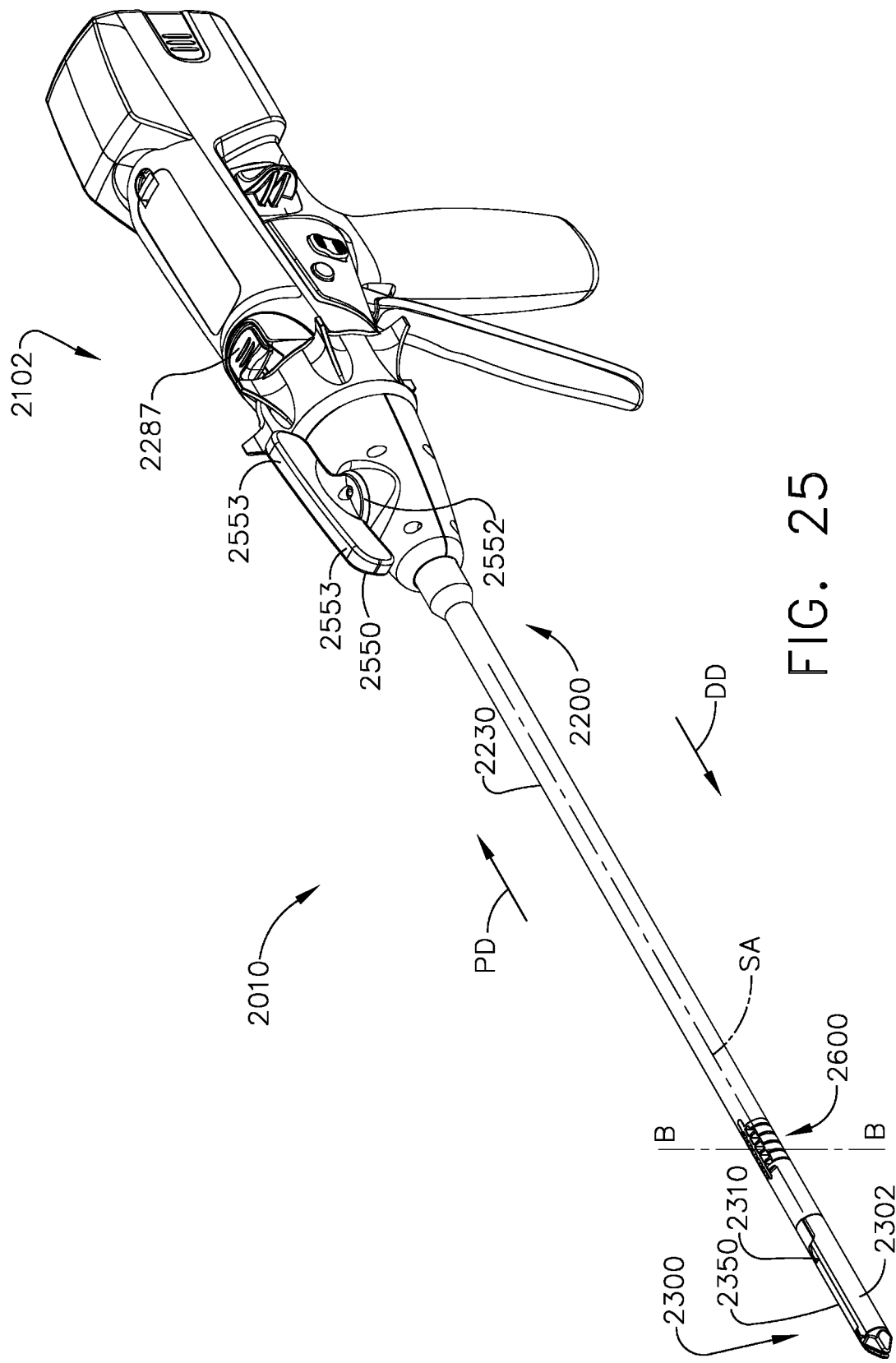
FIG. 25 is a perspective view of another surgical instrument with an articulatable surgical end effector operably coupled thereto.

When an articulatable end effector is used in surgery, it is desirable to prevent inadvertent detachment of the end effector from the surgical instrument, particularly when the end effector is in an articulated orientation. This problem can be exacerbated when using surgical instruments that employ interchangeable shaft assemblies that are detachable from the instrument handle or housing. For example, during use it is important to avoid inadvertent or in some cases careless detachment of the shaft assembly or end effector from the instrument when the end effector is in an articulated orientation. FIG. 25 illustrates another articulatable surgical instrument 2010 that includes an interchangeable shaft assembly 2200 that is removably mounted to the handle 2102 of the instrument 2010. An end effector 2300 is attached to the interchangeable shaft assembly 2200 and is selectively articulatable about an articulation axis B-B. The shaft assembly 2200 includes a unique and novel locking system for preventing detachment of the interchangeable shaft assembly 2200 from the handle 2102 when the end effector is in an articulated orientation. The surgical instrument 2010 is identical to surgical instrument 10 described above except for at least the differences discussed below. As can be seen in that Figure, the depicted surgical instrument 2010 is motor driven (or "powered") and includes a housing or handle 2102 that has interchangeable shaft assembly 2200 operably attached thereto. Various features and details regarding interchangeable shaft assemblies may be found in U.S. patent application Ser. No. 13/803,053, entitled INTERCHANGEABLE SHAFT ASSEMBLIES FOR USE WITH A SURGICAL INSTRUMENT, now U.S. Pat. No. 9,883,860, the entire disclosure of which is hereby incorporated by reference herein and in U.S. patent application Ser. No. 14/226,075, filed Mar. 26, 2014, entitled MODULAR POWERED SURGICAL INSTRUMENT WITH DETACHABLE SHAFT ASSEMBLIES, now U.S. Pat. No. 9,743,929, the entire disclosure of which is also hereby incorporated by reference herein.

Still referring to FIG. 25, an end effector 2300 is operably attached to the interchangeable shaft assembly 2200. The end effector 2300 may be identical to end effector 300, for example and include, among other things, an elongate channel 2302 that is configured to operably support a staple cartridge 2310 therein. The end effector 2300 further includes an anvil 2350 that has a staple forming undersurface thereon. The anvil 2350 is moved between open and closed positions by a closure tube assembly 2120 that is axially advanced in the distal and proximal directions by actuating a closure trigger 2122. The closure tube assembly 2120 includes a proximal closure tube shaft segment 2230 that is operably coupled to a distal closure tube segment 2220 by an articulation joint 2240 to facilitate articulation of the end effector 2300 about an articulation axis B-B that is transverse to a shaft axis SA-SA defined by the interchangeable shaft assembly 2200.

Figure 26:
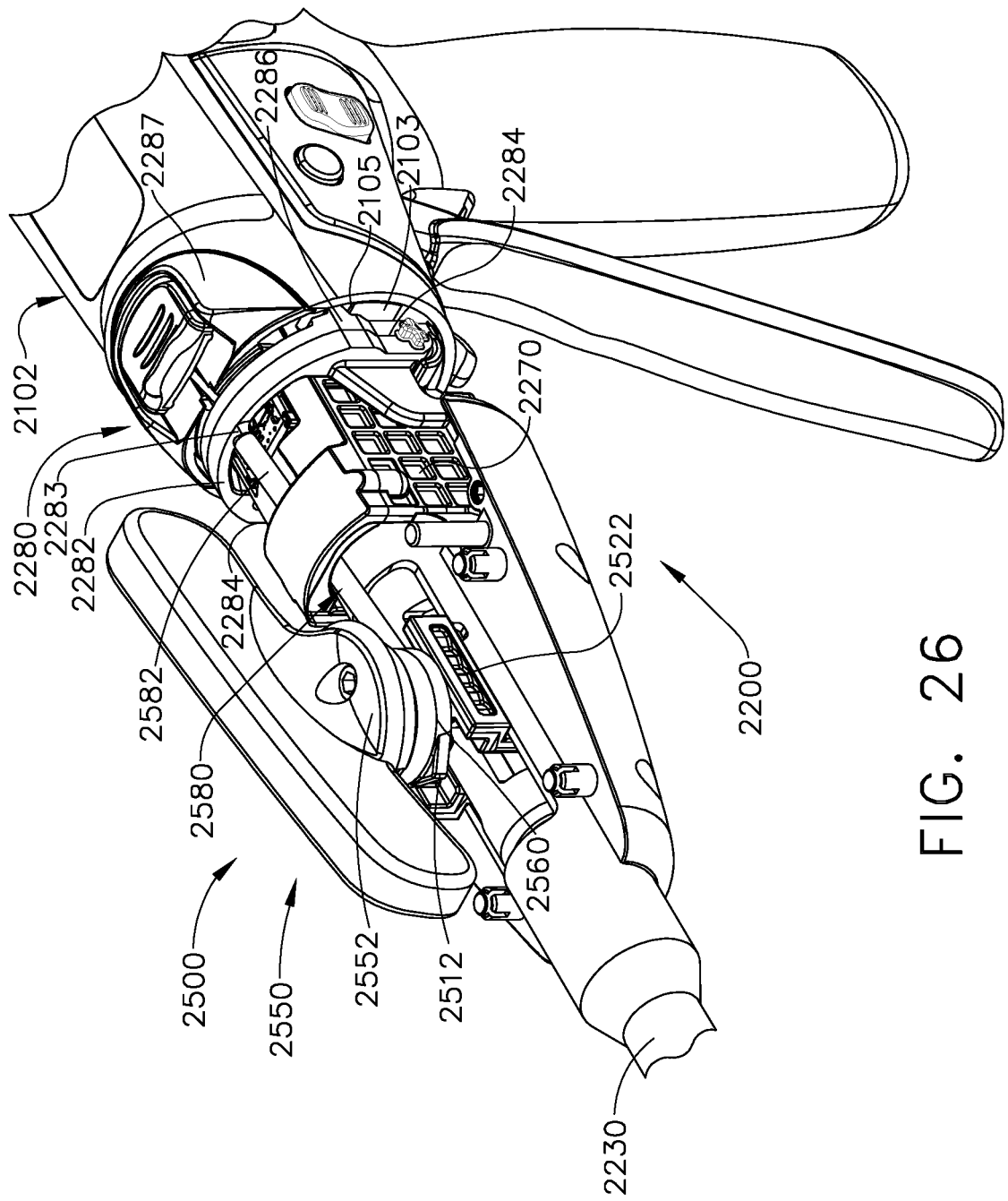
FIG. 26 is a perspective view of a handle portion of the surgical instrument of FIG. 25 with a portion of the nozzle housing omitted for clarity.
Figure 27:
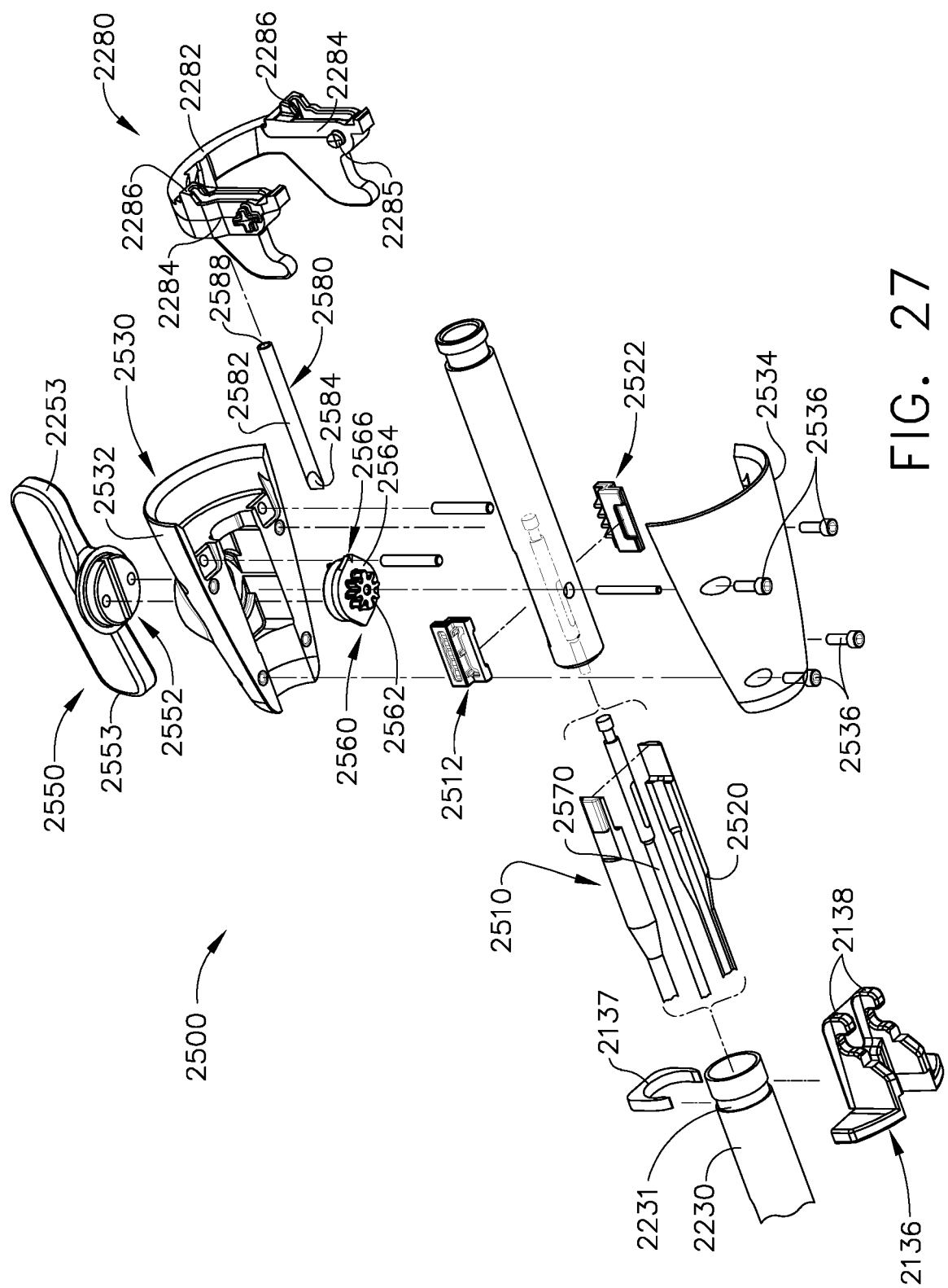
FIG. 27 is an exploded perspective view of a portion of the surgical instrument of FIGS. 25 and 26.
Figure 28:
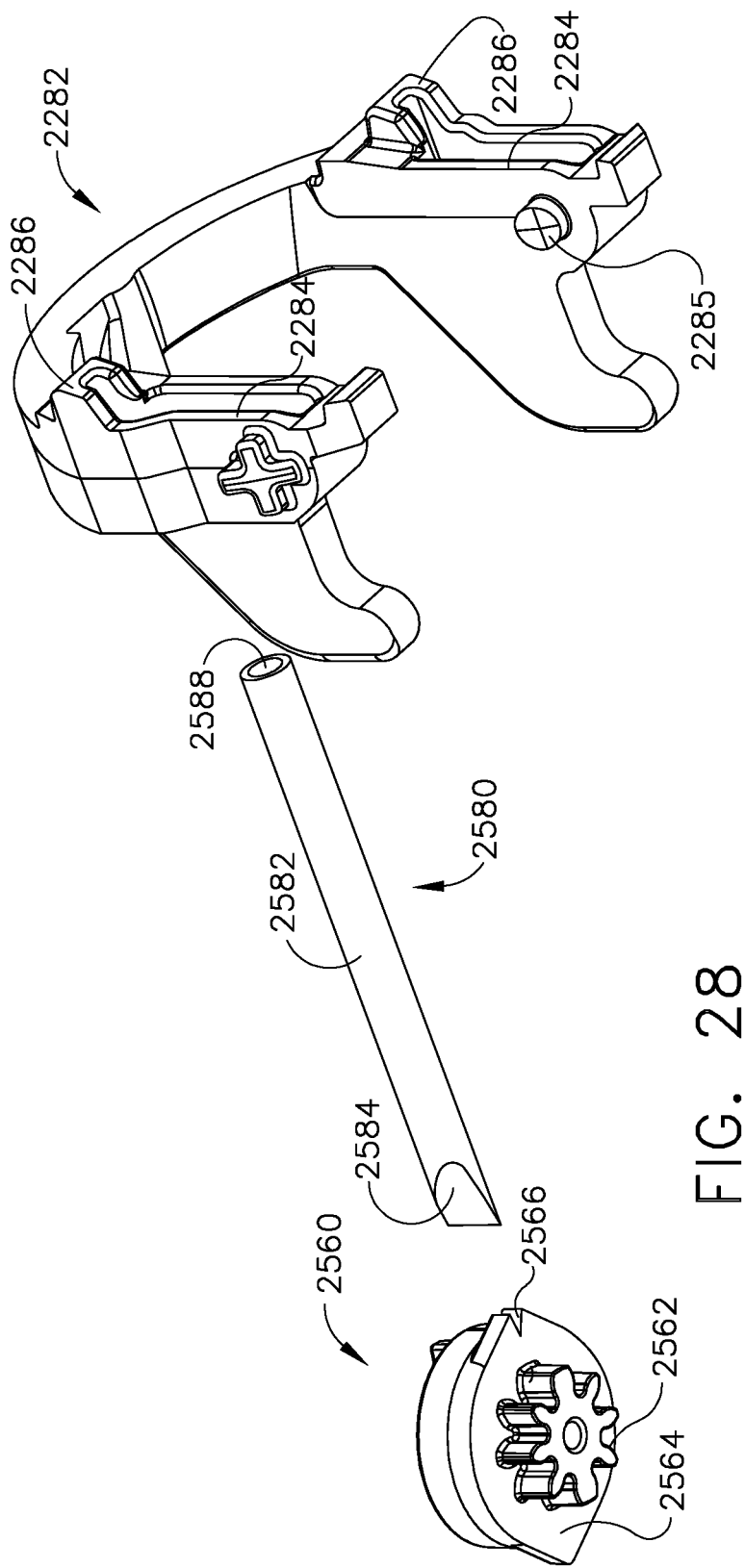
FIG. 28 is an exploded assembly view of portions of a lock assembly of the surgical instrument of FIGS. 25-27.

Referring to FIG. 26, the shaft assembly 2200 includes a chassis 2270 that is configured to be removably coupled to the handle 2102. Various shaft assembly embodiments employ a latch system 2280 for removably coupling the shaft assembly 2200 to the handle 2102 and more specifically to the handle frame. As can be seen in FIG. 26, for example, in at least one form, the latch system 2280 includes a lock member or lock yoke 2282 that is movably coupled to the chassis 2270. In the illustrated embodiment, for example, the lock yoke 2282 has a U-shape with two spaced downwardly extending legs 2284. The legs 2284 each have a pivot lug 2285 formed thereon that is adapted to be received in corresponding holes (not shown) that are formed in the chassis 2270. See FIG. 27. Such arrangement facilitates pivotal attachment of the lock yoke 2282 to the chassis 2270. The lock yoke 2282 may include two proximally protruding lock lugs 2286 that are configured for releasable engagement with corresponding lock detents or grooves 2105 in the distal attachment flange 2103 of the frame. See FIG. 27. The lock yoke 2282 may be biased in the proximal direction "PD" by a first spring or biasing member (not shown). Actuation of the lock yoke 2282 may be accomplished by a latch button 2287 that is slidably mounted on a latch actuator assembly that is mounted to the chassis 2270. The latch button 2287 may be biased in a proximal direction relative to the lock yoke 2282. As will be discussed in further detail below, the lock yoke 2282 may be moved to an unlocked position by biasing the latch button 2287 in the distal direction "DD" which also causes the lock yoke 2282 to pivot out of retaining engagement with the distal attachment flange 2103 of the frame. When the lock yoke 2282 is in "retaining engagement" with the distal attachment flange 2103 of the frame, the lock lugs 2286 are retainingly seated within the corresponding lock detents or grooves 2105 in the distal attachment flange 2103.

The interchangeable shaft assembly 2200 includes a closure shuttle 2136 that is slidably supported within the chassis 2270. The proximal closure tube segment 2230 is coupled to the closure shuttle 2136 for relative rotation thereto. For example, a U shaped connector 2137 is inserted into an annular slot 2231 in the proximal closure tube segment 2230 and is retained within vertical slots in the closure shuttle 2136. Such an arrangement serves to attach the proximal closure tube segment 2230 to the closure shuttle 2136 for axial travel therewith while enabling the proximal closure tube segment 2230 to rotate relative to the closure shuttle 2136 about the shaft axis SA-SA. The proximal closure shuttle 2136 includes hooks 2138 that are adapted to hookingly engage an attachment pin (not shown) that is attached to a second closure link (not shown) that is operably coupled to the closure trigger 2122 as described in detail in U.S. patent application Ser. No. 14/226,075, now U.S. Pat. No. 9,743,929. As described in that reference, actuation of the closure trigger 2122 will distally advance the closure link and apply a distal closure motion to the proximal closure shuttle 2136 and ultimately to the proximal closure tube segment 2230. A closure spring (not shown) is journaled on the proximal closure tube segment 2230 and serves to bias the proximal closure tube segment 2230 in the proximal direction "PD" which can serve to pivot the closure trigger 2122 into the unactuated position when the shaft assembly 2200 is operably coupled to the handle 2102.

The interchangeable shaft assembly 2200 further includes an articulation system 2500 for applying articulation motions to the first and second articulation bars 2510, 2520 that extend through the shaft assembly to operably interface with the end effector 2300. In the illustrated example, the articulation system 2500 further includes an articulation actuator 2550 that is rotatably supported on a nozzle housing 2530 that is supported on the chassis 2270. The nozzle housing may comprise two nozzle segments 2532, 2534 that are coupled together by a plurality of fasteners 2536. The articulation actuator 2550 comprises an articulation knob 2552 that is coupled to an articulation gear assembly 2560 that has an articulation pivot gear 2562 thereon. The articulation pivot gear 2562 is supported in meshing engagement with a first articulation gear rack 2512 that is attached to the first articulation bar 2510 and a second articulation gear rack 2522 that is attached to the second articulation bar 2520. Rotation of the articulation knob 2552 drivingly advances one of the articulation bars 2510, 2520 in a proximal or distal direction and the other of the articulation bars 2510, 2520 in the opposite direction to cause the end effector 2300 to articulate about the articulation axis in the desired direction.

The surgical end effector 2300 includes a firing member in the form of a tissue cutting member (not shown). The interchangeable shaft assembly 2200 also includes a firing rod segment 2570 that is configured to apply firing motions to the firing member. In the illustrated example, the firing rod segment is moved axially through the shaft assembly 2200 by the motor-driven firing system in the various manners described in further detail in the various references incorporated herein.

To prevent inadvertent detachment of the interchangeable shaft assembly 2200 from the handle 2102 when the end effector 2300 is in an articulated orientation, the shaft assembly 2200 further includes a unique and novel lock assembly generally designated as 2580. In the illustrated example, the gear assembly 2560 further includes a locking flange 2564 that has a lock notch 2566 therein. The lock assembly 2580 further includes a lock member 2582 that has pointed or tapered distal end 2584 that is configured for locking engagement with the lock notch 2566. The lock member 2582 is attached to the lock yoke 2282. In the illustrated example the lock member 2582 has an aperture 2588 that is adapted to receive a lock boss 2283 formed on the lock yoke 2282 to facilitate attachment of the lock member 2582 to the lock yoke 2282. See FIG. 26. In the illustrated example, the articulation knob 2552 is attached to the articulation lock assembly 2560 such that the lock notch 2566 is aligned for locking engagement with the lock member 2582 when the actuator fin portions 2553 of the articulation knob 2552 are axially aligned with the shaft axis A-A. See FIG. 25. When in such arrangement, the fin portions indicate to the clinician that the end effector 2300 is unarticulated and essentially in axial alignment with the shaft axis SA. Also when in that position, the distal end 2584 of the lock member 2582 is received in the lock notch 2566. When in that position, sufficient clearance is provided between the distal end 2584 of the lock member 2582 and the lock notch 2566 to enable the lock yoke 2282 to be moved in the distal direction to thereby detach the interchangeable shaft assembly 2200 from the handle. Thus, when the end effector is in the unarticulated orientation, the shaft assembly 2200 is detachable from the handle or housing.

When the clinician desires to articulate the end effector 2300, the clinician applies a rotary force to the articulation fin portions 2553 that is sufficient to cause rotation of the gear assembly 2560. As the gear assembly 2560 is rotated, the lock member 2582 moves in the proximal direction to permit the end 2584 of the lock member 2582 to move out of the lock notch 2566. The end 2584 rides around the rim of the locking flange 2564 during articulation. When in that position, the lock member 2582 prevents the lock yoke 2282 from moving sufficiently far enough in the distal direction to permit detachment of the shaft assembly 2200 from the handle. As such, when the end effector is in an articulated position, the lock yoke is prevented from moving to a detached or unlocked position. This arrangement not only prevents inadvertent detachment of the shaft assembly from the handle (i.e., by accident) but also prevents the clinician from detaching the shaft assembly 2200 using the latch button 2287.

Figure 29:
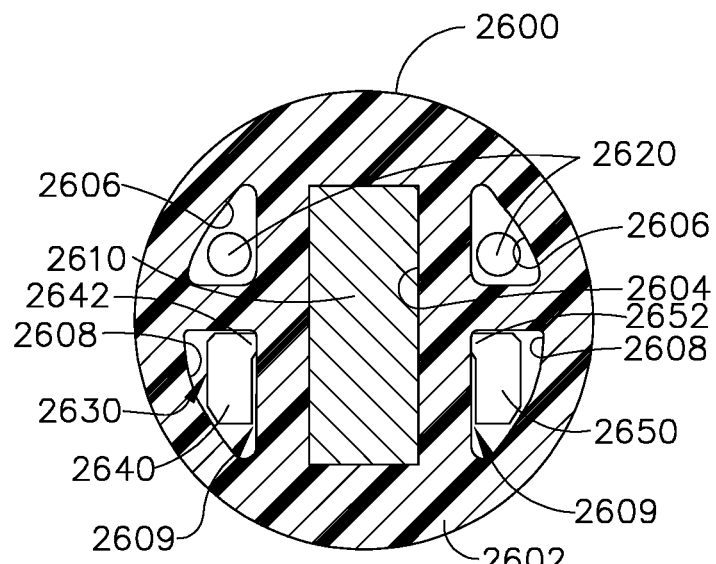
FIG. 29 is a cross-sectional view of an elongate shaft assembly of a surgical instrument.

FIG. 29 is a cross-sectional view through a flexible articulation joint member 2600 of the type, for example, shown in FIG. 25. The joint member comprises a flexible body 2602 that has a centrally disposed passage 2604 that is configured to slidably support a flexible firing beam 2610 therethrough. In this arrangement, the body 2602 includes two upper passages 2606 that are sized and arranged to accommodate a corresponding articulation cable 2620 therethrough. The articulation cables 2620 perform the same functions as the articulation drivers disclosed herein. For example, each of the cables 2620 is attached to or otherwise interface with the surgical end effector. The proximal ends or portions of the cables 2620 interface with an articulation control system for actuating the cables to articulate the end effector. The body 2602 further includes two lower passages 2608 that are adapted to accommodate corresponding portions of a frame assembly 2630. In this example, the frame assembly includes a first frame band 2640 and a second frame band 2650. The bands 2640, 2650 are located on each lateral side of the flexible firing beam 2610 and extend back to the handle or housing. Each band 2640, 2650 may comprise a cantilever spring arm that extends through the corresponding lower passages 2608 and be coupled to or otherwise interface with the end effector. For example, the distal end of each band 2640, 2650 may be attached to corresponding portions of the elongate channel of the end effector. The bands 2640, 2650 will flex to accommodate articulation of the end effector. As can be seen in FIG. 29 however, each band 2640, 2650 is configured for frictional engagement with corresponding portions of the walls 2609 of each of the lower passages 2608. In the illustrated example, each band 2640, 2650 includes a friction lug or formation 2642, 2652 thereon as shown. Such arrangement serves to frictionally retain the body portion 2602 in the articulated orientation.

Figure 30:
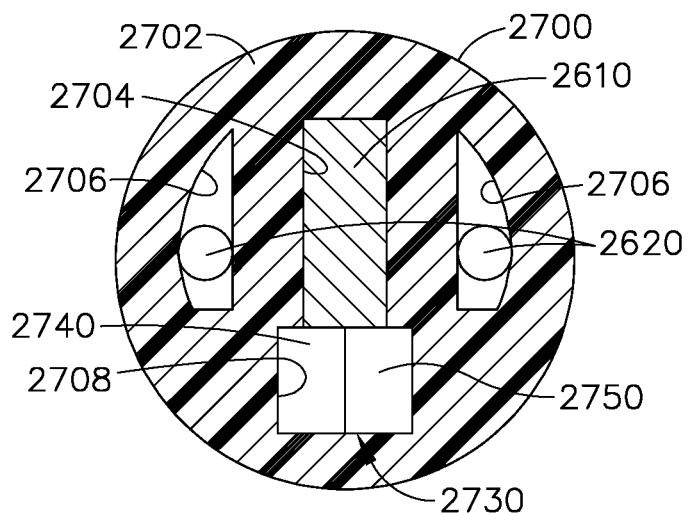
FIG. 30 is a cross-sectional view of another elongate shaft assembly of another surgical instrument.

FIG. 30 is a cross-sectional view through a flexible articulation joint member 2700 of the type, for example, shown in FIG. 25. The joint member comprises a flexible body 2702 that has a centrally disposed passage 2704 that is configured to slidably support a flexible firing beam 2610 therethrough. In this arrangement, the body 2702 includes two lateral passages 2706 that are sized and arranged to accommodate a corresponding articulation cable 2620 therethrough. In the illustrated arrangement, the passages 2706 are sized relative to the cables 2620 such that friction is generated between each cable and the walls of the corresponding passage 2706. The body 2702 further includes a lower passage 2708 that are adapted to accommodate corresponding portions of a frame assembly 2730. In this example, the frame assembly includes a first frame band 2740 and a second frame band 2750. The bands 2740, 2750 are located below the flexible firing beam 2610 and extend back to the handle or housing. Each band 2740, 2750 may comprise a cantilever spring arm that extends through the corresponding lower passages 2708 and be coupled to or otherwise interface with the end effector. For example, the distal end of each band 2740, 2750 may be attached to corresponding portions of the elongate channel of the end effector. The bands 2740, 7650 will flex to accommodate articulation of the end effector. As can be seen in FIG. the bands 2740, 2750 are in frictional engagement with the firing beam 2610 as well as with the walls of the lower passage 2708. Such arrangement serves to frictionally retain the body portion 2702 in the articulated orientation.

Figure 31:
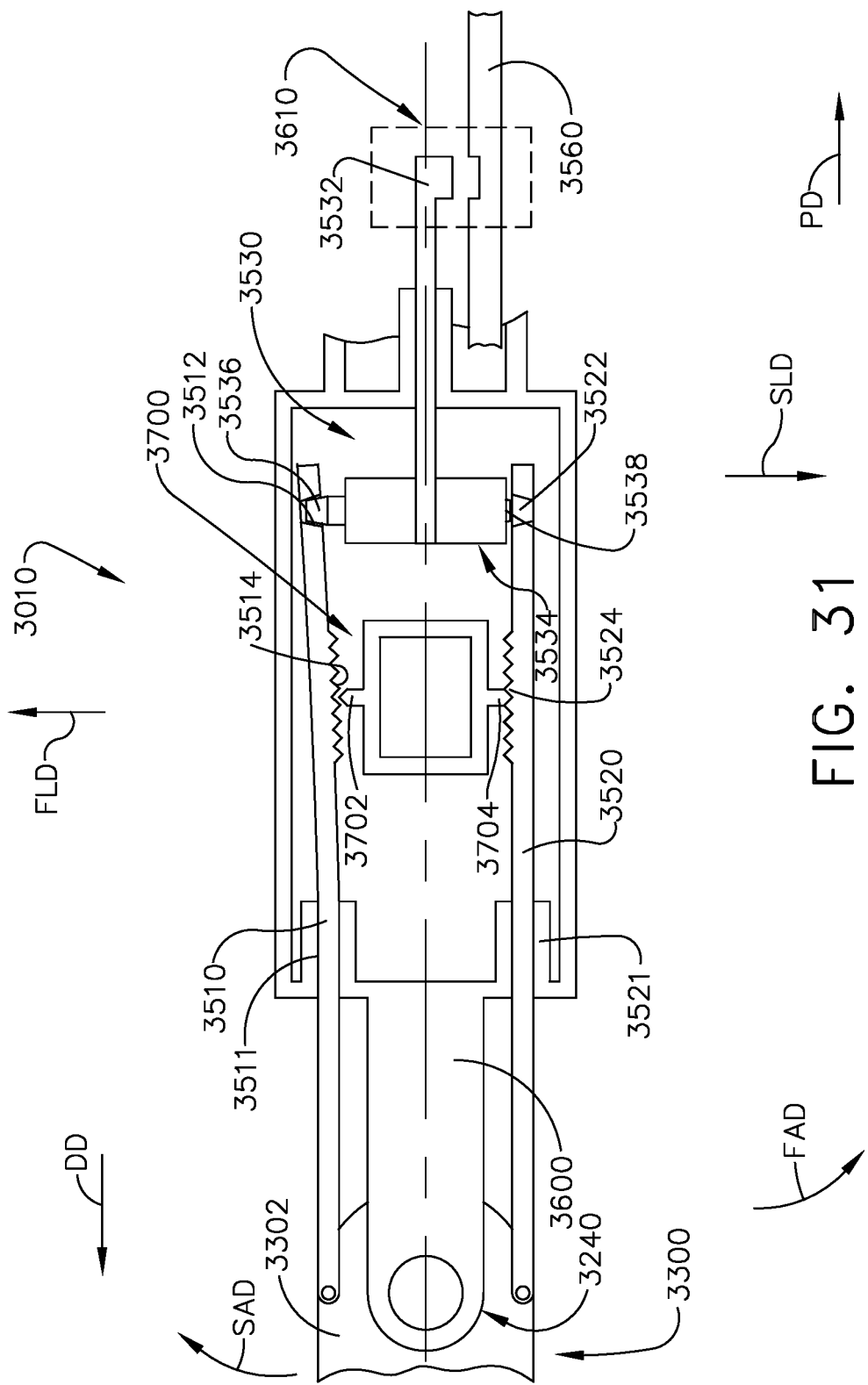
FIG. 31 is a diagrammatical view of a portion of another surgical instrument.

FIG. 31 illustrates in somewhat diagrammatical form, a surgical instrument 3010 with an articulatable end effector 3300 that employs a unique and novel articulation system 3500 for articulating the end effector 3300 about an articulation joint generally designated as 3240. In particular, the surgical instrument 3010 includes a frame assembly 3600 that is attached to the elongate channel 3302 of the surgical end effector 3300 such that the surgical end effector 3300 may be selectively articulated about the articulation joint 3240. The articulation system 3500 includes a first articulation member or bar 3510 and a second articulation member or bar 3520. Each of the first and second articulation bars 3510, 3520 are attached to the elongate channel 3302 of the surgical end effector 3300 and are arranged for axial movement relative to the frame assembly 3600. For example, the first articulation bar 3510 may be supported for axial movement relative to the frame assembly 3600 by a first bearing 3511 and the second articulation bar 3520 may be supported for axial movement relative to the frame assembly 3600 by a second bearing 3521.

The surgical end effector 3300 may comprise a surgical cutting and stapling device and include a firing member (not shown) that is configured for axial travel within the end effector 3300 as is taught in many of the references that have been herein incorporated by reference. The surgical instrument 3010 is equipped with a firing member 3560 that is configured to move axially in response to drive motions from a firing drive system of the various types disclosed herein as well as disclosed in the various references incorporated herein. The articulation system 3500 as generally depicted in FIG. 31 includes an articulation drive assembly 3530 that is configured to operably interface with firing drive system to receive firing motions therefrom. For example, the articulation driver 3532 of the articulation drive assembly 3530 may operably interface with the firing member 3560 through a switching or clutching arrangement 3610 of the type disclosed herein and/or in the references incorporated herein. Thus, when the switching arrangement 3610 is in the "articulation mode", operation of the firing drive system is transferred to the articulation driver 3532 to apply an axial articulation motion thereto. When the switching arrangement 3610 is in the "firing mode', actuation of the firing drive system will result in the axial advancement of the firing member 3560 within the surgical end effector 3300.

As can be further seen in FIG. 31, the articulation drive assembly 3532 further includes a dual-acting solenoid assembly 3534 that is attached to the articulation driver 3532. The solenoid assembly 3534 includes articulation engagement member 3536 that is arranged for selective driving engagement with a portion of the first articulation driver 3510. In addition, the solenoid assembly 3534 includes a second articulation engagement member 3538 that is arranged for selective driving engagement with the second articulation bar 3520. For example, FIG. 31 illustrates a portion of the first driver 3536 received in a first drive aperture 3512 in the first articulation driver 3510. A similar second drive aperture 3522 is shown in the second articulation driver 3520, however, in FIG. 31, the second driver 3538 is in a retracted or disengaged position. Other arrangements for drivingly engaging and disengaging the articulation drive assembly 3530 may also be employed. Thus, when the first articulation engagement member 3536 is in driving engagement with the first articulation driver 3510, actuation of the firing drive system will result in the axial advancement of the first articulation driver 3510 and when the second articulation engagement member 3538 is in driving engagement with the second articulation driver 3520, actuation of the firing drive system will result in the axial advancement of the second articulation driver 3520.

As was discussed in further detail herein, it may be desirable for the surgical instrument to employ means for locking the articulation drivers in position prior to use of the device and/or after the end effector has been articulated into a desired position. To that end, the surgical instrument 3010 is shown with an articulation lock system 3700. The articulation lock system 3700 comprises a first lock member 3702 configured for locking engagement with a first serrated or toothed locking portion 3514 of the first articulation driver 3510 and a second lock member 3704 configured for locking engagement with a second toothed or locking portion 3524 of the second articulation driver 3520. When the first lock member 3702 is engaged with the first serrated portion 3514 of the first articulation driver 3510, the first articulation driver 3510 will be retained in that axial position. Similarly, when the second lock member 3704 is engaged with the second serrated portion 3524 of the second articulation driver 3520, the second articulation driver 3520 will be retained in that axial position.

FIG. 31 illustrates the first articulation engagement member 3536 in driving engagement with the aperture 3512. As can be seen in that Figure, at least a corresponding portion 3516 of the first articulation driver 3510 is moved laterally in the first lateral direction "FLD" such that the first serrated portion 3514 is moved out of engagement with the first locking member 3702. As can also be seen in FIG. 31, the second articulation engagement member 3538 is retracted out of engagement with the articulation aperture 3522. When in that position, the first articulation driver 3510 is in an unlocked orientation and is free to be axially advanced in the distal direction "DD" to articulate the surgical end effector 3300 in a first articulation direction "FAD" about the articulation joint 3240. As the first articulation driver 3510 is moved distally, the second articulation driver 3520 necessarily will move in the proximal direction "PD" due to its connection to the elongate channel 3302 of the surgical end effector 3300. Such proximal movement of the second articulation driver 3520 will be accommodated by the second lock member 3704 "bumping" or riding or slipping over the corresponding serrations 3524. Likewise, to articulate the surgical end effector in a second articulation direction "SAD" about the articulation joint 3240, the first articulation engagement member 3536 is retracted out of engagement with the first articulation aperture 3512 and the second articulation engagement member 3538 is moved laterally in the second lateral direction "SLD" into engagement with the second articulation aperture 3522 to bias or otherwise move the second serrated portion 3524 of the second articulation driver 3520 out of engagement with the second lock member 3707. When in that position, the second articulation driver 3520 is in an unlocked orientation and is free to be axially advanced in the distal direction "DD" to articulate the surgical end effector 3300 in a second articulation direction "SAD" about the articulation joint 3240. As the second articulation driver 3520 is moved distally, the first articulation driver 3510 necessarily will move in the proximal direction "PD" due to its connection to the elongate channel 3302 of the surgical end effector 3300. Such proximal movement of the first articulation driver 3510 will be accommodated by the first lock member 3702 "bumping" or riding or slipping over the corresponding serrations 3514.

Figure 32:
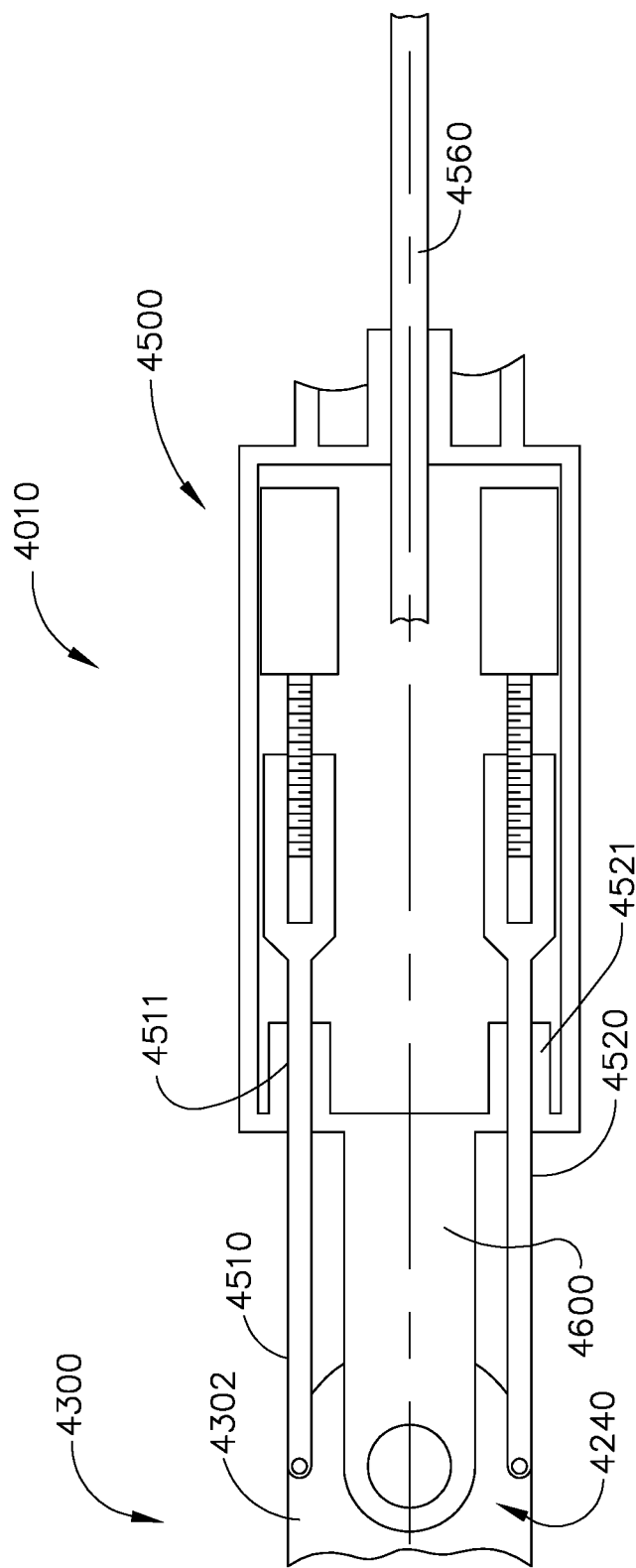
FIG. 32 is a diagrammatical view of a portion of another surgical instrument.

FIG. 32 illustrates in somewhat diagrammatical form, a surgical instrument 4010 with an articulatable end effector 4300 that employs a unique and novel articulation system 4500 for articulating the end effector 4300 about an articulation joint generally designated as 4240. In particular, the surgical instrument 4010 includes a frame assembly 4600 that is attached to the elongate channel 4302 of the surgical end effector 4300 such that the surgical end effector 4300 may be selectively articulated about the articulation joint 4240. The articulation system 4500 includes a first articulation member or bar 4510 and a second articulation member or bar 4520. Each of the first and second articulation bars 4510, 4520 are attached to the elongate channel 4302 of the surgical end effector 4300 and are arranged for axial movement relative to the frame assembly 4600. For example, the first articulation bar 4510 may be supported for axial movement relative to the frame assembly 4600 by a first bearing 4511 and the second articulation bar 4520 may be supported for axial movement relative to the frame assembly 4600 by a second bearing 4521.

The surgical end effector 4300 may comprise a surgical cutting and stapling device and include a firing member (not shown) that is configured for axial travel within the end effector 4300 as is taught in many of the references that have been herein incorporated by reference. The surgical instrument 4010 is equipped with a firing member or rod 4560 that is configured to move axially in response to drive motions from a firing drive system of the various types disclosed herein as well as the various references incorporated herein. The articulation system 4500 as generally depicted in FIG. 32 includes a first articulation drive motor 4530 that is configured to operably interface with the first articulation driver 4510 such that operation of the first articulation motor in one direction results in axial advancement of the first articulation bar 4510 in the distal direction "DD" and operation of the first articulation drive system in an opposite direction results in the axial movement of the first articulation bar 4510 in a proximal direction "PD". Similarly, the articulation system 4500 further comprises a second articulation drive motor 4540 that is configured to operably interface with the second articulation driver 4520 such that operation of the second articulation drive motor 4540 in one direction will result in the axial advancement of the second articulation driver in the distal direction "DD" and operation of the second articulation motor in an opposite direction will result in the axial advancement of the second articulation driver in the proximal direction "PD". The first and second articulation drive motors 4530, 4540 are controlled by a control circuit and controller arrangement, such that when one of the drive motors 4530 is operated to drive the articulation driver operably attached thereto in one axial direction for a first axial distance, the other articulation drive motor is operated in an opposite direction to move the other articulation driver operably coupled thereto in an opposite axial direction for a second axial distance that is equal to the first axial distance to accommodate articulation of the surgical end effector.

EXAMPLES

Example 1—A surgical instrument comprising a housing that has an interchangeable shaft assembly removably attached thereto that includes an elongate shaft. A surgical end effector is operably coupled to the elongate shaft for selective articulation relative thereto. An articulation system is configured to selectively apply articulation motions to the surgical end effector when the articulation system is in an actuated orientation. The surgical instrument further includes means for preventing detachment of the interchangeable shaft assembly from the housing when the articulation system is in the actuated orientation.

Example 2—The surgical instrument of Example 1, wherein the interchangeable shaft assembly is removably coupled to the housing by a latch member that is selectively movable between a latched position and an unlatched position and wherein the means for preventing detachment operable interfaces with the articulation system and the latch member.

Example 3—The surgical instrument of Examples 1 or 2, wherein the articulation system comprises an articulation actuator that is movably supported on the interchangeable shaft assembly and is selectively movable between an unactuated orientation wherein the surgical end effector is in an unarticulated orientation and a plurality of actuated orientations wherein the surgical end effector is articulated relative to a shaft axis defined by the elongate shaft. A first articulation member operably interfaces with the surgical end effector and the articulation actuator. A second articulation member operably interfaces with the surgical end effector and the articulation actuator.

Example 4—The surgical instrument of Example 3, wherein the articulation actuator comprises an articulation drive gear assembly that is in meshing engagement with the first and second articulation members.

Example 5—The surgical instrument of Example 4, wherein the articulation drive gear assembly is movable between the unactuated and the actuated orientations and wherein the means for preventing detachment comprises a lock member that operably interfaces with the articulation drive gear assembly and the latch member such that when the articulation drive gear assembly is in the unactuated position, the latch member is movable to the unlatched position and when the articulation drive gear assembly is in any one of the actuated positions, the lock member prevents the latch member from being moved to the unlatched position.

Example 6—The surgical instrument of Examples 4 or 5, wherein the articulation drive gear assembly comprises a locking flange that operably communicates with the articulation actuator. An articulation drive gear is coupled to the locking flange and a detachment notch is located in the locking flange. The detachment notch is located on the locking flange such that when the articulation drive gear assembly is in the unactuated orientation, a portion of the lock member may extend into the detachment notch in response to movement of the latch member from the latched position to the unlatched position and when the articulation drive gear assembly is in any one of the actuated positions, the portion of the lock member engages the locking flange to retain the locking member in a locked position wherein the latch member is prevented from being moved from the latched position to the unlatched position.

Example 7—The surgical instrument of Examples 1, 2, 3, 4, 5 or 6, wherein the surgical end effector comprises a pair of jaws wherein one jaw is selectively movable relative to the other jaw upon application of a closure motion thereto and wherein the elongate shaft further comprises a closure member that operably interfaces with one jaw to apply the closure motion thereto upon actuation of a closure system operably supported by the housing.

Example 8—The surgical instrument of Examples 1, 2, 3, 4, 5, 6 or 7, wherein the surgical end effector further comprises a firing member operably supported for axial travel through the surgical end effector upon application of a firing motion thereto and wherein the elongate shaft further comprises a firing rod that operably interfaces with the firing member to apply the firing motion thereto upon actuation of a firing system that is operably supported by the housing.

Example 9—The surgical instrument of Examples 1, 2, 3, 4, 5, 6, 7, 8 or 9, wherein the housing comprises a handle.

Example 10—A surgical instrument comprising an articulation system that is actuatable between an unactuated orientation and actuated orientations wherein the articulation system generates a corresponding articulation motion. The surgical instrument further comprises a surgical end effector and an elongate shaft assembly that operably interfaces with the surgical end effector to permit selective articulation thereof relative to the elongate shaft assembly. The elongate shaft assembly comprises at least one articulation member that operably interfaces with the surgical end effector and the articulation system. The at least one articulation member is supported for selective axial movement in response to an application of the articulation motions thereto by the articulation system. The surgical instrument further comprises means that are supported within the elongate shaft assembly and are configured to retainingly engage the at least one articulation member and prevent axial movement thereof when the articulation system is in the unactuated orientation.

Example 11—The surgical instrument of Example 10, wherein the articulation system is operably supported by a housing and wherein the elongate shaft assembly is removably attachable to the housing and wherein each of the at least one articulation members is axially movable from a neutral position wherein each articulation member is operably attachable to the articulation system upon attachment of the elongate shaft assembly to the housing and wherein the means for retainingly engaging retains each articulation member in the neutral position when the elongate shaft assembly is detached from the housing.

Example 12—The surgical instrument of Examples 10 or 11, wherein the means for retainingly engaging comprises a serrated portion on each of the articulation members. Each serrated portion is supported in meshing engagement with at least one corresponding lock tooth on another portion of the elongate shaft assembly.

Example 13—The surgical instrument of Example 12, wherein each articulation member is supported for axial movement within a hollow member and wherein each corresponding lock tooth protrudes inwardly from the hollow member.

Example 14—The surgical instrument of Examples 10, 11, 12 or 13, wherein the surgical end effector comprises a pair of jaws wherein one jaw is selectively movable relative to the other jaw upon application of a closure motion thereto and wherein the elongate shaft further comprises a hollow closure tube that operably interfaces with one of the jaws and houses each of the articulation members therein and wherein each corresponding tooth is formed on an inner wall of the hollow closure tube.

Example 15—The surgical instrument of Examples 10, 11, 12, 13 or 14, wherein at least one articulation member comprises a first articulation member that operably interfaces with the surgical end effector and a second articulation member that operably interfaces with the surgical end effector and wherein the articulation system comprises a dual acting solenoid that is configured to selectively engage each of the first and second articulation members.

Example 16—The surgical instrument of Example 15, wherein the means for retainingly engaging comprises a first serrated portion on the first articulation member, a first lock member on the elongate shaft assembly that is configured to retainingly engage the first serrated portion and a second serrated portion on the second articulation member and a second lock member on the elongate shaft assembly that is configured to retainingly engage the second serrated portion.

Example 17—The surgical instrument of Example 16, wherein when the dual acting solenoid engages the first articulation member, the dual acting solenoid moves the first serrated portion out of engagement with the first lock member and when the dual acting solenoid engages the second articulation member, the dual acting solenoid moves the second serrated portion out of engagement with the second lock member.

Example 18—The surgical instrument of Examples 15, 16 or 17, wherein the dual acting solenoid operably interfaces with a firing drive system of the surgical instrument.

Example 19—A surgical instrument that comprises an elongate shaft assembly that includes an articulation joint. A surgical end effector is operably coupled to the elongate shaft assembly for selective articulation about the articulation joint. A first articulation member operably interfaces with the surgical end effector and is supported for selective axial movement in response to an application of first articulation motions by a first articulation motor operably coupled thereto. The surgical instrument further comprises a second articulation member that operably interfaces with the surgical end effector and is supported for selective axial movement in response to an application of second articulation motions by a second articulation motor that is operably coupled thereto.

Example 20—The surgical instrument of Example 19 further comprising a control system for controlling the first and second articulation motors such that when the first articulation motor is operated to move the first articulation member in one axial direction a first axial distance, the second articulation motor is operated to move the second articulation member in an opposite axial direction a second axial distance that is equal to the first axial distance.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. Pat. No. 7,845,537, entitled SURGICAL INSTRUMENT HAVING RECORDING CAPABILITIES, which issued on Dec. 7, 2010;

U.S. patent application Ser. No. 12/031,573, entitled SURGICAL CUTTING AND FASTENING INSTRUMENT HAVING RF ELECTRODES, filed Feb. 14, 2008;

U.S. Pat. No. 7,980,443, entitled END EFFECTORS FOR A SURGICAL CUTTING AND STAPLING INSTRUMENT, which issued on Jul. 19, 2011;

U.S. Pat. No. 8,210,411, entitled MOTOR-DRIVEN SURGICAL CUTTING INSTRUMENT, which issued on Jul. 3, 2012;

U.S. Pat. No. 8,608,045, entitled POWERED SURGICAL CUTTING AND STAPLING APPARATUS WITH MANUALLY RETRACTABLE FIRING SYSTEM, which issued on Dec. 17, 2013;

U.S. Pat. No. 8,220,688, entitled MOTOR-DRIVEN SURGICAL CUTTING INSTRUMENT WITH ELECTRIC ACTUATOR DIRECTIONAL CONTROL ASSEMBLY, which issued on Jul. 17, 2012;

U.S. Pat. No. 8,733,613, entitled STAPLE CARTRIDGE, which issued on May 27, 2014;

U.S. Pat. No. 8,561,870, entitled SURGICAL STAPLING INSTRUMENT, which issued on Oct. 22, 2013;

U.S. Patent Application Publication No. 2012/0298719, entitled SURGICAL STAPLING INSTRUMENTS WITH ROTATABLE STAPLE DEPLOYMENT ARRANGEMENTS, filed on May 27, 2011, now U.S. Pat. No. 9,072,535;

U.S. Patent Application Publication No. 2013/0334278, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Pat. No. 8,308,040, entitled SURGICAL STAPLING INSTRUMENT WITH AN ARTICULATABLE END EFFECTOR, which issued on Nov. 13, 2012, are hereby incorporated by reference herein.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

What is claimed is:

1. A surgical instrument comprising:
   (a) a body;
   (b) a shaft extending distally from the body and along a shaft axis;
   (c) a slip ring assembly configured to electrically couple the body with the shaft, wherein the slip ring assembly includes a plurality of annular conductors arranged concentrically about the shaft axis and circumferentially about one another;
   (d) an end effector operatively coupled with the shaft and having first and second jaws that are configured to cooperate to clamp tissue; and
   (e) an articulation motor configured to selectively articulate the end effector relative to the shaft, wherein the articulation motor is distal to the body and the slip ring assembly.

2. The surgical instrument of claim 1, wherein the plurality of annular conductors includes at least three annular conductors and is configured to permit relative rotation between a first portion of the slip ring assembly and a second portion of the slip ring assembly while maintaining an electrically conductive pathway therebetween.

3. The surgical instrument of claim 1, wherein a first portion of the slip ring assembly and a second portion of the slip ring assembly are configured to rotate relative to each other upon rotation of the shaft relative to the body.

4. The surgical instrument of claim 1, wherein the slip ring assembly is configured to provide electrical power to the articulation motor to thereby articulate the end effector.

5. The surgical instrument of claim 1, wherein at least one annular conductor of the plurality of annular conductors is configured to maintain electrical connectivity between the body and the shaft during rotation of the shaft relative to the body.

6. The surgical instrument of claim 1, wherein the shaft is configured to rotate relative to the body, wherein the slip ring assembly is configured to maintain electrical conductivity between the body and the shaft during the rotation.

7. The surgical instrument of claim 1, wherein the end effector is configured to modify the tissue, wherein the body includes a control circuit, wherein the slip ring assembly includes a switch component, wherein the control circuit is configured to communicate with the switch component, wherein the switch component is configured to prevent the end effector from modifying the tissue.

8. The surgical instrument of claim 1, wherein the first and second jaws are configured to cooperate to staple the clamped tissue with a plurality of staples.

9. The surgical instrument of claim 1, further comprising a rack gear coupled with the articulation motor and configured to drive articulation of the end effector relative to the shaft.

10. The surgical instrument of claim 9, wherein the rack gear comprises a first rack gear configured to translate parallel to the shaft axis, wherein the surgical instrument further comprises a second rack gear configured to translate in opposition to the first rack gear.

11. The surgical instrument of claim 1, wherein the articulation motor is housed inside of a proximal portion of the shaft.

12. The surgical instrument of claim 1, wherein the articulation motor defines a motor axis, wherein the shaft axis and the motor axis are substantially perpendicular to each other.

13. The surgical instrument of claim 1, wherein the shaft includes a firing driver having a longitudinal slot, wherein a shaft of the articulation motor extends through the longitudinal slot such that the firing driver is longitudinally translatable relative to the articulation motor.

14. A surgical instrument comprising:
(a) a body;
(b) a shaft extending distally from the body, wherein the shaft includes a firing driver having a longitudinal slot;
(c) an end effector operatively coupled with the shaft and having first and second jaws that are configured to cooperate to clamp tissue;
(d) an articulation motor including a motor shaft and configured to selectively articulate the end effector relative to the shaft, wherein the articulation motor is distal to the body, wherein the motor shaft extends through the longitudinal slot such that the firing driver is longitudinally translatable relative to the articulation motor; and
(e) a rack gear operatively coupled with the articulation motor and configured to drive articulation of the end effector relative to the shaft.

15. The surgical instrument of claim 14, further comprising a slip ring assembly configured to act as an electrical conduit between the body and the shaft.

16. The surgical instrument of claim 15, wherein the slip ring assembly is configured to provide electrical power to the articulation motor to thereby articulate the end effector.

17. A surgical instrument comprising:
(a) a handle;
(b) a shaft extending distally from the handle along a longitudinal axis;
(c) an end effector operatively coupled with the shaft and having first and second jaws that are configured to cooperate to clamp tissue; and
(d) an articulation motor, wherein the articulation motor is distal to the handle and defines a motor axis that is substantially perpendicular to the longitudinal axis to thereby be configured for selective articulation of the end effector relative to the shaft, and wherein the articulation motor extends into the shaft.

18. The surgical instrument of claim 17, wherein the first and second jaws are configured to cooperate to staple the clamped tissue with a plurality of staples.

19. The surgical instrument of claim 17, wherein the shaft is rotatable relative to the handle, wherein the articulation motor is configured to maintain electrical connectivity with the handle during rotation of the shaft relative to the handle.

20. The surgical instrument of claim 17, further comprising a rack gear configured to be driven parallel to the longitudinal axis by the articulation motor to thereby articulate the end effector relative to the shaft.

* * * * *